(12) United States Patent
Gordon et al.

(10) Patent No.: US 8,299,019 B2
(45) Date of Patent: Oct. 30, 2012

(54) USES OF MODIFIED ELR-CXC CHEMOKINE G31P TO TREAT CANCER

(76) Inventors: John R. Gordon, Saskatoon (CA); Fang Li, Dalian (CN)

( * ) Notice: Subject to any disclaimer, the term of this patent is extended or adjusted under 35 U.S.C. 154(b) by 20 days.

(21) Appl. No.: 13/048,290

(22) Filed: Mar. 15, 2011

(65) Prior Publication Data
US 2012/0070405 A1 Mar. 22, 2012

Related U.S. Application Data

(63) Continuation-in-part of application No. 12/866,952, filed as application No. PCT/CA2009/000170 on Feb. 12, 2009.

(60) Provisional application No. 61/027,959, filed on Feb. 12, 2008, provisional application No. 61/043,573, filed on Apr. 9, 2008.

(51) Int. Cl.
*A61K 38/00* (2006.01)
(52) U.S. Cl. .......................................... 514/1.7; 514/1.8
(58) Field of Classification Search .................... None
See application file for complete search history.

(56) References Cited

OTHER PUBLICATIONS

Uslu et al. Predictive value of serum interleukin-8 levels in ovarian cancer patients treated with paclitaxel-containing regimens, Int. J. Gynecol. Cancer, 15, 240, 2005. (abstract).*

* cited by examiner

*Primary Examiner* — Elly-Gerald Stoica
(74) *Attorney, Agent, or Firm* — Michael R Williams; Adrian D. Battison; Ade & Company Inc.

(57) ABSTRACT

Described herein is the use of a modified human chemokine, GS-CXCL8$_{(3-72)}$K11R/G31P or G31P in the treatment of a number of cancers, including but by no means limited to prostate cancer, liver cancer and melanoma.

9 Claims, 34 Drawing Sheets

Figure 12
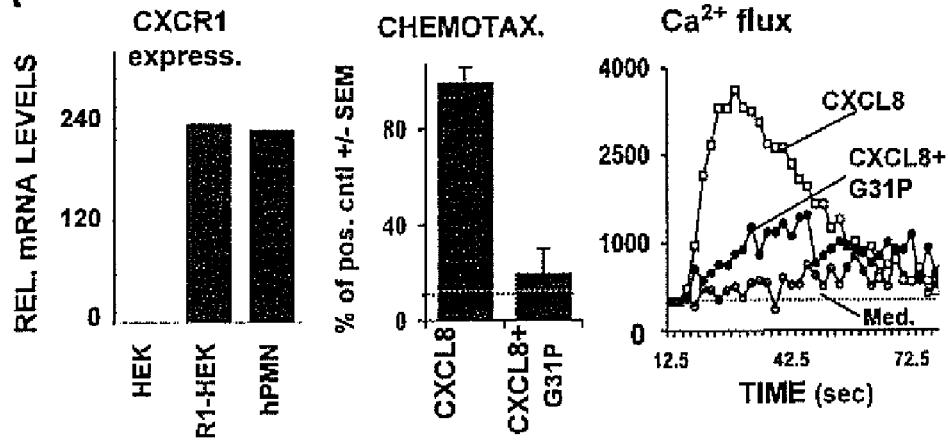
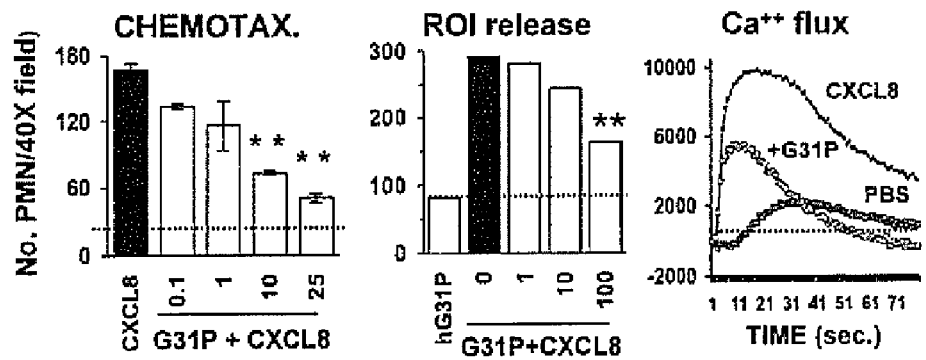
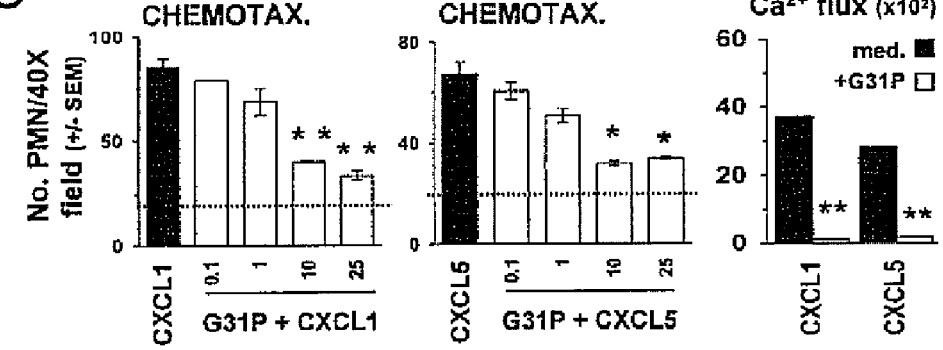

Fig. 21  *G31P treatments reduce the development of melanoma metastases in an mouse i.v. B16 tumour cell model.*

Fig. 26
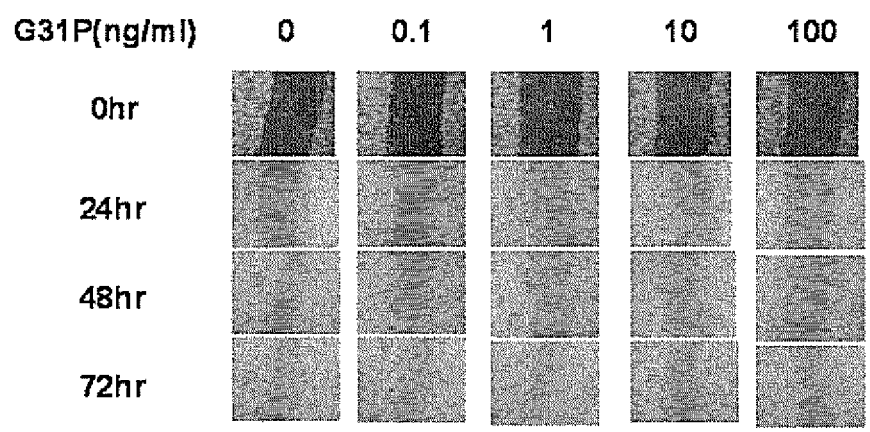
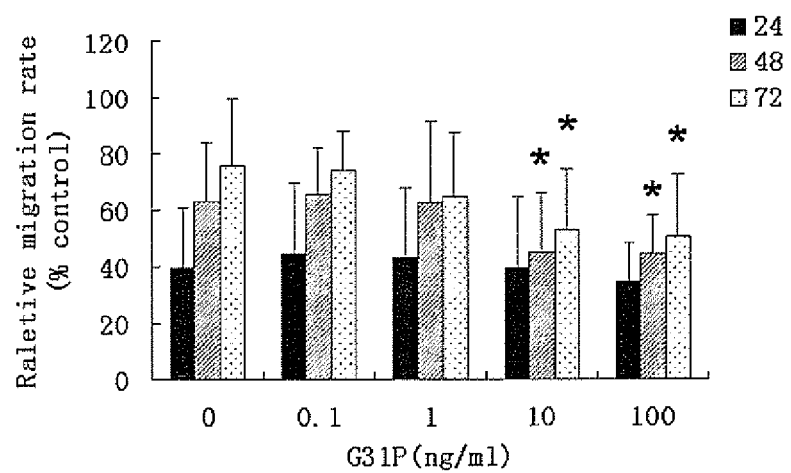

Fig. 31 *Impact of G31P on tumour growth and metastasis in an orthotopic mouse model of human prostatic cancer*
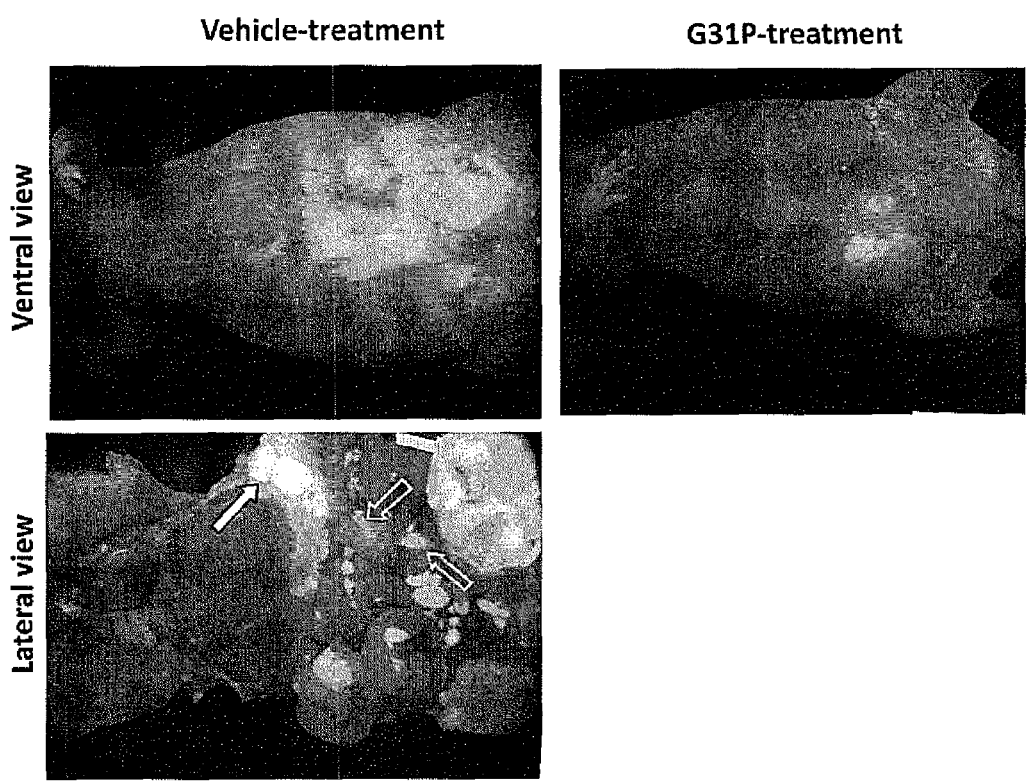

Fig. 32  *Representative images employed for angiogenesis calculations*
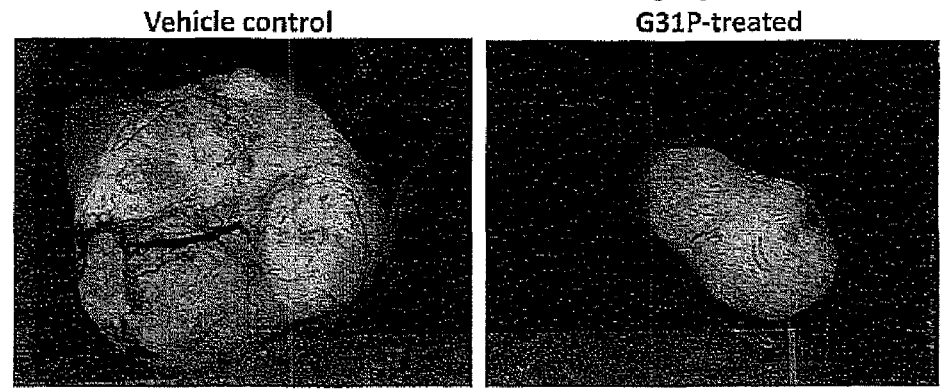
Fig. 33
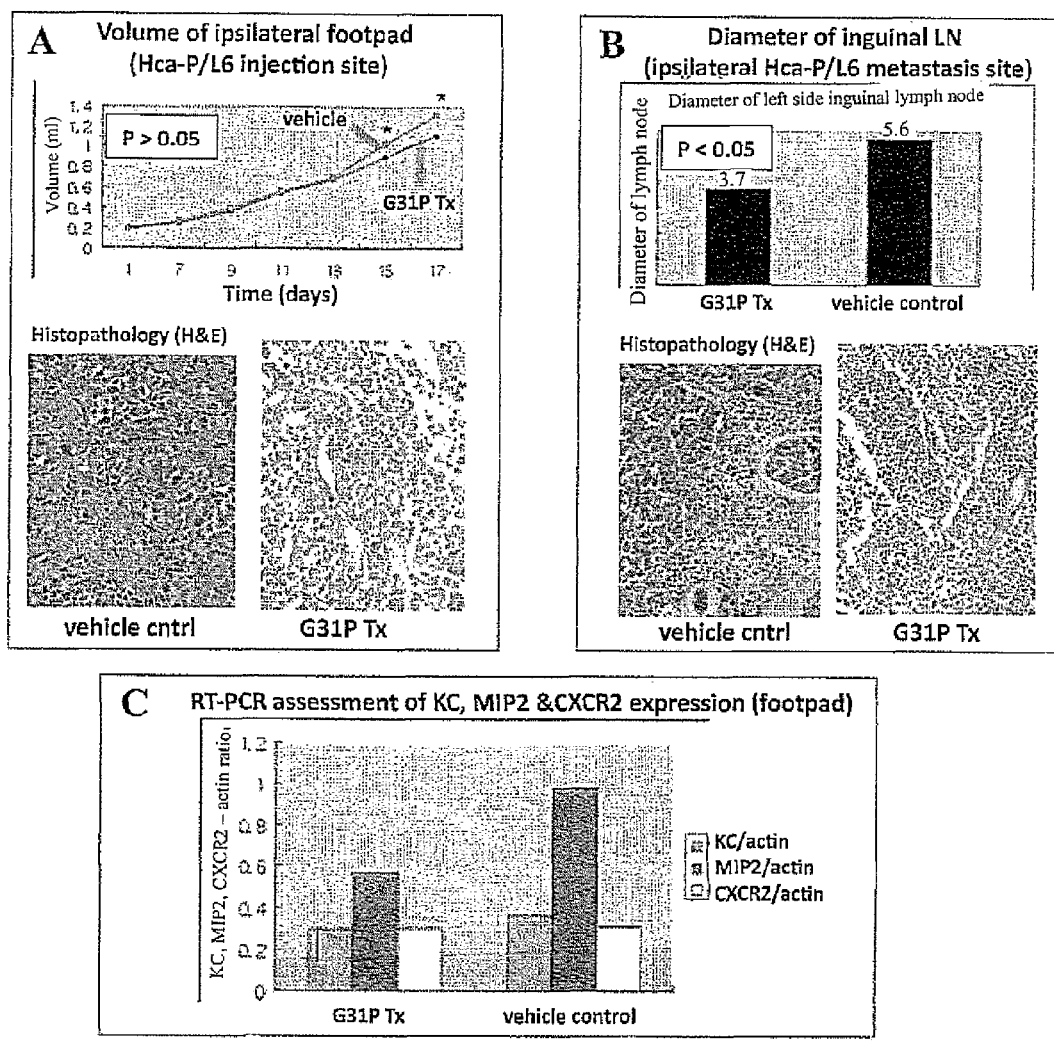

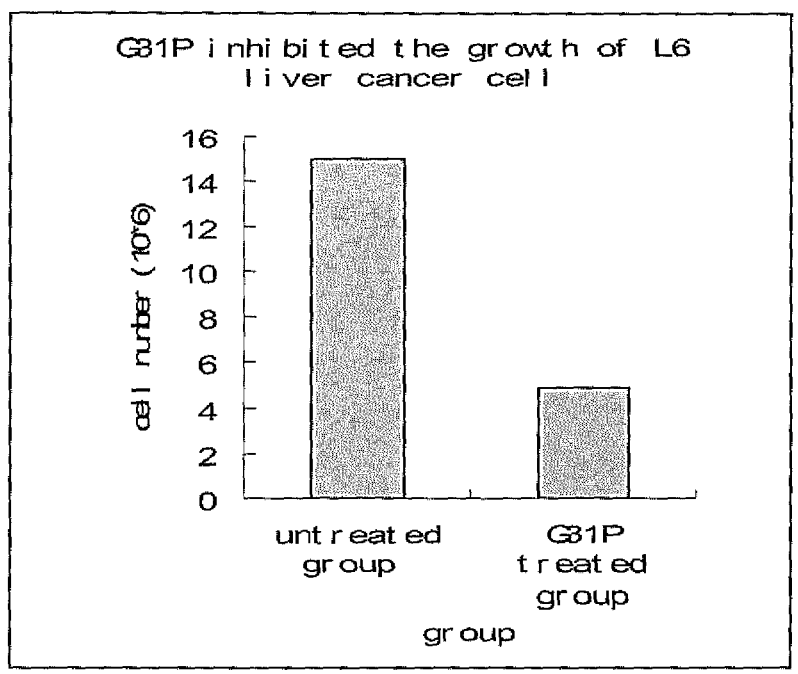
Fig. 34 The comparison of cell numbers in the ascitic fluid between two group.
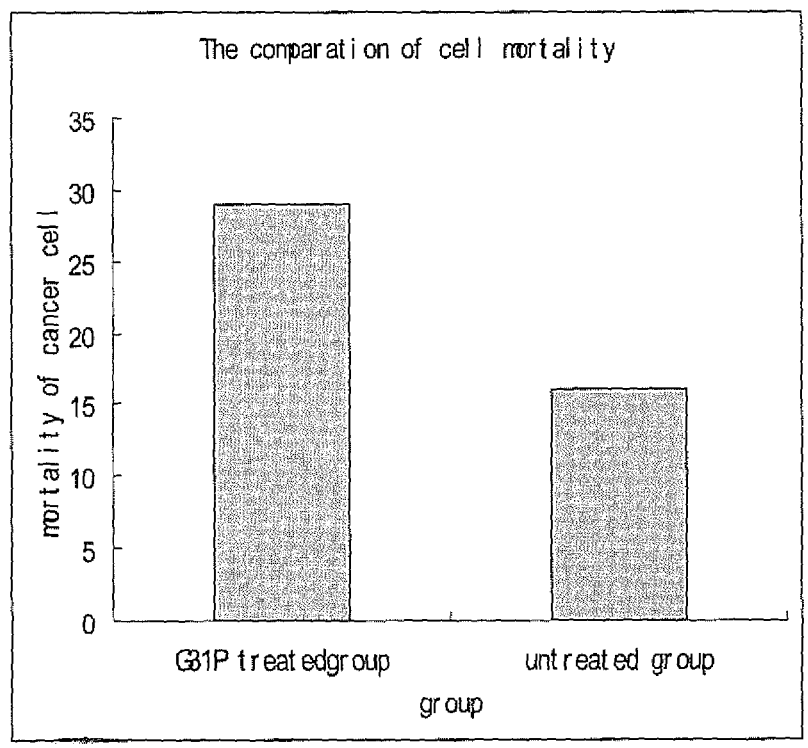
Fig. 35 The comparison of mortality between the two groups

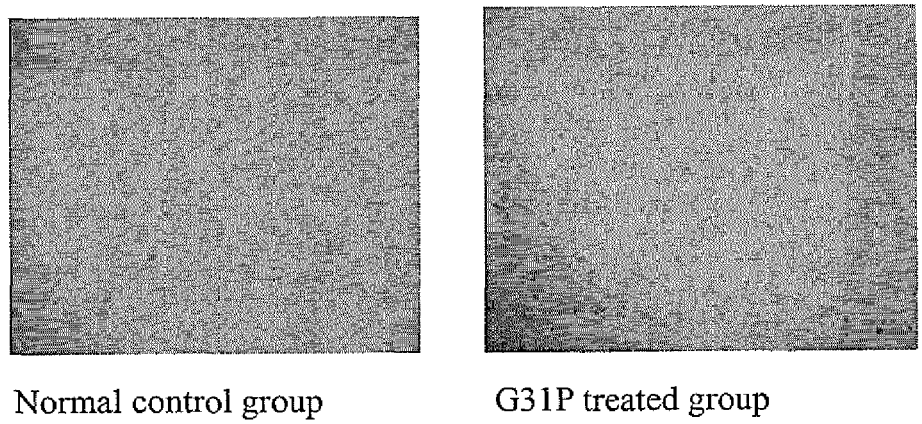
Fig. 36 The comparison of tumor cell shape in the ascitic fluid between two groups

SEQUENCE LISTING

<160> NUMBER OF SEQ ID NOS: 11

<210> SEQ ID NO 1
<211> LENGTH: 72
<212> TYPE: PRT
<213> ORGANISM: artificial
<220> FEATURE:
<223> OTHER INFORMATION: modified human CXCL8 sequence

<400> SEQUENCE: 1

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 2
<211> LENGTH: 23
<212> TYPE: DNA
<213> ORGANISM: artificial
<220> FEATURE:
<223> OTHER INFORMATION: B-actin forward PCR primer

<400> SEQUENCE: 2
cgtaaggacc tctatgccaa cac                                      23

<210> SEQ ID NO 3
<211> LENGTH: 23
<212> TYPE: DNA
<213> ORGANISM: artificial
<220> FEATURE:
<223> OTHER INFORMATION: B-actin reverse PCR primer

<400> SEQUENCE: 3
gactcatcgt actcctgctt gct                                      23

<210> SEQ ID NO 4
<211> LENGTH: 22
<212> TYPE: DNA
<213> ORGANISM: artificial
<220> FEATURE:
<223> OTHER INFORMATION: CXCL1 forward PCR primer

<400> SEQUENCE: 4
cccaagaaca tccagagcgt ag                                       22

<210> SEQ ID NO 5
<211> LENGTH: 20
<212> TYPE: DNA
<213> ORGANISM: artificial
<220> FEATURE:
<223> OTHER INFORMATION: CXCL1 reverse PCR primer

<400> SEQUENCE: 5
tggctttgct tcctttcagc                                          20

<210> SEQ ID NO 6
<211> LENGTH: 23
<212> TYPE: DNA
<213> ORGANISM: artificial
<220> FEATURE:
<223> OTHER INFORMATION: CXCL8 forward PCR primer

<400> SEQUENCE: 6
tgcgatgcca gtgtattaag att                                      23

<210> SEQ ID NO 7
<211> LENGTH: 23

```
<212> TYPE: DNA
<213> ORGANISM: artificial
<220> FEATURE:
<223> OTHER INFORMATION: CXCL8 reverse PCR primer

<400> SEQUENCE: 7
ctcttcaaga acatgctcac cac                                         23

<210> SEQ ID NO 8
<211> LENGTH: 19
<212> TYPE: DNA
<213> ORGANISM: artificial
<220> FEATURE:
<223> OTHER INFORMATION: GADPH forward PCR primer

<400> SEQUENCE: 8
tgcctcctgc accaccaac                                              19

<210> SEQ ID NO 9
<211> LENGTH: 20
<212> TYPE: DNA
<213> ORGANISM: artificial
<220> FEATURE:
<223> OTHER INFORMATION: GAPDH reverse PCR primer

<400> SEQUENCE: 9
ggccatccac agtcttctgg                                             20

<210> SEQ ID NO 10
<211> LENGTH: 22
<212> TYPE: DNA
<213> ORGANISM: artificial
<220> FEATURE:
<223> OTHER INFORMATION: cxcl1 PCR primer

<400> SEQUENCE: 10
cccaagaaca tccaaagtgt ga                                          22

<210> SEQ ID NO 11
<211> LENGTH: 22
<212> TYPE: DNA
<213> ORGANISM: artificial
<220> FEATURE:
<223> OTHER INFORMATION: cxcl1 reverse primer

<400> SEQUENCE: 11
gtcactgttc agcatctttt cg                                          22
```

USES OF MODIFIED ELR-CXC CHEMOKINE G31P TO TREAT CANCER

PRIOR APPLICATION INFORMATION

The instant application is a continuation in part of U.S. patent application Ser. No. 12/866,952, filed Oct. 25, 2010 which was a national phase entry of PCT Patent Application PCT/CA2009/000170, filed Feb. 12, 2009 which in turn claims the benefit of U.S. Provisional Patent Application 61/027,959, filed Feb. 12, 2008 and U.S. Provisional Patent Application 61/043,573, filed Apr. 9, 2008.

BACKGROUND OF THE INVENTION

Neutrophil responses are a critical element in host defense during, for example, bacterial infections, but neutrophil responses can also be overtly pathogenic. Thus, in many inflammatory diseases neutrophils contribute more to the pathology than do the microbes themselves (Nathan, 2002, *Nature* 420:846-852). Neutrophil recruitment is a complex process involving activation of local structural cells (e.g., epithelial cells) via pathogen-associated molecular pattern receptors, complement cascade products or arachidonic acid metabolites, such that the structural cells express inflammatory mediators (e.g., IL-1, CXCL8) (Smith et al., 2001, *J. Immunol.* 167:366-374). These can in turn activate regional endothelial cells, which actively foster extravasation of neutrophils via the now classical paradigm of chemokine- (e.g., CXCL8) and adhesion molecule-mediated rolling-arrest-diapedesis (Baggiolini, 1998, *Nature* 392:565-568; Springer, 1994, *Cell* 76:301-314).

The ELR-CXC chemokines are a subgroup of the CXC chemokine family in which the amino sub-terminal two cysteine residues (i.e., CXC), which are separated by an alternate amino acid, are immediately preceded by a Glu-Leu-Arg (i.e., ELR) motif. They include CXCL1-3 and 5-8 (growth-related oncogene α, β, and γ [GRO α, β, and γ], epithelial cell neutrophil-activating peptide-78 [ENA-78], granulocyte chemotactic protein-2 [GCP-2], neutrophil activating peptide-2 [NAP-2], and interleukin-8 [IL-8], respectively)(Baggiolini, 1998, Nature 392:565) which chemoattract and activate neutrophils via two closely related G protein-coupled receptors (GPCR), the CXCR1 and CXCR2. CXCL8 binds both receptors with high affinity, while CXCL6 binds both receptors with lower affinity (Wolf et al., 1998, *Eur. J. Immunol.* 28:164-170; Wuyts et al., 1998, *Eur. J. Biochem.* 255:67-73). The other ELR-CXC chemokines bind to the CXCR2, also with relatively lower affinities (Wuyts et al., 1998; Ahuja and Murphy, 1996, *J. Biol. Chem.* 271:20545-20550). Both the CXCR1 and CXCR2 can trigger chemotactic responses and intracellular $Ca^{2+}$ flux in neutrophils and contribute to elastase release (Wuyts et al., 1998; Chuntharapai and Kim, 1995, *J. Immunol.* 155:2587-2594), but activation of the respiratory burst and phospholipase D release responses are reportedly CXCR1-dependent (Jones et al., 1996, *Proc. Natl. Acad. Sci. U.S.A.* 93:6682-6686), whereas CXCR2 signaling is critical to MMP-9 release (Chakrabarti and Patel, 2005, *J. Leukoc. Biol.* 78:279-288). Moreover, these two receptors may be differentially involved in neutrophilic pathology in vivo. For example, the CXCR1 is reportedly of more importance in inflammatory bowel diseases (Gijsbers et al., 2004, *Eur. J. Immunol.* 34:1992-2000), sepsis and acute respiratory distress syndrome (Cummings et al., 1999, *J. Immunol.* 162:2341-2346; Goodman et al., 1999, *Chest* 116:111s-112s), while it and the CXCR2 both play roles in synovial infiltration by neutrophils in arthritic joints (Podolin et al., 2002, *J. Immunol.* 169:6435-6444). However, numerous alternate GPCRs are involved in neutrophilic inflammation, including those for LTB4, C5a, and fMLP, such that antagonism of either LTB4 or C5a has been shown to be of significant benefit in various inflammatory settings (Park et al., 2000, *Anesth. Analg.* 89:42-48; Crooks at al., 2000, *Eur. Respir. J.* 15:274-280; Wollert et al., 1993, *Surgery* 114:191-198). The precise interrelationships between these mediators in inflammatory responses have not been formally determined, but it has been reported that signaling through the C5a or fMLP receptors can effectively desensitize the ELR-CXC chemokine receptors (Blackwood et al., 1996, *J. Leukoc. Biol.* 60:88-93). On the other hand, CXCL8 reportedly poorly desensitizes some events (e.g., intracellular $Ca^{++}$ flux) associated with C5a and fMLP receptor signaling (Richardson et al., 1995, *J. Biol. Chem.* 270:27829-27833; Tomhave et al., 1994, *J. Immunol.* 153:3267-3275), although it can desensitize chemotactic responses driven by these ligands.

There are an array of inflammatory settings in which neutrophils are the primary drivers of host pathology and for some of these one or more ELR-CXC chemokines have been implicated in the neutrophil response. When activated, neutrophils release an array of microbicidal factors, including reactive oxygen intermediates (ROI), defensins, and proteolytic enzymes, but they also foster the inflammatory responses through elaboration of proinflammatory cytokines (e.g. TNF, IL-1) and ELR-CXC chemokines themselves (e.g., CXCL1, CXCL8). Aspiration pneumonia, brought on by aspiration of highly acidified gastric contents into the lungs, occurs primarily in unconscious or semiconscious patients. Its incidence is approximately 1 in 3000 during general anaesthesia surgeries (Olsson et al., 1986, Acta Anaesthesiol Scand. 30:84-92; Warner et al., 1993, Anesthesiology 78:56-62). The local inflammatory sequel varies from sub-clinical pneumonitis to severe acute lung injury (ALI) and acute respiratory distress syndrome (ARDS) (Pepe at al., 1982, Am J Surg 144:124-30; Fowler et al., 1983, Ann Intern Med 98:593-7) depending on the volume and the pH of the gastric contents (Marik, 2001, N Engl J Med 344:665-71). However, ALI/ARDS associated with aspiration pneumonia carries a mortality rate of 10-30% (Olsson et al., 1986; Warner et al., 1993). It is recognized that neutrophils are the primary drivers of the inflammatory cascade in aspiration pneumonia (Beck-Schimmer et al., 2005, Anesthesiology 103:556-66; Raghavendran et al., 2005, Am J Physiol Lung Cell Mol Physiol 289:L134-43; Folkesson et al., 1995, J Clin Invest 96:107-16; Davidson et al., 2005, Am J Physiol Lung Cell Mol Physiol 288:L699-708) and that the ELR-CXC chemokines are central to the recruitment and activation of neutrophils in aspiration pneumonia (Beck-Schimmer et al., 2005; Folkesson et al., 1995; Rotta et al., 2004, Crit. Care Med 32:747-54). This suggests that, in the case of aspiration pneumonia, for example, ELR-CXC chemokine antagonism could be an ideal therapeutic approach to ameliorate pathology, and this applies also to many neutrophilic inflammatory disorders (Walley et al, 1997, Infect Immun 65:3847; Kishimoto et al, 2001, J Virol 75:1294; Mukaida et al, 1998, Inflamm Res 47 (Suppl 3):S151; Jones et al, 1997, J Biol Chem 272:16166; White et al, 1998, J Biol Chem 273:10095)

Previously, we generated a broad-spectrum ELR-CXC chemokine antagonist bovine $CXCL8_{(3-74)}K11R/G31P$ (bG31P) (Li and Gordon, 2001, Biochem Biophys Res Commun 286:595-600; Li et al., 2002, Biochem Biophys Res Commun 293:939-44), which blocks the ability of ELR-CXC chemokines to activate and chemoattract neutrophils in vitro (Li et al., 2002). A single treatment with bG31P≈97% blocks neutrophil infiltration into intradermal endotoxin challenge sites for 2-3 days (Li et al., 2002, Vet Immunol Immunopathol 90:65-77), and dramatically reduces pulmonary pathology and pyrexia in animals suffering from airway endotoxin challenge (Gordon et al., 2005, J Leukoc Biol 78:1265-72). In the process of generating a human homologue of bG31P we developed multiple human-bovine chaemeric forms of bG31P that were also effective in antagonizing ELR-CXC chemokine-mediated airway endotoxin-induced pathology (Zhao et al., 2007, Internat Immunopharmacol 7:1723-31), and more recently we engineered a fully human form of G31P, human $CXCL8_{(3-72)}K11R/G31P$ (G31P). This latter drug not only blocks neutrophil activation induced by ELR-CXC chemokines, but also human airway epithelial cell responses driven by bacterial lipopolysaccharide (LPS). Importantly, it also partially antagonizes heterologous GPCRs that are involved in neutrophilic inflammation, including those for C5a, LTB4, and fMLP (Zhao et al, 2009, J Immunol 182:3213). We subsequently showed that G31P can highly effectively reduce lung pathology in a guinea pig model of aspiration pneumonia, and that it did so without negatively impacting bacterial clearance in the lungs of the affected animals (Zhao et al, 2010, Pulm Pharmacol & Therap 23:22)(see also FIGS. 1-5).

Neutrophilic inflammation is also thought to be critical to both local and remote organ injury following mesenteric artery ischemia-reperfusion (I/R) injury. Intestinal I/R injury is associated with severe multiple organ failure (MOF), including the lung as one such remote organ (He et al., 2008, PLoS ONE 3: e1527; Schmeling et al., 1989, Surgery 106: 195-201; Caty et al., 1990, Ann Surg 212: 694-700). A number of proinflammatory cytokines and chemokines are critically involved in this pathology (Caty at al., 1990) although the pathogenesis of intestinal I/R-induced gut pathology and MOF is complex and not completely understood. Nonetheless, reactive oxygen intermediate (ROI) generation and neutrophil sequestration are believed to be two fundamental causative factors (Schmeling et al., 1989; Cerqueira et al., 2005, Acta Cir Bras 20: 336-343; Souza et al., 2004 Br J Pharmacol 143: 132-142). The pivotal role of neutrophils in these processes (Schmeling at al., 1989; Cerqueira et al., 2005; Bless et al., 1999, Am J Physiol 276: L57-63) suggests that, here too, blockade of their recruitment could be an important therapeutic approach to intestinal I/R injury. The list of neutrophil agonists potentially involved in I/R injury includes TNFα and IL-β (Caty et al., 1990) and the ELR-CXC chemokines (e.g., CXCL1, CXCL8, MIP-2) (Schmeling, et al., 1989; Bless et al., 1999; Sekido et al., 1993, Nature 365: 654-657), but also C5a (Bless at al., 1999; Wada et al., 2001, Gastroenterology 120: 126-133), LTB4 (Souza at al., 2000, Eur J Pharmacol 403: 121-128), ROI (Koike et al., 1993, J Surg Res 54: 469-473), and adhesion molecules (Bless at al., 1999). Multiple reports have implicated individual ELR-CXC chemokines as primary effectors and shown that their neutralization ameliorates I/R-induced local and remote organ pathology (Souza et al., 2004; Bless et al., 1999; Miura et al., 2001, Am J Pathol 159: 2137-2145; Kaneko et al., 2007, Eur Surg Res 39: 153-159), making these mediators attractive therapeutic targets. Given this broad panel of inflammatory mediators (many of which employ GPCR as their cellular receptors) implicated in intestinal I/R injury, the above-noted abilities of G31P to induce desensitization of heterologous GPCR raises the question of whether G31P would be particularly useful as a therapeutic approach in this disease. Thus, we assessed this in a rat model of superior mesenteric artery (SMA) I/R injury, treating the animals with G31P and examining their local and remote organ pathology in this model. We found that G31P reduced mortality in the I/R rats by 50% relative to saline-treated I/R animals, and that it reduced local and remote organ injury (Zhao et al, 2010, J Surg Res 162:264)(see also FIGS. 6-12).

Some of the protective effects of bG31P in airway endotoxemia, for example, seemed to be somewhat tangentially related to its putative neutrophil-centered effects. For example, bG31P treatment reduces endogenous pyrogen expression and pyrexia prior to the time when neutrophils were appreciably present in the airways, suggesting that it may have effects on structural (e.g., epithelial) cells. Moreover, data from a study of its effects in aspiration pneumonia, wherein high level bacterial colonization of the lungs occurs, confirmed its effectiveness in this environment as well. In such cases the bacteria would release formyl peptides (e.g., fMLP) among other products and activate the complement cascade, leading to the generation of C5a. Thus, formally explored further the mechanisms by which G31P might interact with airway epithelial cells, but also its effect on neutrophil responses to ligands for heterologous GPCR, and its specificity for the CXCR1 and CXCR2 (Zhao et al, 2009, J Immunol 182:3213) (See also FIGS. 12-19).

Just as the ELR-CXC chemokines can activate neutrophils and epithelial cells, there is abundant evidence that they have important roles in the biology of other types of cells, including transformed (i.e., cancer) cells. ELR-CXC chemokines such as CXCL1, CXCL6, or CXCL8 are secreted by a variety of human tumor cells and are involved in a number of important tumor-related biological processes, including tumor formation, development, and responses to chemotherapy in the context of melanoma, ovarian, prostate, pancreatic, bladder, lung and breast cancers (Araki et al., 2007, Cancer Res 67:14; Luppi et al., 2007, Lung cancer 56: 25-33; MacManus et al., 2007, Mol Cancer Res 5; Zhu et al, 2006, Br J Cancer 94:1936; Oladipo et al, 2011, Br J Cancer 104:480). Indeed, the levels at which CXCL8, for example, are expressed by prostate cancer PC-3 cells, for example, correlates well with the extent to which the cells develop into tumors, promote neovascularization, and metastasize following orthotopic implantation into nude mice (Kim et al, 2001, Neoplasia 3:33). Significantly, CXCR1 and CXCR2 are expressed at high levels in many tumour cells including prostate cancer cells (Kim et al, 2001), melanoma (Singh et al, 2010, Future Oncol 6:111; Singh et al, 2009, Br. J. Cancer 100:1638), and adenocarcinoma (Varney et al, 2011, Cancer Left 300:180) cells, and in each case these receptors contribute importantly to tumour growth, metastasis and angiogenesis (Kim et al, 2001; Singh et al, 2010; Singh et al, 2009; Varney et al, 2011).

Herein, we tested whether ELR-CXC chemokine antagonism with G31P would by itself be beneficial in mouse models of melanoma, hepatic adenocarcinoma, and orthotopic human prostate cancer. We assessed the impact of G31P on a number of tumor cell parameters, including chemokine-driven tumour cell proliferation, in vitro. We also assessed the impact of G31P on tumor growth, metastasis and angiogenesis in vivo

SUMMARY OF THE INVENTION

According to an aspect of the invention, there is provided a method of treating cancer in an individual in need of such treatment comprising administering to said individual an effective amount of G31P (SEQ ID No. 1).

BRIEF DESCRIPTION OF THE DRAWINGS

FIG. 12. The ELR-CXC chemokine antagonist $CXCL8_{(3-72)}$ K11R/G31P operates by targeting the CXCR1 and CXCR2 on neutrophils. (A) We generated CXCR1-transfected HEK293 cells and used these to determine whether human (h) G31P acts via the CXCR1. We used qRT-PCR to assess CXCR1 expression by control and CXCR1-transfected HEK cells and compared this expression with that of peripheral blood neutrophils (left panel). For the chemotaxis assays, responses to an optimized concentration of CXCL8 (10 ng/ml) were assessed using modified Boyden chamber microchemotaxis assays. The ability of G31P (10 ng/ml) to antagonize this response was assessed by simultaneously exposing the cells to the agonist and antagonist. The results are expressed as the mean (±SEM) number of cells/40× objective microscope field (middle panel). For the $Ca^{++}$ flux assays, neutrophils were labeled with the $Ca^{++}$ indicator dye fluo-4 AM and assayed in the presence (100 ng/ml) or absence of G31P for chemokine (100 ng/ml)-induced intracellular $Ca^{2+}$ flux as described in the Materials and Methods (right panel). (B) We also assessed whether G31P could antagonize CXCL8-dependent chemotaxis, reactive oxygen intermediate (ROI) release by leukocytes, and intracellular $Ca^{2+}$ flux responses by purified human neutrophils using the same approaches as in panel A. (C) In order to confirm that G31P also acted via the CXCR2 we tested its ability to antagonize neutrophil chemotactic and intracellular $Ca^{++}$ flux responses induced by the CXCR2-exclusive ligands CXCL1 and CXCL5 (both 100 ng/ml). Our data confirm that G31P did effectively antagonize both CXCR1- and CXCR2-dependent responses. * and **, $p<0.05$ and 0.01, respectively, relative to the chemokine treatments alone. The data shown are representative of at least three experiments performed with similar results. The dashed lines across graphs in panels A, B, and C represent the mean background response in the indicated assays.

FIG. 26. G31P inhibits migration of PC-3 cells in a wound healing assay. Cells were cultured and allowed to become 100% confluent, then the injury line was made with a 200 µl sterilized pipette tip. The cells were then incubated with G31P at various concentrations (0, 0.1, 1, 10, 100 ng/ml) in RPMI1640 medium containing 1% fetal bovine serum for 0, 24, 48, 72 h at 37° C. (5% CO2). (A) Migration of the PC-3 Cell was observed by microscopy at the indicated time points (magnification, ×40). (B) The relative migration rate of PC-3 cells. The graph represents the mean±SD values (n=3) of triplicate cultures (* $p<0.05$ vs. control).

FIG. 31. Impact of G31P on tumor growth and metastasis in an orthotopic mouse model of human prostatic cancer. Nude mice were implanted s.c. with a 1 mm$^3$ slice of PC3-GFP solid tumor on day 0 and treated with 500 µg/kg G31P i.p. every second day commencing on day 0 (n=6). Depicted are whole body fluorescent scans of representative mice from each group, taken at day 29. Solid arrows indicate the primary prostate tumor as a solid mass. The hollow arrow indicates mesenteric lymph node (L.N.) metastases, the hollow arrow indicates lumbar L.N. metastases, and the solid arrows indicate metastases to the pancreas.

FIG. 32. Representative images employed for angiogenesis calculations. Nude mice were implanted s.c. with a slice of PC3-GFP solid tumor and treated with G31P as in FIG. 31. The extent of blood vessel development in the tumors was evaluated based on the total length of blood vessels in areas containing the highest number of vessels, as determined from fluorescent scans. The total number of pixels associated with the blood vessels was quantified with IMAGE PRO IMAGE 5.1 software. Table 3 shows total vessel length in a hypervascularized area of the primary tumor for each group, as determined from images such as these.

FIG. 33. Impact of G31P treatment on lymphatic metastases in a mouse model of murine ascites hepatocarcinoma. Strain 615 mice were given Hca-P/L6 hepatocarcinoma cells s.c. into the left digiti pedis (foot) and treated with 500 µg/kg G31P or vehicle control i.p. every second day commencing on day 0 (n=6). The mice were assessed clinically and (A) the volume of the foot assessed every second day. They were sacrificed on day 21 for assessment of footpad histopathology and lymph node metastases, as determined from the original site, and the ipsi- and contra-lateral inguinal and axillary lymph nodes, as well as the para-aortic nodes. (B) Ipsilateral inguinal LN diameter and histopathological appearance. (C) RT-PCR assessment of the levels of KC, MIP2 and CXCR2 expression in the ipsilaterial footpad.

FIG. 34. Comparison of cell numbers in the ascites fluids of two groups of mice treated as in FIG. 33.

FIG. 35. Comparison of mortality between two groups of mice treated as in FIG. 33.

FIG. 36. Comparison of shape of tumour cells recovered from the ascites fluids of two groups of mice treated as in FIG. 33.

DESCRIPTION OF THE PREFERRED EMBODIMENTS

Figure 1:
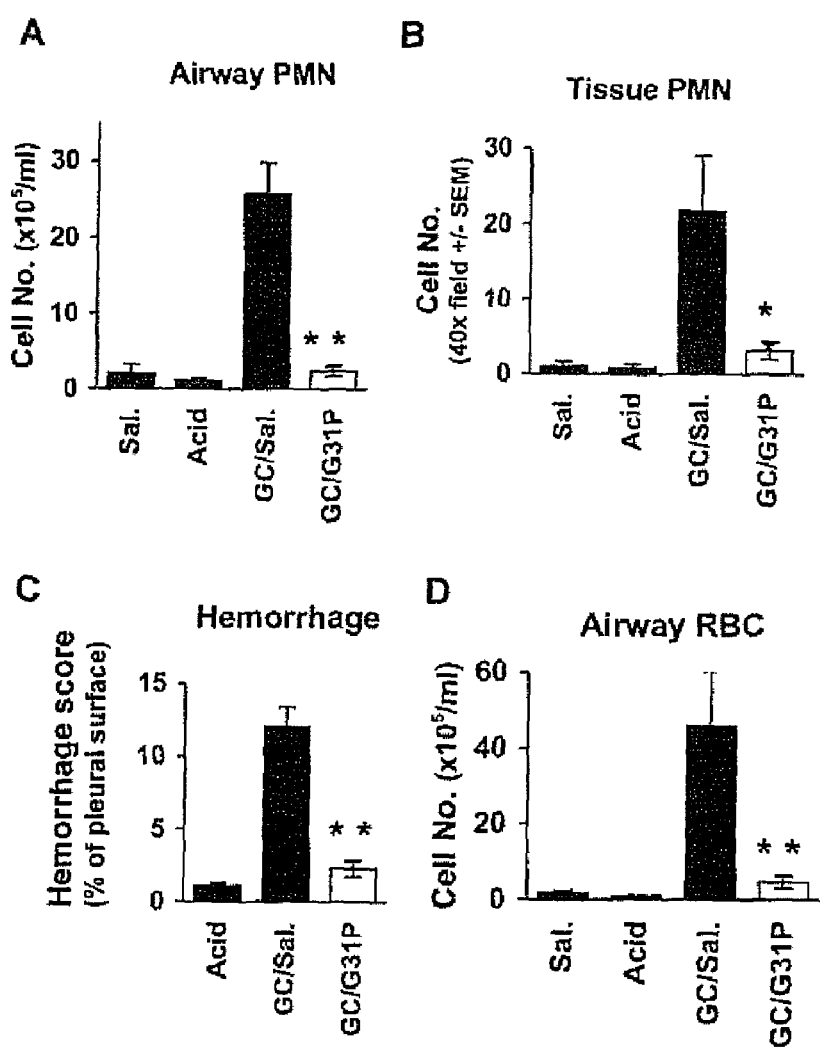
FIG. 1. Human $CXCL8_{(3-72)}K11R/G31P$ can effectively block neutrophil infiltration and reductions in vascular integrity in aspiration pneumonia animals. Aspiration pneumonia was induced in guinea pigs (n=5) by intranasal instillation of 250 μl of saline containing 35 mg/kg acidified gastric contents (GC, pH=2.0). One of two groups of gastric contents challenged animals were given 250 μg/kg $CXCL8_{(3-72)}$ K11R/G31P (G31P) subcutaneously 15 min prior to GC instillation, and then the animals were killed at 20 h post-challenge. Normal control and acid only groups (Sal. and Acid) were instilled with 250 μl of pH 7.2 or pH 2.0 saline, respectively. (A) Bronchoalveolar lavage (BAL) white blood cells were enumerated and differential counts were performed for each animal. The neutrophil (PMN) numbers were calculated from this data (Airway PMN), which are expressed as the mean number of cells $(\times 10^5)$/ml (+/−SEM). (B) The tissue neutrophil response was assessed by direct counting of haematoxylin & eosin-stained lung tissue sections (Tissue PMN) and the data expressed as the mean number of cells in each 40× object fields (+/−SEM). (C) In addition, the BAL red blood cell (RBC) was enumerated as above, and the data were expressed in the same way as airway PMN. The results demonstrated that 250 μg/kg G31P significantly reduced the 20 h airway and tissue neutrophil responses ($p < 0.01$, and $p < 0.05$), and reduced the appearance of red blood cells in the airways ($p < 0.01$). Data shown in these figures are from one experiment that is representative of three repeats. *, $p < 0.05$ or **, $p < 0.01$, versus the saline-treated, GC-challenged animal values.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Described herein are uses of G31P, more specifically human GS-CXCL8$_{(3-72)}$K11R/G31P, which binds with high affinity to both the CXCR1 and CXCR2, and thereby acts as a highly efficient competitive antagonist of all ELR-CXC chemokines.

```
G31P (SEQ ID No. 1):
GSKELRCQCI RTYSKPFHPK FIKELRVIES PPHCANTEII

VKLSDGRELC LDPKENWVQR VVEKFLKRAE NS
```

As discussed herein, an effective amount of the G31P (SEQ ID No. 1) peptide can be used as a treatment for a number of diseases or disorders, including but by no means limited to pulmonary disorders, inflammatory diseases and disorders, cancers and surgical/ischemia reperfusion applications.

Examples of pulmonary disorders include but are by no means limited to COPD, asthma, anaphylaxis, ARDS, diffuse panbronchiotitis, idiopathic pulmonary fibrosis, pneumonia, aspiration pneumonia, bronchitis, Cystic Fibrosis pneumonitis, and respiratory acidosis.

Examples of inflammatory diseases and disorders include but are by no means limited to inflammatory arthritic disorders, inflammatory bowel diseases and inflammatory dermatological disorders.

Examples of inflammatory arthritic disorders include but are by no means limited to osteoarthritis, ankylosing spondylitis, gout, schleroderma, psoriasis, vasculitides, rheumatoid arthritis, systemic lupus erythematosus, multiple sclerosis and pemphigus.

Examples of inflammatory bowel diseases include but are by no means limited to Crohn's disease and ulcerative colitis.

Examples of dermatological disorders include but are by no means limited to eczema, psoriasis, schleroderma, poison oak and palmoplantar dermatitis.

Examples of surgical/ischemia reperfusion applications include but are by no means limited to uveitis, organ transplant, occlusive and embolic stroke, myocardial infarction, organ failure, severe trauma, reperfusion lung injury, ventilator-induced injury and atherosclerosis.

In another embodiment of the invention, an effective amount of the G31P (SEQ ID No. 1) peptide can be used as a treatment for a number of different types of cancer. In some embodiments, these include but are by no means limited to tumor types responsive to ELR-CXC chemokines such as CXCL8, for example, melanoma, ovarian, prostate, pancreatic, bladder, lung and breast as well as others known to one of skill in the art. In other embodiments, these include but are by no means limited to cancers treatable with paclitaxel (Taxol), for example, ovarian, lung and breast as well as others known to one of skill in the art. In other embodiments, the type of cancer is selected from the group consisting of prostate, liver and melanoma.

As will be appreciated by one of skill in the art, an effective amount of G31P can also be used in the manufacture of a medicament or pharmaceutical composition for the treatment of a disease including but by no means limited to pulmonary disorders, inflammatory diseases and disorders, cancers and surgical/ischemia reperfusion applications. In these embodiments, the G31P may be combined with a suitable excipient or carrier and/or otherwise formulated so as to be in a suitable format for proper administration.

We had previously generated a bovine form of G31P, which was intended to be used for veterinary applications, but developed human G31P primarily in order to reduce as much as possible the likelihood that (human) subjects under G31P treatment would develop immune responses to the foreign (i.e., bovine) protein.

Figure 20:
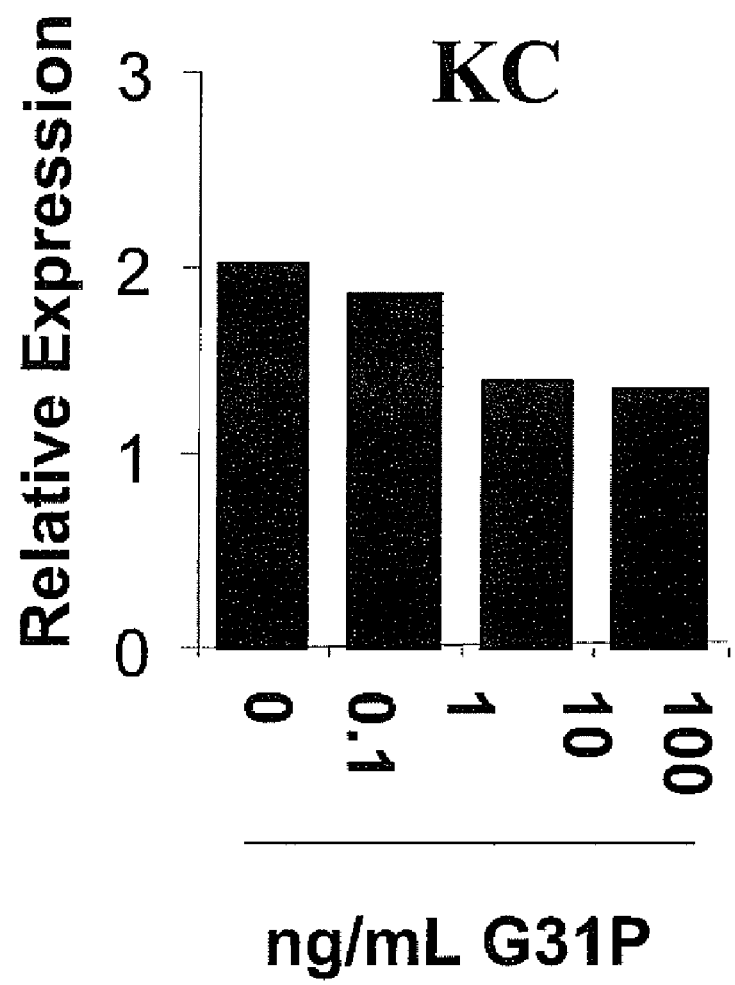
FIG. 20. G31P-treatment dampens ELR-CXC chemokine expression by B16 melanoma cells.
Figure 21:
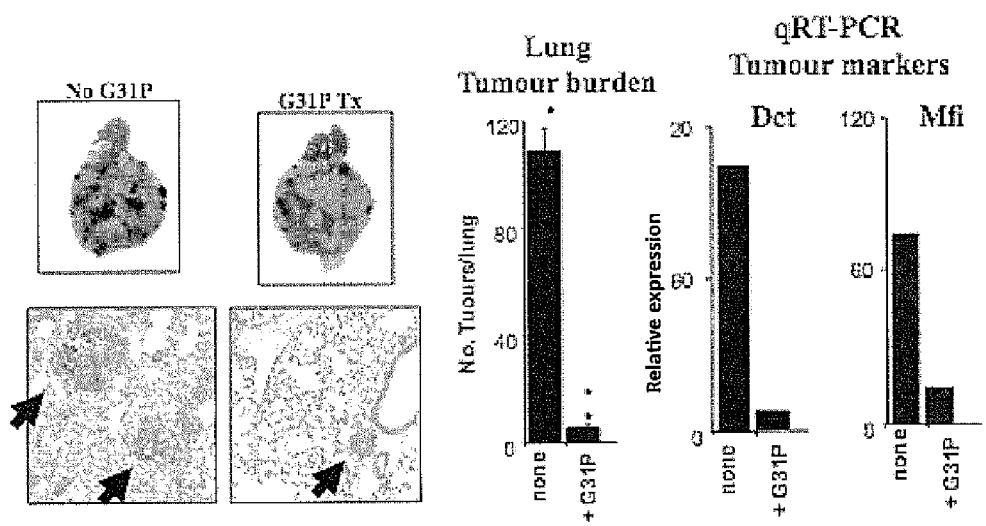
FIG. 21. G31P treatments reduce the development of melanoma metastases in a mouse i.v. B16 tumor cell model. C57BL/6 mice were challenged on day 0 with $1\times10^5$ B16-10 melanoma cells by lateral tail vein injection. Mice were then treated with 500 µg/kg G31P i.p. every second day commencing on day 0, 5, 10 or 15 (n=5). The cardiorespiratory tree of each animal was removed and photographed, then submitted for routine histopathology and mRNA extracted for qRT-PCR analysis of melanoma tumor marker expression, as noted. Mice were sacrificed on day 19 (*,,* $p>0.005$;**** $p>0.01$). The samples depicted are for those animals treated only with saline (no G31P or none) and those treated beginning on day 0 (G31P Tx or +G31P). Photomicrograph arrows point to histologically recognizable tumors.
Figure 22:
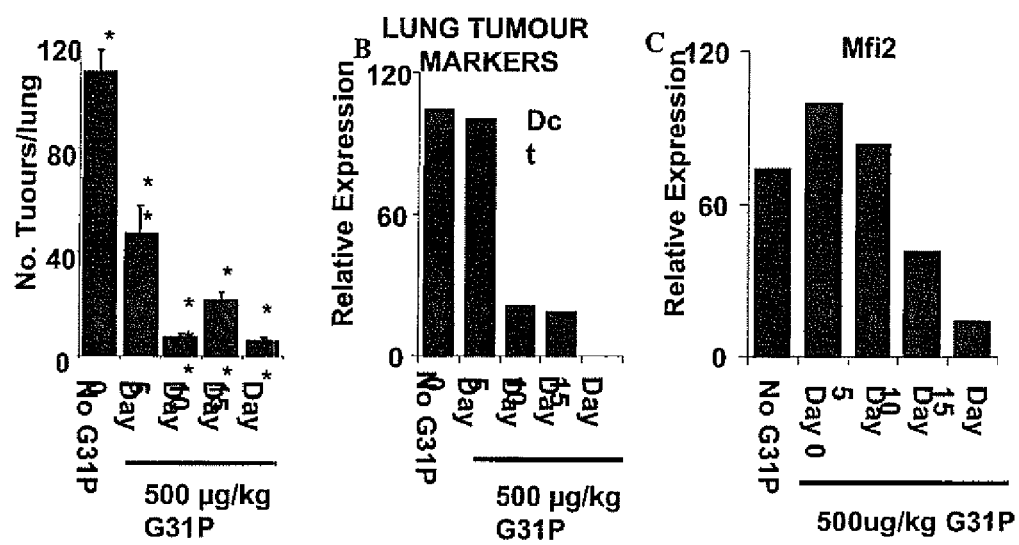
FIG. 22. In the mice from FIG. 21, (A) the numbers of discreet tumours on the pleural surface of the lung (±SEM) were counted. (B), (C) In addition, RNA was extracted from the lung tissue and qRT-PCR was used to detect the expression of the melanoma tumor markers tyrosinase-related protein (Dct) and melanoma-associated antigen p97 (Mfi2).
Figure 23:
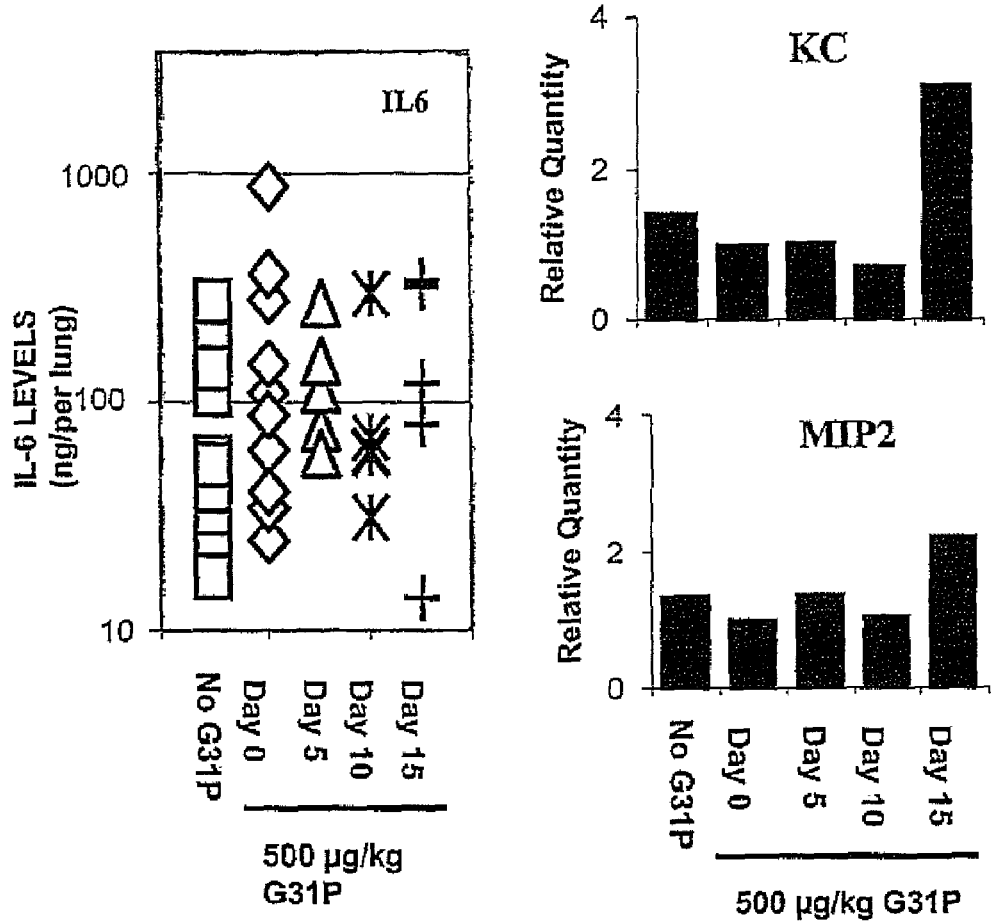
FIG. 23. Levels of IL-6 protein (left panel) and the relative levels of KC and MIP-2 mRNA (right panel) in homogenates of the lungs from the experiment in FIGS. 21 & 22. IL-6 levels were evaluated by ELISA, and mRNA levels by qRT-PCR, as in FIG. 22.

G31P treatments reduce tumor cell growth, and tumor metastasis and angiogenesis in a mouse melanoma tumor model. As noted, melanoma tumors express the CXCR1 and CXCR2, and employ ELR-CXC chemokines as growth, metastatic and angiogenic factors (Singh et al, 2010). Herein we established a mouse 616-10 melanoma tumour model in which we injected $1 \times 10^5$ 616-10 tumor cells intravenously, then treated the mice with either G31P (500 µg/kg, s.c.) or saline every second day for 21 days, when we sacrificed the mice. We documented first that the 616-10 melanoma cells express the CXCR2, are responsive to the ELR-CXC chemokine MIP2, and that G31P blocks that response (FIG. 19), as well as apparently autocrine ELR-CXC chemokine expression by these cells (FIG. 20). When the tumor cells were injected i.v., saline-treated mice developed large numbers of readily visible, and melanoma tumor marker (Dct and Mfi2)-positive tumors in their lungs, while the G31P-treated mice developed only a small fraction of that tumor burden (FIGS. 21 and 22). This therapeutic effect was not associated with discernible reductions in the lung levels of the cytokine IL-6, or the murine ELR-CXC chemokines keratinocyte-derived chemokine (KC) or macrophage inflammatory protein-2 (MIP-2)(FIG. 23). This data confirms that ELR-CXC chemokine antagonism had a marked therapeutic effect on melanoma cell lung colonization and tumor cell growth in this model.

G31P Treatments Reduce Tumor Cell Growth, and Tumor Metastasis and Angiogenesis in an Orthotopic Mouse Model of Human Prostate Cancer.

Figure 24:
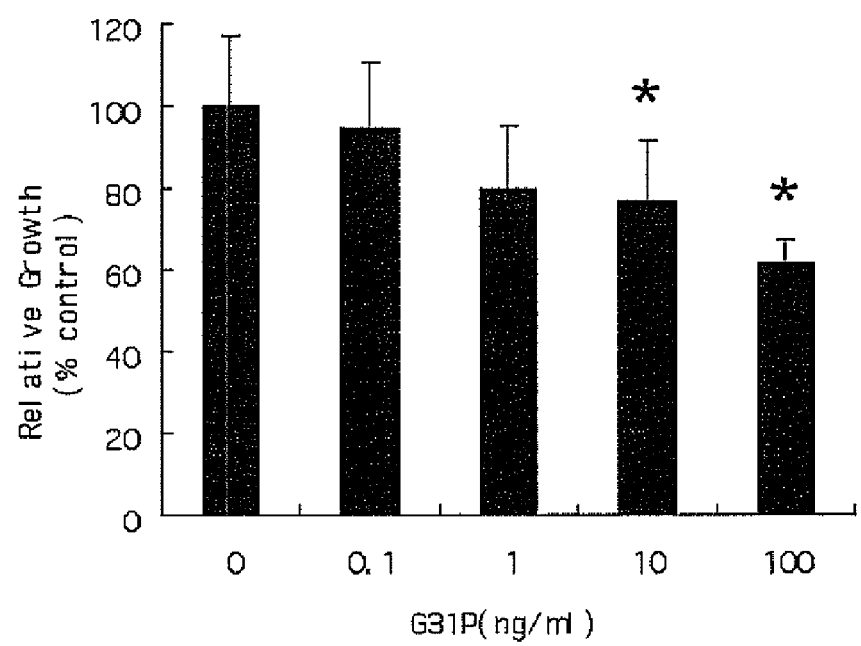
FIG. 24. G31P inhibits PC-3 cell proliferation. PC-3 cells ($5\times10^3$ cells/well) were cultured for 72 h with a concentration of G31P ranging from 0 to 100 ng/ml. After incubation, the cells' proliferation was determined using the Cell Counting Kit-8 assay. The graph represents the mean±SD values (n=3) of triplicate cultures (* $p<0.05$ vs. control).
Figure 27:
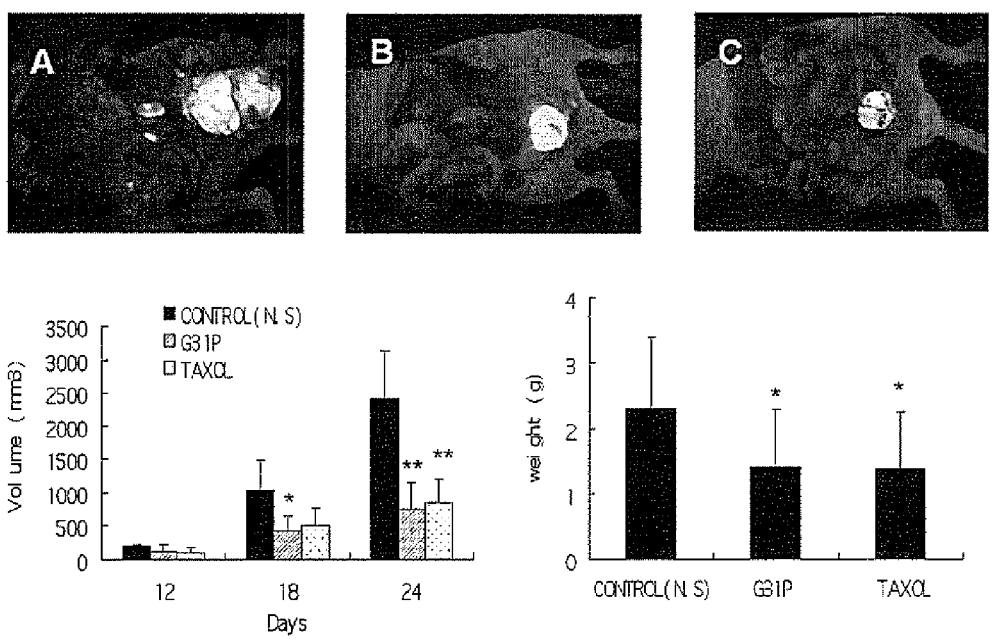
FIG. 27. G31P significantly inhibits PC-3-GFP tumor growth in nude mice. (A), (B) and (C) show fluorescence images of day 24 GFP-tumors in mice that received N.S., G31P and paclitaxel (Taxol), respectively. (D) Illustrates PC-3-GFP tumor volumes on day 12, 18 and 24. The graph represents the mean±SD values (n=18). (E) Illustrates the weights of day 24 PC-3-GFP tumors in mice that received N.S., G31P and paclitaxel, respectively. The graph represents the mean±SD values (n=18). (* p<0.05, * * P<0.01 vs. N.S control group).

It has been reported that the levels at which CXCL8 are expressed by prostate cancer PC-3 cells correlates well with the extent to which the cells develop into tumors, promote neovascularization, and metastasize following orthotopic implantation into nude mice (Kim et al, 2001, Neoplasia 3:33). As noted, CXCR1 and CXCR2 are expressed at high levels by PC-3 prostate cancer cells (Kim et al, 2001). The results described herein show that elevated ELR-CXC chemokine signaling confers a survival and proliferative advantage to prostate cancer cells in vitro and in vivo. Specifically, we found that blockade of such signalling by treatment with our ELR-CXC chemokine antagonist, G31P, at 10 or 100 ng/ml reduced the proliferation of PC-3 cells in vitro in a dose-dependent manner (40% reduction at 100 ng/ml G31P) (FIG. 24). In addition, our in vivo observations indicated that the growth of GFP-labeled tumors in nude mice was significantly reduced by G31P treatments, as determined by the day 24 tumour volumes and weights (P<0.01, versus the saline control group)(FIG. 27). Thus our data indicate that human G31P strongly inhibits the proliferation of the prostate cancer cells in vitro and in vivo.

Figure 25:
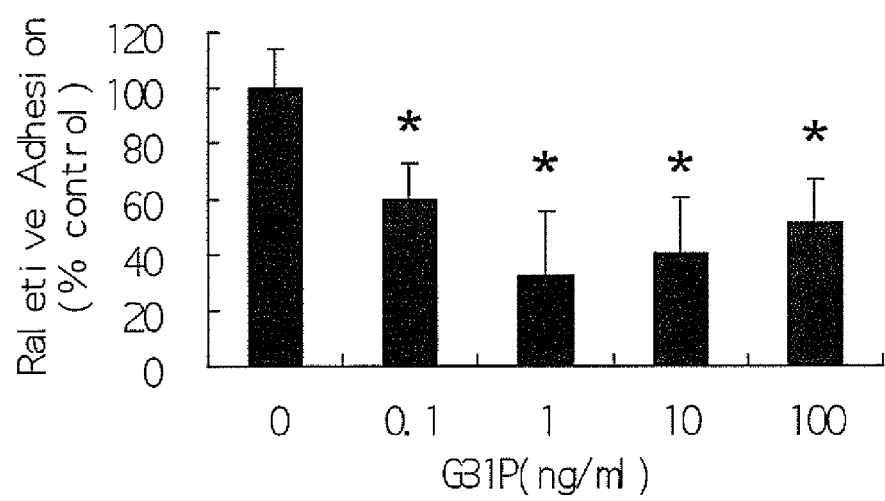
FIG. 25. G31P inhibits PC-3 cell adhesion. PC-3 cells were pretreated with a concentration of G31P ranging from 0 to 100 ng/ml for 24 h, then cells ($3\times10^5$ cells/well) were added to precoated 96-well plates and allowed to adhere for 1 h at 37° C. (5% CO2). The number of attached PC-3 cells was determined using the Cell Counting Kit-8 assay. The graph represents the mean±SD values (n=3) of triplicate cultures (* $p<0.05$ vs. control).

Tumor cell invasiveness and migration are important facets of tumor progression, and the ELR-CXC chemokines modulate adhesion, invasion, and migration of a variety of tumor cells. Our binding and wound modeling assays were used to assess adhesion and migration of PC-3 prostate cancer cells exposed to various concentrations (0, 0.1, 1, 10, 100 ng/ml) of G31P. We found that G31P significantly inhibited PC-3 cell attachment to ECM and in vitro migratory activity. At 1 ng/ml, G31P inhibited PC-3 cell adhesion by ≈65% relative to cells incubated without G31P, while at 10 or 100 ng/ml G31P 40% reduced the abilities of the PC-3 cells to migrate, as determined at either 48 h or 72 h (p≦0.05, versus control wells)(FIGS. 25 and 26).

Figure 28:
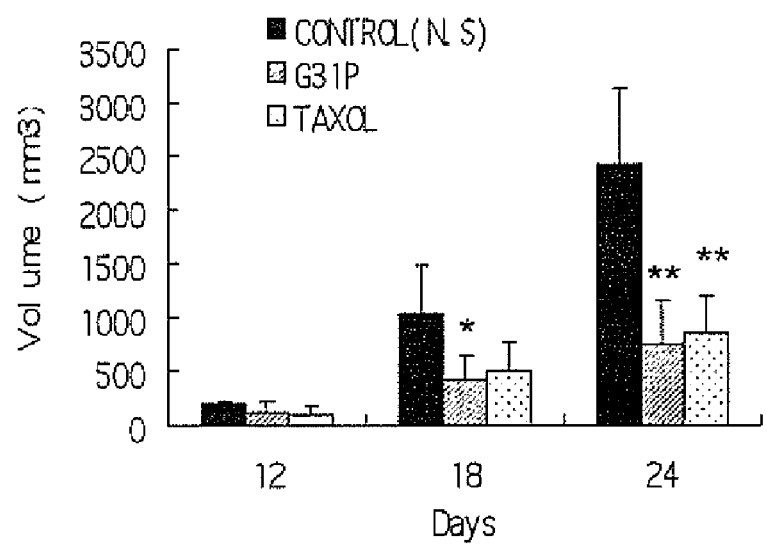
FIG. 28. G31P significantly inhibits PC-3-GFP tumor angiogenesis in nude mice. PC-3-GFP tumor microvessel density, as determined by image analysis of fluorescent images such as depicted in FIG. 27. The graph represents the mean±SD values (n=18) (* p<0.05 vs. N.S control group).

The ELR-CXC chemokines possesses many biologic functions beyond their well-recognized role in regulating inflammatory responses. In addition to being of particular relevance to tumorigenesis, CXCL1, -2, -3, -5, -6, and -8, at least, are potent mediators of angiogenesis, and do so through binding to the endothelial cell CXCR2 (Addison et al, 2000, J Immunol 165:5269). We assessed the impact of G31P on PC-3 tumor angiogenesis by measuring the microvessel densities in the fluorescent tumor masses using image analysis software. Our data demonstrates that the development of human prostate tumour microvessels was significantly suppressed in nude mice by G31P (P<0.05, versus the saline control group) (FIG. 28).

Figure 29:
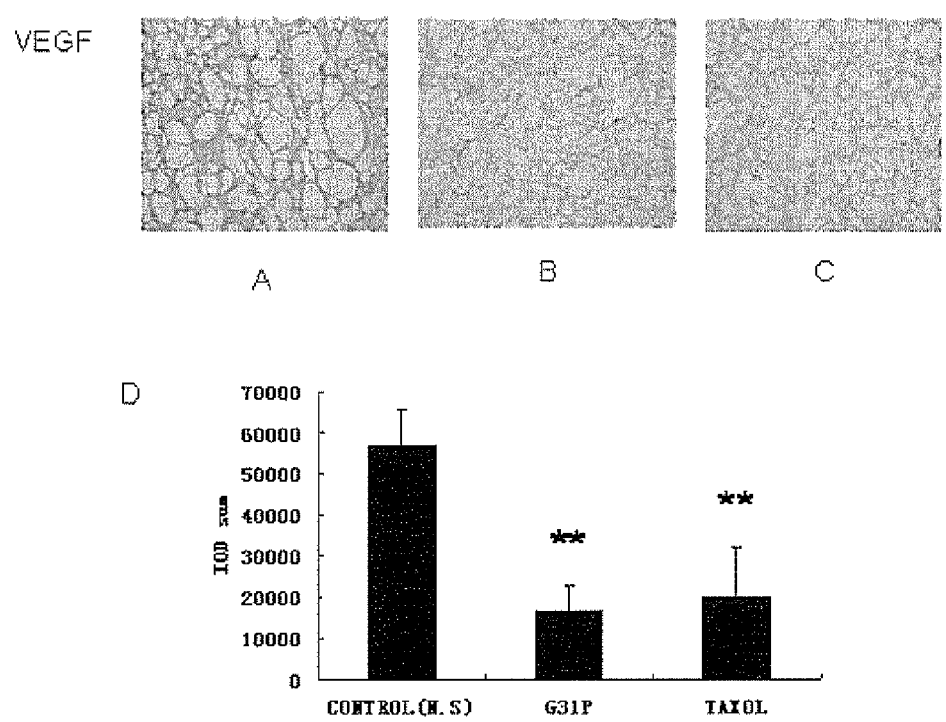
FIG. 29. Immunohistochemical analysis of VEGF expression on serial sections. (A), (B) and (C) show VEGF expression within day 24 tumours of mice that received N.S., G31P and paclitaxel, respectively (magnification, ×400). (D) Illustrates the integrated optical density (IOD) of VEGF cytoplasmic staining in the day 24 tumors. The graph represents the mean±SD values (n=10) (** p<0.01 vs. N.S control group).
Figure 30:
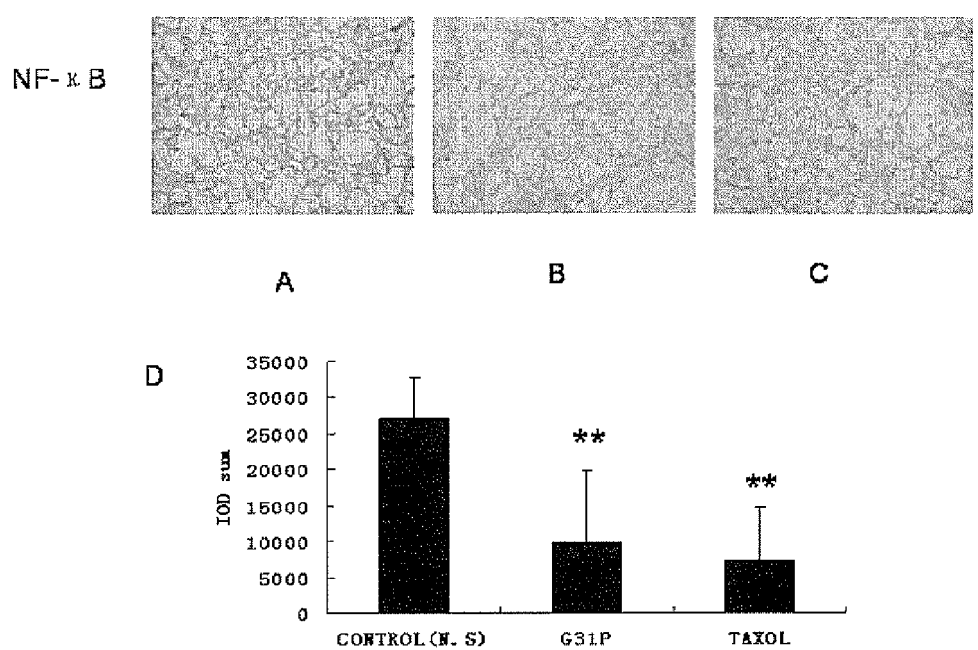
FIG. 30. Immunohistochemical analysis of NF-κB expression within day 24 tumours. (A), (B) and (C) show NF-κB expression within tumours of mice that received N.S., G31P and paclitaxel, respectively (magnification, ×400). (D) Illustrates the IOD values for NF-κB cytoplasmic staining within the tumors. The graph represents the mean±SD values (n=10) (** p<0.01 vs. N.S control group).

Numerous studies in vitro and in vivo have suggested that NF-κB plays important roles in regulating tumour cell proliferation, adhesion, invasion, angiogenesis and metastasis (Karin, 2006, Nature 441:431; Baud & Karin, 2009, Nat Rev Drug Discov 8:33; Wang et al, 2009, Cell Molec Immunol 6:327). Like the ELR-CXC chemokines, vascular endothelial growth factor (VEGF) is a NF-κB-inducible protein, and one of the most specific and potent angiogenic factors in the context of tumor-associated angiogenesis (Wang et al, 2009). VEGF is crucial for primary tumor growth, metastasis and angiogenesis. In addition, numerous reports have demonstrated that the metastatic potential of tumor cells correlates with the expression level of VEGF via NF-κB pathway activation and directly in prostate cancer as well as in other tumor types (Domenico et al, 2011, J Biomed Biotechnol doi: 10.1155/2011/947928; Ishigami et al, 1998, Br J Cancer 78:1379). Having said that, clinical use of VEGF inhibitors can actually increase tumor invasiveness and metastasis through induction of evasive mechanisms within the tumours (Loges et al, 2009, Cancer Cell 15:167). Our data confirms that G31P treatments were associated with reduced expression of both VEGF and NF-κB in PC-3 tumors (FIGS. 29 and 30). Thus, the demonstrated effectiveness of ELR-CXC chemokine antagonism via G31P in prostate and other cancer models suggests that its impact on VEGF expression may be only one of the mechanisms by which G31P acts. We have reported previously that it also dampens the inflammatory cycle through its effects on other cells (e.g., epithelial cells; Zhao et al, 2009, J Immunol 182:3213) which contribute important angiogenic and other factors Paclitaxel (Taxol), a well-known chemotherapic drug, has been shown to be effective as an anticancer agent in a variety of tumor types, including ovarian, prostate, lung and breast cancers (Ping et al., 2010, Urol Oncol: Sem & Orig Invest 28: 170-179). Treatment of tumor cells with paclitaxel interferes with the normal reorganization of the microtubule network during cell division and thereby inhibits cell proliferation. As discussed herein, we demonstrate that the volume, weight and angiogenesis of tumors in nude mice receiving either G31P or paclitaxel was significantly suppressed compared with the saline control mice. Fluorescent images of the GFP-PC3 tumour-bearing mice that were treated every second day with saline, G31P (500 µg/kg) or paclitaxel (15 mg/kg) were captured on days 12, 18 and 24 after tumour implantation and used to assess the tumour loads within the nude mice. The tumors of the G31P and paclitaxel treatment group animals were 5% smaller than those of the saline control mice at day 24 (FIG. 27A, B). Specifically, the tumor volumes were significantly reduced in the G31P-treated mice on days 18 (p≦0.05) and 24 (p≦0.01), while the paclitaxel treatments were associated with significantly smaller tumors only on day 24 (p≦0.01, versus the saline control group). These results were reflected also in our assessments of the tumor weights (FIG. 27C), wherein the G31P and paclitaxel treatments equally reduced the weights of the tumours recovered from the mice (p≦0.05, versus the control mice). There were no significant differences between the volumes or weights of the tumours recovered from the G31P and paclitaxel-treated groups (p>0.05). We also compared the impact of G31P and paclitaxel on tumor vascularization using image analysis of fluorescent tumors within the mice. As shown in FIG. 28, the tumor microvessel density of the G31P (p≦0.05) and paclitaxel (p≦0.05) group were smaller than that of saline control group. Again, there were no significant differences in the microvessel densities of the tumors within the G31P and paclitaxel group animals. Finally, we examined the impact of the two treatments on VEGF and NF-κB expression within the tumors. We found that the immunostaining pattern for NF-κB was nuclear and cytoplasmic, whereas VEGF displayed a predominantly cytoplasmic staining pattern. Representative photomicrographs of VEGF and NF-κB immunoreactivity are shown in FIG. 29 and FIG. 30, while quantitative image analysis (i.e., specific stain pixel densities) indicated that both G31P ($1.7 \times 10^4$ pixels) and paclitaxel ($2.0 \times 10^4$ pixels) significantly reduced VEGF staining relative to the saline-treated animals ($5.7 \times 10^4$ pixels; both, p≦0.01). Immunostaining for NF-κB assay revealed similar reductions in intensity of staining within tumors of the G31P-treated ($1.0 \times 10^4$ pixels) and paclitaxel-treated animals ($7 \times 10^3$ pixels) relative to saline-treated mice ($2.7 \times 10^4$ pixels; both, p<0.01). Taken together, this data confirms that G31P, like paclitaxel, is highly effective in the context of prostate cancer, although our data indicates that it is similarly effective in melanoma and hepatic adenocarcinoma models as well.

Referring to tables 1 and 2, as in FIG. 31, nude mice were implanted s.c. with a 1 mm³ slice of human PC3-GFP solid prostate tumor on day 0 and treated with 500 μg/kg G31P i.p. every second day commencing on day 0 (n=6). On days 19, 25, and 29 the sizes of the tumors were calculated from whole body images of the internal GFP-positive tumors and the mice sacrificed on day 29. The locations of the metastases were determined by direct observation for each group.

G31P treatments reduce tumor cell growth, and tumor metastasis and angiogenesis in a mouse model of hepatic adenocarinoma. In another experiment, P/L6 hepatocarcinoma (Hca-P/L6) cells were injected into the abdominal cavity of strain 615 mice (n=6). One group of mice was treated systemically with G31P (500 μg/kg) every day by subcutaneous injection on the back, for a period of 7 days, while the other group was untreated and was used as a control. All animals were killed on the 8th day, when the abdominal ascites fluids with suspended tumor cells were withdrawn from the peritoneal cavity of each mouse. As a measure of tumor progression in this model, we recovered ≈6 ml of ascites fluids from each untreated tumor-bearing mouse, but only ≈2 ml of ascites fluid the peritoneal cavities of the G31P-treated mice. FIG. 34 shows a comparison of numbers of tumor cells recovered in the ascites fluids of the two groups, as determined by direct counting. The samples from the G31P-treated mice contained $4.9 \times 10^6$ nucleated cells, while those of the untreated mice contained more than 3-fold more cells (i.e., $1.5 \times 10^7$ cells). Thus, here too G31P significantly inhibited tumor cell proliferation. As shown in FIG. 35, G31P treatments were associated with reduced viabilities among the recovered tumor cells, as determined by trypan blue dye exclusion criteria. Specifically, only 71% of the recovered ascites fluid cells were viable in the G31P-treated mice, while 92% of the recovered cells were viable in the untreated mice. This was reflected also in the physical appearance (i.e., shape) of the tumour cells recovered from the ascites fluids (FIG. 36), and was consistent with the G31P treatments inducing tumor cell apoptosis. Others have documented that CXCR1 or CXCR2 interference is associated with increased tumor cell apoptosis in melanoma cells (Sing et al, 2010), PC-3 prostate cancer cells (Shamaladevi et al, 2009, Cancer Res 69:8265) and adenocarcinoma cells (Varney et al, 2011). We also assessed the impact of G31P treatments on growth and metastasis of Hca-P/L6 tumor cells injected into the left hind foodpad of strain 615 mice (n=6). The mice were treated with saline or G31P (500 μg/kg, every second day). The mice were weighed and the volume of the footpad was determined every second day, and the animals were sacrificed on day 21. The histologic appearance of the injected footpads, and the size and appearance of the ipsi- and contralateral inguinal and axillary lymph nodes, as well as the para-aortic lymph nodes (as a measure of metastasis) were also assessed. The volumes of the footpads were significantly smaller in the G31P-treated mice compared to the saline-treated animals (p≦0.05), as were the diameters of the ipsilateral inguinal lymph nodes (p≦0.05), although there was no dramatic impact of the G31P treatments on the expression levels of the ELR-CXC chemokines KC or MIP-2, or CXCR2 in the ipsilateral footpads. Thus, the G31P treatments also had beneficial effects in the hepatic adenocarinoma model.

Neutrophils play important roles in ischemia and reperfusion (I/R) injury pathology. We also assessed the effects of an ELR-CXC chemokine antagonist, $CXCL8_{(3-72)}K11R/G31P$ (G31P), on neutrophil sequestration and local and distant organ injury after superior mesenteric artery I/R in rats.

The ELR-CXC chemokines also play important roles in neutrophilic inflammation. We report herein that a fully human ELR-CXC chemokine antagonist we have generated, $CXCL8_{(3-72)}K11R/G31P$ (G31P), has potent anti-inflammatory effects that arise through its actions at multiple levels. G31P inhibited CXCL8-induced chemotactic responses and intracellular $Ca^{2+}$ flux in CXCR1-transfected HEK cells and neutrophils, and responses of neutrophils to CXCR2-exclusive ligands. G31P desensitized heterologous G protein-coupled receptors (GPCR) on neutrophils, 52-86% reducing their $Ca^{++}$ flux and chemotactic responses to LTB4, C5a, and the bacterial tripeptide fMetLeuPhe. G31P also 60-90% blocked neutrophil chemotactic responses to mediators present in 10 of 12 sputum samples from cystic fibrosis or bronchiectasis subjects with bacterial pneumonia. Moreover, while A549 bronchial epithelial cells (which expressed CXCR1) secreted ≈29,000 pg/ml of CXCL8 in response to in vitro endotoxin challenge, G31P reduced this response by up to 98%, presumably by interrupting an autocrine inflammatory loop. The anti-inflammatory effects of G31P extended also to reversing the anti-apoptotic influence of ELR-CXC chemokines on neutrophils. That these effects were relevant in vivo was confirmed in a guinea pig model of airway endotoxemia, wherein G31P>95% blocked neutrophil infiltration into and activation within the airways, as determined by airway levels of the neutrophil primary, secondary and tertiary granule markers myeloperoxidase, lactoferrin, and matrix metalloproteinase (MMP)-9, respectively, and the epithelial cell marker MMP-2. These data suggest that the beneficial effects of ELR-CXC chemokine antagonism arise through effects that occur at multiple levels, including epithelial cells, neutrophils, and alternate GPCRs.

Aspiration pneumonia is a complication that occurs in head trauma and drug overdose victims and anaesthetized subjects during surgery. A high proportion of these people progress to acute lung injury or acute respiratory distress syndrome, in which neutrophilic inflammation drives the pathology. We report herein on the impact of blocking this neutrophil response by administration of an ELR-CXC chemokine antagonist, $CXCL8_{(3-72)}K11R/G31P$ (G31P). For this study, guinea pigs were anesthetized with ketamine (40 mg/kg) and xylazine (5 μg/kg) and administered 250 μl of acidified gastric contents (35 mg/kg body weight, pH 2.0), acidified sterile saline (pH 2.0) or normal saline via intranasal intubation. They were then given either saline or G31P (250 μg/kg body weight) subcutaneously. All animals were euthanized after 20 h. Bronchoalveolar lavage (BAL) was performed and airway total WBC, neutrophils and RBC were enumerated, and BAL fluid levels of the neutrophil degranulation markers myeloperoxidase (MPO) and lactoferrin (LF) were assessed as markers of neutrophil activation. The lung tissue levels of mRNA for the ELR-CXC chemokines CXCL1 and CXCL8 were determined by quantitative real-time PCR, and the airway burdens of bacteria were also assessed.

As discussed below, the saline-treated aspiration pneumonia animals had marked hemorrhagic consolidation across the pleural surface and the airways contained significant numbers of red blood cells. Their airways contained large numbers of neutrophils, consistent with the observed pulmonary expression of CXCL1 and CXCL8, and significant loads of Gram-positive and -negative bacteria. The G31P-treated aspiration pneumonia animals suffered only attenuated pulmonary vascular complications. Their airway and lung tissue neutrophilia was 90-95% reduced relative to the saline-treated, aspiration pneumonia animals ($p \leq 0.01$), as were the BAL fluid levels of MPO ($p \leq 0.01$) and LF ($p \leq 0.05$). Lung tissue CXCL1 and CXCL8 mRNA qRT-PCR signals were 50-95% lower in the G31P-treated animals. Despite the attenuated neutrophil responses, the numbers of bacteria recovered from the G31P-treated animals were 50% reduced relative to the saline-treated animals.

Previously, we have generated multiple forms of ELR-CXC chemokine antagonists, including bovine, human, and human-bovine chimeric isoforms (Li et al., 2001; Li et al., 2002; Xixing Zhao et al., 2007). Each of these takes on the form of an amino-truncated CXCL8 molecule with arginine and proline substitutions at amino acids K11 and G31, respectively. In vitro, each inhibits the responses of normal resting human neutrophils to human CXCR1 and CXCR2 ligands (e.g., CXCL1, CXCL5, and CXCL8), including intracellular $Ca^{++}$ flux, reactive oxygen intermediate production, and chemotaxis (Li et al., 2002; Xixing Zhao et al., 2007) as well as their anti-apoptotic activities. In addition, we have found that human $CXCL8_{(3-72)}K11R/G31P$ (G31P) also antagonizes intracellular $Ca^{++}$ flux and chemotaxis induced in neutrophils by ligands for heterologous G protein-coupled receptors (GPCR), including leukotriene B4, complement factor C5a, and bacterial tripeptide f-Met-Leu-Phe. In vivo, each of these antagonists can dramatically reduce pulmonary neutrophilic inflammation, hemorrhagic consolidation and pyrexia in guinea pigs suffering from airway endotoxemia (Gordon et al., 2005; Xixing Zhao et al., 2007) including, in the case of the bovine antagonist (the only one assessed in this way), when administered after the onset of symptoms (Gordon et al., 2005).

As discussed herein, we examined the ability of human $CXCL8_{(3-72)}K11R/G31P$ (G31P) to inhibit pulmonary inflammatory responses when guinea pigs were challenged via the airway with bacteria, as opposed to bacterial endotoxin alone. In this case the insult comprised bacteria in a highly acidic medium (pH 2.0 saline), and this combination has been used by others as a model of aspiration pneumonia. We observed inhibition by G31P of pulmonary neutrophil recruitment, hemorrhagic consolidation and ELR-CXC chemokine expression in response to the aspiration of these gastric contents, and we found that this G31P treatment did not negatively affect bacterial clearance by the innate immune system. Indeed, if anything, it appeared that bacterial clearance was augmented in the G31P-treated animals.

The accidental aspiration of gastric content is associated clinically with serious illness, including acute lung inflammation (ALI) and/or acute respiratory distress syndrome (ARDS), often with lethal outcomes, even for individuals under intensive care (Olsson et al., 1986; Fowler et al., 1983). Acute lung injury induced by acidic gastric contents is characterized by enhanced neutrophil sequestration and chemokine expression (Raghavendran et al., 2005) and others have reported that even sterile acidic solutions can induce lung injury associated with dramatic increases in IL-8 expression and neutrophil activation (Folkesson et al., 1995). It was interesting then that, in our model, instillation of 250 μl of pH 2.0 saline (pH2.0) did not lead to significant neutrophil sequestration or other pathology discernible using our approaches (Raghavendran et al., 2005; Folkesson et al., 1995). This may be because our challenge medium was not as acidic as that used by some others or comprised a smaller volume. Others have reported that solutions of $pH \geq 2.5$ and gastric contents volumes of <0.3 ml/kg body weight are required to develop lung injury (James et al., 1984, Anesth Analg 63:665-8; Exarhos et al., 1965, Dis Chest 47:167-9). We chose a pH of 2.0 and a dose of gastric contents of 35 mg/kg because, when combined, these parameters had led to very significant pathology in our preliminary experiments. This included dramatically elevated pulmonary neutrophil infiltration and hemorrhagic consolidation, which confirms that these parameter values were sufficient to adequately model aspiration pneumonia.

We have assessed the kinetics with which different neutrophil granule markers appear in the airways in endotoxemic animals, and found that the levels of primary (MPO) and secondary (LF) granule markers peaked at different times. Nevertheless, G31P effectively inhibited both in these animals. Herein we found that high levels of MPO could still be detected at 20 h after challenge with acidified gastric contents, while LF levels were not marked different in the aspiration pneumonia animals compared with the normal controls. However, both markers were significantly affected by the G31P treatment. The LF result could reflect the fact that LF is primarily an acute reaction phase product in aspiration pneumonia. In addressing the mechanisms by which G31P inhibited neutrophilic inflammation in this model, we assessed the pulmonary expression of the ELR-CXC chemokines CXCL1 and CXCL8 in our animals. It has been reported that, in a murine model of aspiration pneumonia, expression of macrophage inflammatory protein (MIP)-2 and keratinocyte-derived cytokine (KC) peaked at 6 h, though both were still elevated relative to normal controls at 24 h after challenge (Raghavendran et al., 2005). In our study, we detected elevated levels of CXCL1 and CXCL8 expression in our animals at 20 h, and G31P inhibited expression of both chemokines in aspiration pneumonia animals, which indicates that G31P had local effects on chemokine expression in the lungs. When we addressed the more systemic outcomes of the G31P treatments, we found apparently increased numbers of circulating neutrophils in the G31P-treated aspiration pneumonia animals relative to the saline-treated ones. This could be explained by G31P acting to prevent these cells from marginating in the pulmonary capillary bed under the influence of the inflammatory mediators (e.g., CXCL8) expressed in that compartment. We did find that the circulating cells of our G31P-, but not saline-, treated aspiration pneumonia animals were hyporesponsive to CXCL8, as noted previously in airway endotoxemia (Gordon et al., 2005).

In clinical settings, it is common to find Gram-positive cocci and Gram-negative bacilli in transtracheal samplings from aspiration pneumonia patients (Marik, 2001). These bacteria arise mainly from the nasopharynx or oropharynx, and enter the lung when people aspirate regurgitate (Marik, 2001). The volume, bacterial burden, and general condition of the individual's innate immune system correlate strongly with aspiration pneumonia pathology (Marik, 2001). In our model we instilled gastric contents intranasally, which would have effectively flushed the nasopharyngeal and tracheal flora directly into the lungs. We found that the G31P treatments did not increase the bacterial loads in the lungs of our animal. It had been reported that the inhibition of MIP-2 bioactivity in vivo impairs *Klebsiella pneumoniae* clearance in a mouse model, although the kinetics of the inflammatory response in that model and ours were quite different (e.g., they observed maximal MIP-2 expression at 48 h) (Standiford et al., 1996, J Leukoc Biol 59(1):24-8). In our system, bacterial clearance was not affected by the inhibition of neutrophil function, which may be because the bacteria we found in the lung BAL were mostly likely normal commensal bacteria from the nasopharynx or oropharynx, as opposed to *Klebsiella pneumoniae*, a pathogenic bacterium. Those normal respiratory commensals may become pathogenic only adventitiously (e.g., when confronting a compromised immunoinflammatory system).

Our data indicate that ELR-CXC antagonist, G31P, the effects of which have been previously characterized in airway endotoxemia, also functions effectively in aspiration pneumonia. Our results indicate that broad spectrum ELR-CXC chemokine antagonism is a useful approach in treating patients who have aspired regurgitates.

Sprague-Dawley rats were subjected to superior mesenteric artery 1 h ischemia/2 h reperfusion and treated with either saline or G31P (500 µg/kg, s.c.). Lung neutrophilia, and airway protein levels and RBC numbers were assessed, as was gut pathology. Expression of lung and jejunal inflammatory cytokines and chemokines, and jejunal myeloperoxidase (MPO) and matrix metalloproteinases (MMP)-2 and -9 were also determined.

We found that intestinal I/R led to a massive loss of integrity within the jejunal mucosa, accompanied by high-level local expression of MPO, MMP-2 and MMP-9. The lungs were markedly neutrophilic, while the airways contained high levels of protein and modest numbers of RBC. The G31P treatment significantly ≈70% reduced neutrophil accumulation in the lungs, ≈30% decreased airway protein levels, and ≈65% reduced accumulation of RBC. It also ameliorated loss of jejunal integrity, and reduced local MMP-2 (≈35%) and MMP-9 (≈78%) expression. I/R increased local expression of IL-6, GRO, MIP-2, and CINC-2α in the jejunum and increased pulmonary IL-1β, IL-10, and MIP-2 expression, and the G31P treatment modestly reduced expression of these as well.

These results suggest that ELR-CXC chemokine antagonism has significant protective effects against I/R-induced local and remote organ injury and G31P is a therapeutic tool for gut I/R injury.

Trauma-associated multiple organ failure (MOF) is a recognized sequel to intestinal ischemia-reperfusion (I/R) injury, and neutrophil sequestration is known to play a critical role in mediating both local and remote organ dysfunction (Schmeling et al., 1989; Cerqueira et al., 2005; Koike et al., 1993). Therapies for such MOF have focused on blocking neutrophil recruitment, with positive experimental outcomes being realized through antagonism of individual ELR-CXC chemokines. Simultaneous targeting of two of these chemokines (e.g. GRO and MIP-2) provides superior protection over targeting only one (Miura et al., 2001). On the other hand, antagonizing alternate neutrophil ligands (e.g. C5a, LTB4, and PAF) reportedly only partially inhibits neutrophil-mediated I/R injury (Souza et al., 2000; Arumugam et al., 2002, J Surg Res 103: 260-267; Souza et al., 2000, Br J Pharmacol 131: 1800-1808, 2000; Kohtani et al., 2002, Eur Surg Res 34: 313-320, 2002). Despite the reports of a critical role for neutrophils in intestinal I/R injury, there are reports that depleting circulating neutrophils before experimental induction of I/R injury does not reduce either local or remote organ injury (de Vries et al., 2003, J Immunol 170: 3883-3889, 2003), and that macrophage depletion instead substantially ameliorates such pathology (Chen et al., 2004, Gut 53: 1772-1780, 2004). Nevertheless, we observed very significant sparing of local and remote tissue injury by simultaneous blockade of all ELR-CXC chemokines.

We have generated multiple isoforms of the ELR-CXC chemokine antagonist, $CXCL8_{(3-72)}K11R/G31P$ (i.e., G31P) and each of these are equally effective in blocking human ELR-CXC chemokine-dependent neutrophil activation (bG31P, hbG31P, hG31P (Li et al., 2002, Biochem Biophys Res Commun 293: 939-944; Zhao et al., 2007, Int Immunopharmacol 7: 1723-1731, 2007)). In vitro, G31P antagonizes CXCR1 and CXCR2 ligand-induced intracellular $Ca^{2+}$ flux, ROI production and chemotaxis in neutrophils, as well as over-riding their anti-apoptotic influence on these cells. But G31P also dampens neutrophil activation (i.e., intracellular $Ca^{2+}$ flux, chemotaxis) induced by ligands for heterologous G protein-coupled receptors (GPCR), including those for LTB4, C5a, and f-Met-Leu-Phe. Also of relevance, G31P mitigates full activation of epithelial cells that are challenged with endotoxin, reducing their secretion of CXCL1, CXCL8, and IL-6, perhaps by interrupting an ELR-CXC chemokine-dependent autologous activation cascade. Interestingly, it has been reported that TLR4 is a critical element in I/R injury pathology (Wu et al., 2007, J Clin Invest 117: 2847-2859), which raises the question of whether G31P's protective effects could have been in part related to its ability to antagonize endotoxin-induced epithelial cell activation. It is known that epithelial cell apoptosis is prominent in intestinal I/R injury (Coopersmith et al., 1999, Am J Physiol 276: G677-686, 1999) and our histopathology data confirms that the intestinal epithelium suffered catastrophic damage in our I/R injury animals, but that the G31P treatment significantly ameliorated this.

G31P was developed to target neutrophils and, more specifically, their responses to ELR-CXC chemokines. As such, it dampens the pathologic outcomes of the neutrophilic inflammatory responses that are prominent in experimental airway endotoxemia (Gordon et al., 2005, J Leukoc Biol 78: 1265-1272), environmental pollutant exposure (Podechard et al., 2008, Toxicol Lett 177: 130-137), and aspiration pneumonia. Herein, we used a rat superior mesenteric artery (SMA) I/R model to examine the impact of ELR-CXC chemokine antagonism on intestinal I/R-induced local and remote organ injury. We found that G31P significantly blocked SMA I/R-induced neutrophil sequestration in the lung and modestly inhibited neutrophil marker MPO and its pathologic sequellae in the gut. Given that the jejunal tissues were so severely disrupted in our saline-treated I/R injury animals we were not able to assess neutrophil infiltration directly, but our surrogate markers (MPO, MMP-9) clearly suggested that they had been recruited. MPO is routinely used as a marker of neutrophil sequestration (Souza et al., 2004), although it would not differentiate between intravascular and extravascular neutrophils. Our data confirms however that ELR-CXC chemokine antagonism had a decided sparing effect on neutrophil recruitment from the vasculature into the lung tissues. Analogous effects on tissue MPO levels have been reported previously with the small molecule allosteric CXCR1/CXCR2 inhibitor, repertaxin (30 mg/kg), although it apparently is not active against alternate GPCR (i.e., LTB4 or fMLP) (Souza et al., 2004). We query whether G31P's effectiveness at the doses employed herein (i.e., 500 µg/kg) could be related to its ability to simultaneously block the CXCR11CXCR2 and heterologous GPCR.

Neutrophils have been confirmed to be critically involved in remote organ injury, e.g. lung (Chen et al., 2004, Gut 53: 1772-1780; Hernandez et al., 1987, Am J Physiol 253: H699-703), but their role in mediating gut injury in intestinal I/R injury is still uncertain (Chen et al., 2004; Hernandez et al., 1987; Simpson et al., 1993 Ann Surg 218: 444-453). We measured the gut tissue levels of the neutrophil tertiary granule marker MMP-9 as well as MMP-2 expression and found that the G31P treatments effectively inhibited both of these. Others have reported high level expression of MMP-9, largely in neutrophils, following intestinal I/R injury (Robinson et al., 2008, J Parenter Enteral Nutr 32: 433-438). They concluded that MMP-9 induction contributes importantly to I/R injury pathology. Our histological data indicates that intestinal I/R induced severe intestinal mucosal injury which was significantly attenuated by G31P treatment. This suggests that the neutrophils were causally involved in this injury, perhaps in part through release MMP-9. MMP-2 is a product of both leukocytes and resident cells such as fibroblasts and epithelial cells (Robinson et al., 2008; Lempinen et al., 2000, Eur Surg Res 32: 169-176). That G31P blocked its expression may provide further (circumstantial) evidence that this antagonist may act on neutrophils and other resident cells in this model system. We have already documented that G31P acts on bronchial epithelial cells, dampening their responses to bacterial endotoxin.

Marked expression of the inflammation-associated cytokines TNFα, IL-β and IL-6 has been reported previously in both local and remote organ tissues during I/R injury (Caty et al., 1990; Souza et al., 2004; Cuzzocrea et al., 1999, J Leukoc Biol 66: 471-480; Souza et al., 2001, Br J Pharmacol 134: 985-994). We observed little in the way of IL-1 or TNF expression in either the lung or gut in our animals, although IL-6 expression was strongly upregulated in the gut (but not lungs). Given that IL-6 reportedly facilitates TNFα and IL-1β production (Cuzzocrea et al., 1999), it is possible that our 2 h time-frame for reperfusion was too brief to allow significant upregulation of IL-1 and TNF. IL-6 is reportedly integral to loss of gut barrier function after hemorrhagic shock (Yang et al., 2003, Am J Physiol Gastrointest Liver Physiol 285: G621-629), and others have reported that anti-CINC antibodies significantly reduce circulating levels of IL-6 in such models (Kaneko et al., 2007). Our data confirms that intestinal I/R injury augments IL-6 expression in the gut, and that ELR-CXC chemokine antagonism can effectively decrease this IL-6 expression. This opens up the question of whether G31P's effects in maintaining jejunal integrity were related to its effects on IL-6. Expression of IL-10, an anti-inflammatory cytokine, was increased significantly in the gut and modestly so in the lungs of our I/R injury animals and the G31P treatments had marginal impact on its production in either compartment. It has been reported that blocking the ELR-CXC chemokines by either CXCR1/CXR2 antagonists or with anti-CINC-1 antibodies slightly increases lung, but not the gut, tissue IL-10 expression (Souza et al., 2004). However, other studies suggest that IL-10 does not play a significant role in protecting against intestinal I/R injury, but rather that it may exacerbate the tissue injuries (Stallion et al., 2002, J Surg Res 105: 145-152; Nussler et al., 2003, Ann Surg 238: 49-58).

Our results indicate that treatment with G31P, a CXCR1 and CXCR2 antagonist that also dampens responses across heterologous GPCR (i.e., C5aR, BLT1, FPR) on ELR-CXC chemokine receptor-positive cells, has potent effects on local and remote organ tissue neutrophil sequestration, and thereby protects against related tissue injury. This suggests that the approach of broadly blocking the ELR-CXC chemokines will be effective at preventing ischemia and reperfusion injuries in clinical situations.

We have shown that human G31P specifically blocks activation of neutrophils through the CXCR1 and CXCR2, and thereby their chemoattraction into inflammatory foci and expression of reactive oxygen intermediates (ROI). In engineering bovine G31P from its parent molecule, bovine CXCL8, our first step was to introduce high affinity into the molecule, which we did by amino terminal truncation and substitution of a lysine in place of Arg11 to generate bovine CXCL8(3-73)K11R (Li and Gordon, 2001). These arguments were in part based on prior work with human CXCL8 by Ian Clark-Lewis (Clark-Lewis et al., 1994, *J. Biol. Chem.* 269:16075-16081; Clark-Lewis et al., 1991, *J. Biol. Chem.* 266:23128-23134), although the bovine form of CXCL8(3-73)K11R appeared to have unexpectedly high agonist activity relative to its closest human counterpart (Li and Gordon, 2001). We next reduced the receptor signaling activity of this agonist by introducing a Gly residue in place of Pro31 to generate an antagonist that fortuitously had exceptionally high affinity relative to CXCL8 (Li et al., 2002). We hypothesize that it is this augmented receptor affinity that allows G31P to so effectively compete with native ELR-CXC chemokines for their receptors on neutrophils. It makes sense that G31P would operate via both the CXCR1 and CXCR2 because its parent molecule was CXCL8, a high affinity ligand of both receptors. Our data showing that G31P blocks CXCL8-dependent intracellular $Ca^{++}$ flux and chemotaxis in CXCR1-transfected HEK cells confirms unequivocally that G31P targets the CXCR1, and the fact that it blocks the activities of CXCL1 and CXCL5, which are exclusive CXCR2 agonists, similarly confirms its interactions with these receptors.

We also documented herein that G31P desensitizes heterologous GPCR in a quantitatively better fashion than CXCL8 (Blackwood et al., 1996), likely in part because of its high affinity interactions with the CXCR1 and CXCR2 (Li et al., 2002). Thus, G31P blocked both intracellular $Ca^{++}$ flux and chemotactic responses of neutrophils to signaling via CD88/C5aR1 (the C5a receptor), BLT1 (the LTB4 receptor), and Fpr1 (the fMLP receptor), although it was not as effective in desensitizing C5a-dependent $Ca^{++}$ flux as that associated with LTB4 or fMLP signaling. It has been reported that in responding to signals generated in inflammatory settings, neutrophils adopt a hierarchical response pattern, with responsiveness to agonists immediately responsible for recruitment from the vasculature (e.g., CXCL8, LTB4) being superceded as the cells traverse the blood vessel wall by responsiveness to those that would draw the cell to the pathogen itself (e.g., C5a, fMLP) (Heit et al., 2002, *J. Cell Biol.* 159:91-102). This effect is reportedly brought about by C5a- and fMLP-driven activation of MAPK in neutrophils, which dampens Akt activation, a critical event in responses to CXCL8 and LTB4. In the context of a bacterial infection, for example, this process would make a great deal of sense, since as the neutrophil moves into the tissues and towards the pathogen it must necessarily concentrate its resources on that target. In support of this, it had also been reported that while the fMLP and C5a receptors can cross-desensitize one another and the CXCL8 receptor, CXCL8 signaling cannot reciprocally desensitize $Ca^{++}$ flux or a number of other intracellular events downstream of the fMLP or C5a receptors (19, 20). At odds with this, however, is the report that while the CXCR2 cannot desensitize the CD88 or Fpr1, CXCR1 signaling can do so, albeit at significantly lower levels that that seen with C5a or fMLP-induced CXCL8 receptor desensitization (Richardson et al., 1998, *J. Biol. Chem.* 273:23830-23836). Also at odds is the report that CXCL8 signaling desensitizes neutrophil chemotactic responses to subsequent C5a or fMLP exposures (Blackwood et al., 1996). Our own data clearly indicated that G31P desensitizes neutrophil responses to fMLP, C5a, and LTB4, as noted likely related to high affinity interactions with its receptors. This could in part explain its effectiveness in dampening the pathology associated with airway endotoxemia in our model. It is known that endotoxin activates C5 to generate C5a (Smedegard et al., 1989, *Am. J. Pathol.* 135:489-497), and it seems reasonable to suggest that commercial endotoxin preparations such as we used would likely be contaminated with bacterial tripeptides (e.g., fMLP). Furthermore, given that LTB4 antagonism is of significant benefit in airway endotoxemia (Wollert et al., 1993, *Surgery* 114:191-198; Fink et al., 1993, *Crit. Care Med.* 21:1825-1837), it is also reasonable to suggest that this agonist would also have been present in our endotoxemic animals, although we did not assess this. This suggests that the neutrophilic pathology we observed could well be related to the combined effects of multiple agonists, including ELR-CXC chemokines, C5a, LTB4, and perhaps fMLP. We hypothesize that G31P's ability to ameliorate this pathology is attributable to its ability to not only block the CXCR1 and CXCR2, but also desensitize these other GPCR.

Another important finding in this study was that G31P also antagonized the responses of airway epithelial cells to bacterial endotoxin. Our data shows that A549 cells express the CXCR1, although epithelial expression of the CXCR1 or CXCR2 is not uniform. While unstimulated BEAS2B or colonic epithelial cells don't express the CXCR-1 or -2 (Dwinell et al., 1999, *Gastroenterol* 117:359-367; Farkas et al., 2005, *Chest* 128:3724-3734), epithelial cell lines from cystic fibrosis patients (IB3-1 and CFBE41o-) do express these receptors (Boncoeur et al., 2008, *Int. J. Biochem. Cell Biol.* 40:432-446). On the other hand, hypoxic Caco-2 and HT-29 bronchial epithelial cells express the CXCR1 (but not the CXCR2) and undergo chemotactic responses to CXCL8 signaling (Sturm et al., 2005, *Cytokine* 29:42-48). This could suggest that inflammatory signals upregulate expression of these receptors, but in A549 cells, at least, LPS stimulation does not alter their expression of the CXCR1 or CXCR2. The blockade of CXCL8 expression in LPS-stimulated epithelial cells by G31P led us to speculate that CXCR1 ligands are autocrine inflammatory mediators for these cells. It had been reported previously that CXCL8 is an autocrine growth factor for pancreatic tumour and melanoma cells but, as far as we are aware, this is the first demonstration that ELR-CXC chemokine expression can be a self-perpetuating event for epithelial cells. We also found that simple co-culture of quiescent human neutrophils with A549 cells strongly induced CXCL8 expression in these cultures and that G31P interrupts this response, dramatically reducing chemokine production. We did not determine which population of cells was activated in these co-cultures and therefore responsible for the cytokine expression. A number of mediators released from activated neutrophils (e.g, cathepsin G, elastase, defensins) can induce the release of CXCL8 from respiratory epithelial cells and, reciprocally, a number of epithelial products are neutrophil agonists (Khair et al., 1996, *Eur. Respir. J.* 9:1913-1922; Skerrett et al., 2004, *Am J Physiol Lung Cell Mol Physiol* 287:L143-152). Although neutrophils can be readily activated by the procedures used in their isolation (Link et al., 1997, *Clin. Hemorheol. Microcirc.* 17:175-180; Venaille et al., 1994, *Scand J Clin Lab Invest.* 54:385-391), when cultured alone neither the epithelial cells or neutrophils secreted substantial amounts of CXCL8, indicating that the interactions between these two cells were instrumental in their induction, and that endotoxin contamination of our culture medium by itself would not explain our observations. More importantly, G31P was able to interfere with these intercellular interactions sufficiently to ameliorate their influence on one another. The remarkable degree to which G31P dampened neutrophilic inflammation in our airway endotoxemic animals suggests that its ability to block the interactions between bronchial epithelial cells and those neutrophils that did find their way into the airways could be another integral component of its therapeutic effects.

Neutrophils are continuously generated in the bone marrow and released into the circulation at exceptionally high rates, which means of course that they need to be equally quickly disposed of if a homeostatic balance is to be maintained. Thus, neutrophils are pre-programmed to undergo apoptotic death quite rapidly, and this is only offset if inflammatory events dictate that there is an extended need for increased numbers of viable cells. A number of inflammatory mediators have anti-apoptotic effects on neutrophils, including the ELR-CXC chemokines, such that cells exposed to these mediators remain viable for extended periods of time and thereby can potentially contribute to the regional antimicrobial activities. This translates also into potential contributions to adventitious pathogenic processes, such that the ability of G31P to countermand ELR-CXC chemokine-driven anti-apoptotic effects would be of significant benefit to the host by virtue of encouraging functional removal of these cells from the inflammatory environment.

We had previously shown that bovine and a human-bovine chimeric form of G31P are effective in blocking neutrophilic pathology associated with airway endotoxemia (Gordon et al., 2005; Zhao et al., 2007), and we confirmed here for the first time that the human orthologue G31P was similarly effective. Herein we assessed the kinetics of neutrophil infiltration of the airways as well as their activation in situ in the lungs. Our data showed that G31P can dramatically reduce neutrophil recruitment and activation, inasmuch as we found high levels of the primary, secondary and tertiary granule markers myeloperoxidase (MPO), lactoferrin (LF), and matrix metalloproteinase-9 (MMP-9), respectively, in lungs of the saline-treated endotoxemic animals, but not in the G31P-treated animals. Previous studies have shown that a number of matrix metalloproteinases are present in the airways during experimental or clinical acute lung injuries or respiratory distress (D'Ortho et al., 1994, *Am J Physiol Lung Cell Mol Physiol* 266:L209-216; Fligiel et al., 2006, *Hum. Pathol.* 37:422-430), and we found both MMP-2 and MMP-9 in our BAL samples. While one might argue that the multiple gelatinases detected in our zymograms (i.e., 92 and 68 kD) could have been attributable to processing of high molecular weight MMP-9 to smaller forms, such processing of MMP-9 reportedly leads to generation of 86 and 82 kD gelatinases (i.e., not a 68 kD activity) (Ramos-DeSimone et al., 1999, *J. Biol. Chem.* 274:13066-13076). MMP-2 is expressed as a 72 kD zymogen that is processed to a 68 kD gelatinase (Growcott et al., 2006, *Respir Res* 7:9). MMP-2 is mainly produced by resident cells during acute lung injury, including for example type II epithelial cells or endothelial cells (Fligiel et al., 2006), such that the observation that G31B blocked its expression further supports our hypothesis that this antagonist acts not only on the neutrophil, but also on epithelial or other resident cells. Endothelial cells, another source of MMP-2, also express the CXCR2 (Reutershan et al., 2006, *J. Clin. Invest.* 116:695-702), so could potentially also fall under the influence of G31P.

Our data indicate that G31P is a potent antagonist of neutrophil activation induced by ELR-CXC chemokines. It targets not only the CXCR1 and CXCR2, but also heterologous GPCR (e.g., CD88/C5aR1, BLT1, and Fpr1) expressed on CXCR1- or CXCR2-positive cells, and it interrupts the autocrine epithelial cell inflammatory cascade triggered by bacterial endotoxins. Thus, the beneficial effects of G31P flow from its ability to simultaneously target multiple inflammatory processes. We speculate that the ability of G31P to antagonize heterologous GPCR may be a very important part of its anti-inflammatory activities, such that ELR-CXC chemokine antagonism in the absence of such activities (e.g., by anti-chemokine antibodies) may provide somewhat less effective protection. An obvious question to ask when one wishes to block neutrophil participation in biological responses is whether there are deleterious effects. For example, in bacterial pneumonia one might expect that these cells may be required for successful elimination of the pathogen(s). However, we have found that G31P very significantly attenuates pathology in aspiration pneumonia but at the same time does not reduce control of the microbial populations that enter the airways. Blocking neutrophil recruitment in bovine pneumonic pasteurellosis similarly improves outcomes very significantly (Slocombe et al., 1985, *Am. J. Vet. Res.* 46:2253-2258). We would predict based on our cumulative results that a broad array of inflammatory diseases would thus benefit from such ELR-CXC chemokine antagonism, as might other processes in which inflammation per se is not necessarily prevalent, but in which the ELR-CXC chemokines have nevertheless been implicated.

Human CXCL8$_{(3-72)}$K11R/G31P (G31P) treatment blocks pulmonary neutrophilic inflammatory responses following aspiration of gut contents. In preliminary experiments we optimized dosing of gastric contents to be used for the challenges, instilling 0, 5, 10, 20, 35, 50, or 75 mg/kg into the airways of each animal. At 20 h after challenge we harvested the animals and assessed their pulmonary hemorrhagic consolidation and airway leukocyte responses. The gastric contents dose-dependently induced pulmonary leukocytosis and hemorrhagic consolidation within the 5-35 mg/kg dose range. We also optimized the timing for induction of pulmonary pathology and the G31P treatment doses in this model. Based on this preliminary data, we established our model as delivery of 250 µl of gastric contents (35 mg/kg; pH2.0) intranasally to our animals, which we treated at the time of challenge with 250 µg/ml G31P and sacrificed 20 h later.

To critically assess the effectiveness of G31P in blocking aspiration pneumonia pathology, we used four groups of guinea pigs. The animals were challenged intranasally with pH 7.2 saline alone (Group1), pH 2.0 saline alone (pH=2.0, Group 2), or acidified gastric content (GC; groups 3 and 4), as described herein. Groups 1, 2, and 3 were treated s.c. with 1 ml of saline, while group 4 animals were given 250 µg/kg G31P. The acidified gastric contents induced strong pulmonary inflammatory responses (FIG. 1A-C), including airway and tissue neutrophilia ($p<0.001$ and $p<0.05$, respectively, versus pH 7.2 saline controls) and hemorrhagic consolidation. We observed little in the way of a pulmonary response following infusion of the acid-saline ($p>0.5$, versus pH 7.2 saline controls). The airway and tissue neutrophil responses of the aspiration pneumonia animals treated with 250 µg/kg G31P were reduced by 90% and 85%, respectively, relative to the saline-treated aspiration pneumonia animals (FIG. 1A, 1B), and the G31P treatment also reduced the airway RBC numbers to near background compared with the saline-treated aspiration pneumonia animals (FIG. 1C). The data indicate that 250 µg/kg G31P had a clear and potent protective effect against pulmonary neutrophilia and hemorrhagic consolidation induced by the aspiration of acidic gastric contents.

Figure 2:
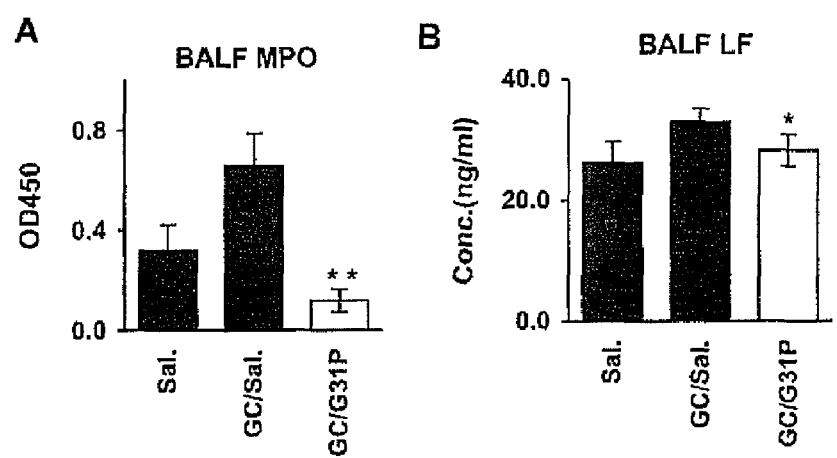
FIG. 2. $CXCL8_{(3-72)}$K11R/G31P also significantly decreased the appearance of neutrophil primary and secondary granules products in the airway. Neutrophil primary and secondary granules were assessed by measuring myloperoxidase (MPO) and lactoferrin (LF) using colorimetric assay and ELISA, respectively. (A) BAL from each animal was diluted and reacted with the colorimetric substrate TMB, and the developing reaction product was assessed spectrophotometrically, $OD_{450}$. The data were expressed as the mean $OD_{450}$ (±SEM). (B) Diluted BAL was also used to measure the secondary granule, LF using an ELISA assay. The data were expressed as ng/ml (±SEM). The data indicated that G31P significantly decreased MPO production ($p < 0.01$) and also LF ($p < 0.05$), though to a substantially lesser extent. Data shown in these figures are from one experiment that is representative of two experiments. *, $p < 0.05$ or **, $p < 0.01$, versus the saline-treated, GC-challenged animal values.

ELR-CXC chemokine antagonism significantly decreased airway neutrophil degranulation in aspiration pneumonia. Neutrophil degranulation is considered as a hallmark of neutrophil activation in inflammation, such that neutrophil degranulation markers (e.g., myeloperoxidase; MPO) are often used as surrogate markers of neutrophilic inflammation. Thus we measured the BAL fluid levels of MPO (a primary granule marker) and lactoferrin (LF; a secondary granule marker) in our experimental animals by colorimetric assay and ELISA, respectively. The G31P treatment of aspiration pneumonia animals dramatically reduced BALF MPO levels relative to the saline-treated pneumonic animals ($p<0.005$, FIG. 2A), although it had much less marked effect on BALF LF levels ($p\leq0.05$; FIG. 2B). These results demonstrated that neutrophil migration and activation were fully inhibited by G31P treatment.

Figure 3:
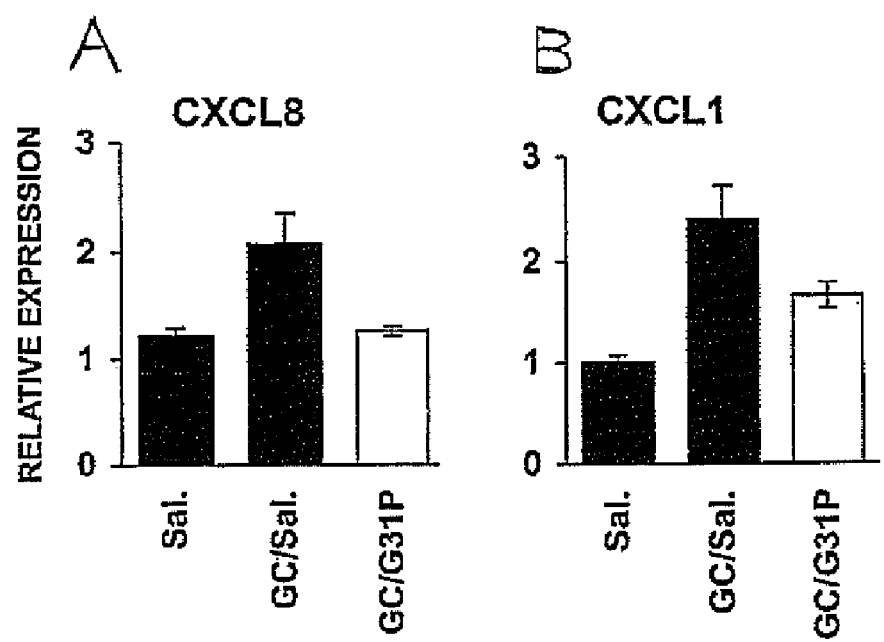
FIG. 3. $CXCL8_{(3-74)}$K11R/G31P can block ELR-CXC chemokine expression in aspiration pneumonia animals. Total RNA was purified from lung tissue of each animal and expression of the ELR-CXC chemokines, CXCL8 and CXCL1, was measured using quantitative real-time PCR (qRT-PCR), as described in the Materials and Methods. The data were expressed as the relative quantities of mRNA relative to a calibrator sample (a representative saline control group sample). The results indicate that the aspiration pneumonia animals expressed two-fold more CXCL8 (A) and CXCL1 (B) mRNA relative to saline-challenged aspiration pneumonia animals at 20 hours after GC challenge, and that G31P can block CXCL8 and CXCL1 mRNA expression by 90% and 50%, respectively.

G31P effectively blocked lung tissue ELR-CXC chemokine mRNA expression. We have shown that G31P treatment fully inhibited neutrophil activation and migration into lung tissue and airway caused by aspiration of gastric contents. We have recently found that G31P can partially block human bronchial epithelial cell ELR-CXC chemokine induction following challenge with bacterial endotoxin, and this was associated with decreased expression of matrix metalloproteinase-2 (MMP2), a primary product of activated epithelial cells. We wished therefore to know whether G31P treatments of aspiration pneumonia animals would reduce pulmonary expression of ELR-CXC chemokines and other inflammatory mediators, in addition to blocking neutrophil influx. Thus, we used quantitative real time PCR (qRT-PCR) to probe the lung tissues from our aspiration pneumonia and control animals for expression of CXCL8 and CXCL1 and the cytokines TNFα and IL-1β. We found that even at 20 h after the gastric content challenge, CXCL8 and CXCL1 mRNA levels were still expressed at levels two-fold greater than in saline-challenged (i.e., normal control) animal (FIGS. 3A, B). Interestingly, G31P treatment reduced lung expression of CXCL8 at this time to near background and CXCL1 expression by 50%, relative to the saline control animals (FIG. 3A, 3B). However, the levels of TNFα and IL-1β were indistinguishable between the saline-challenged and aspiration pneumonia animals (i.e., were at background) at this time, such that the G31P treatment had no discernible effect on the expression of these cytokines. These results indicate that G31P treatment did block ELR-CXC chemokine expression in the inflamed lung tissues following aspiration of acidified gastric contents.

Figure 4:
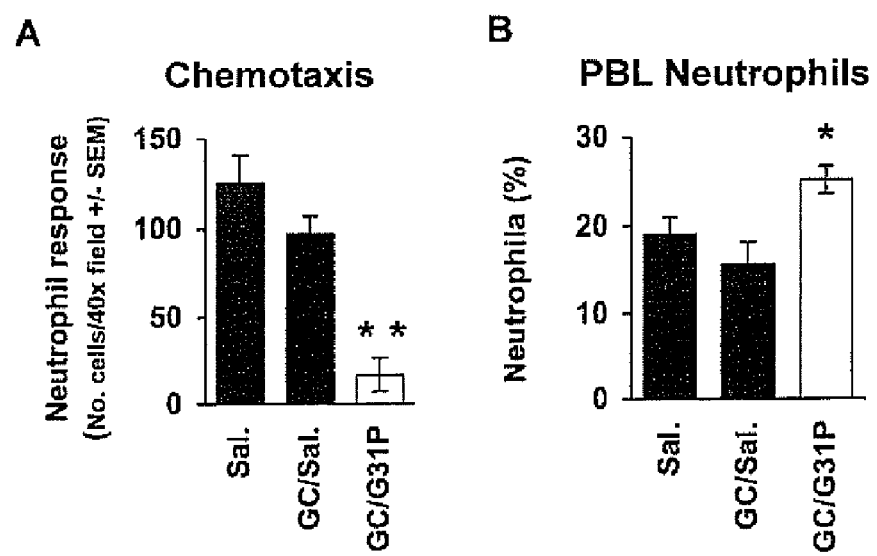
FIG. 4. $CXCL8_{(3-74)}$K11R/G31P blocks chemotactic responses of guinea pig neutrophils to CXCL8. As described above, guinea pigs were challenged with saline or GC (+/−G31P) and sacrificed 20 h later, as in FIG. 1. (A) Differential counts were performed on the blood WBC from each group of animals and the proportions of neutrophils enumerated. The data were expressed as the mean percentage of WBC that were neutrophils (±SEM). The data indicate that hG31P treatment modestly increased the proportion of circulating neutrophils in the blood. (B) Neutrophils were purified from the peripheral blood of each animal and used in modified Boyden chamber microchemotaxis assays in which saline or 10 ng/ml human CXCL8 was the chemoattractant. Each sample was assessed in duplicate, and the responses assessed by counting the number of cells within five 40× objective microscope fields of the stained chemotaxis membranes. The data were expressed as the number of cells (experimental minus control) per 40× field (±SEM). The neutrophils from the G31P-treated animals (GC/G31P) were significantly less able to respond to CXCL8 than those from the saline-treated (GC/Sal.) or normal (Sal. $p < 0.01$) animals. The data presented are from one experiment that is representative of two experiments. *, $p < 0.05$ or **, $p < 0.01$, versus the saline-treated, GC-challenged animal values.

Neutrophils from G31P treated animals are hyporesponsive to CXCL8 stimulation in vitro. While G31P blocked ELR-CXC chemokine expression in the lungs of our experimental animals, we would predict based on earlier studies (Gordon et al., 2005) that, even if exposed to these chemokines in vivo, the circulating neutrophils of the G31P-treated animals would be incapable of responding and moving into the tissues. To test this, we purified peripheral blood neutrophils from each animal and assessed their ability to respond to CXCL8 in chemotaxis assays. As shown in our airway endotoxemia model (Gordon et al., 2005), these cells from the G31P-treated aspiration pneumonia animals were indeed hyporesponsive to CXCL8 (FIG. 4A; $p<0.01$, relative to either the normal control or saline-treated aspiration pneumonia animals). This suggested that G31P had occupied the CXCL8 receptors (i.e., CXCR1 and CXCR2) on the circulating neutrophils in these animals, preventing them from responding to CXCL8 after purification. In addition, we also assessed the impact of the various treatments of our animals on their circulating neutrophil numbers. We enumerated the circulating neutrophils of our animals, and found that G31P-treated animals showed significantly increased numbers of neutrophils (FIG. 4B) relative to the saline-treated aspiration pneumonia animals, although these animals did not display a neutropenia relative to the normal control animals. Others have reported though that surgical anaesthesia can induce a mild neutropenia in healthy control animals (Morisaki et al., 1998, Br J Anaesth 80:502-3).

Figure 5:
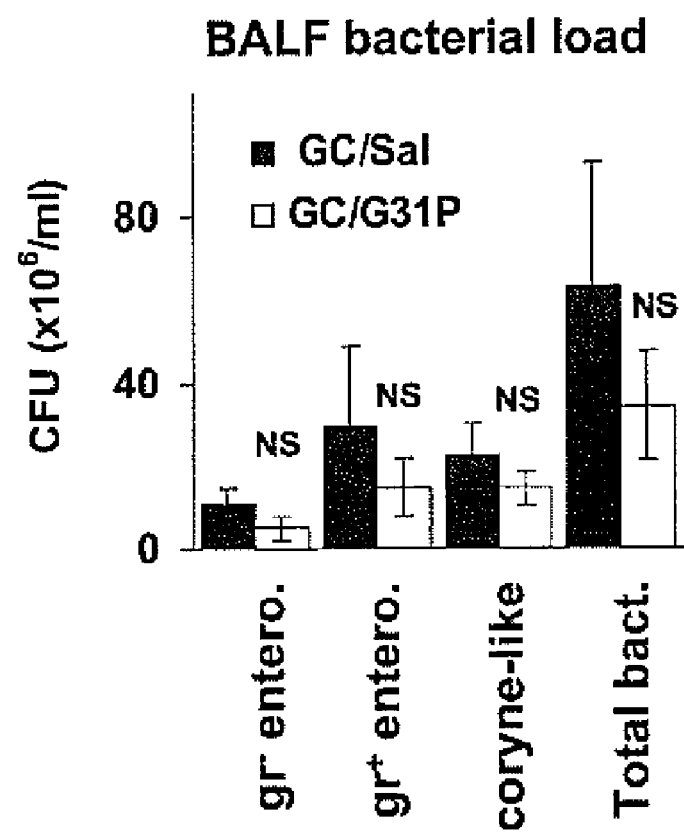
FIG. 5. Neutrophil blockade did not negatively increase bacterial growth after $CXCL8_{(3-72)}$K11R/G31P treatment. Aspiration pneumonia was induced in guinea pigs as in FIG. 1. BAL fluids from each animal were diluted 1:250 and cultured overnight on blood agar plates. The bacteria colonies that developed were differentiated and counted. The data are expressed as the number of colonies $(\times 10^6)$ per ml BAL. The results show that three primary groups of organisms, including gram-negative enterobacilli (G[−] enter rod, gram-positive enterobacilli (G[+] non-enter rod), and gram-positive corynebacterium-like (G[+]corynebacterium), were cultured from the BAL. The G31P treatment did not increase the bacterial load in the aspiration pneumonia animal ($p > 0.05$). This data is from one experiment that is representative of two experiments performed.

G31P mediated neutrophil blockade did not increase bacterial growth in the lungs of aspiration pneumonia animals. Given the roles of neutrophils in anti-bacterial defenses, a critical element of this investigation was whether neutralization of the pulmonary neutrophil response with G31P would predispose the animals to development of runaway airway bacteremia. Thus, we assessed the bacterial loads in the BAL fluids of our experimental animals, grossly differentiating the BAL flora as gram-negative or—positive enterobacilli, or gram-positive *corynebacterium*-like organisms. For each of these bacterial groups, the saline-treated aspiration pneumonia animals had higher loads than the G31P-treated animals (FIG. 5), suggesting that neutrophil blockade did not negatively affect bacterial clearance in this model.

Figure 6:
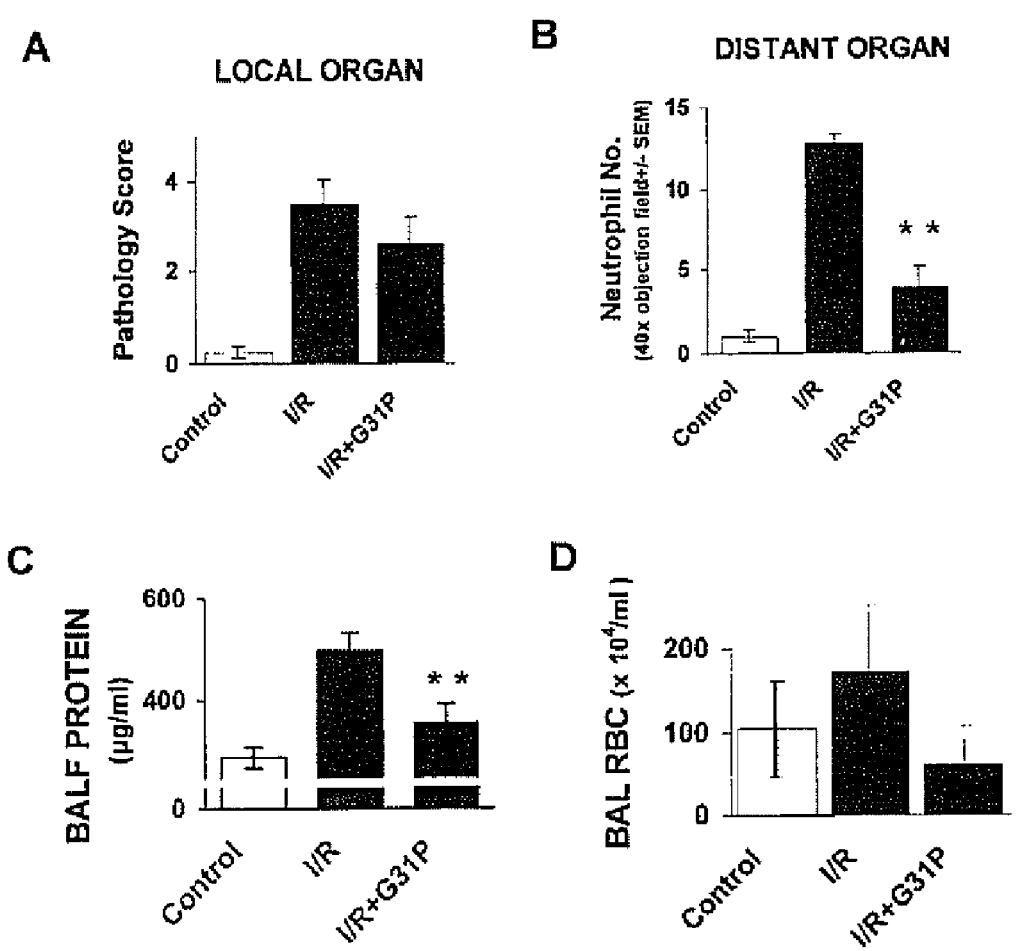
FIG. 6. G31P can prevent local (gut) and remote (lung) tissue injury after superior mesenteric artery ischemia and reperfusion. Ischemia-reperfusion injury was induced in male Sprague-Dawley rats (n=5/group) by total occlusion of the superior mesenteric artery (SMA) for 1 hour followed by reperfusion for 2 hour. At this time sham-surgical rats (control), saline-treated ischemia-reperfusion animals (I/R), and G31P-treated I/R animals were sacrificed. (A) The gross levels of jejunum (local organ) pathology was determined by direct examination of the gut tissues (hemorrhage, edema), as noted in the Material and Methods. (B) The numbers of neutrophils present in lung tissue sections were enumerated by direct counting at 400× power, while in (C) and (D) the bronchoalveolar lavage fluid (BALF) levels of protein (μg/ml) and red blood cell (RBC) numbers were assessed by protein microassay and direct counting as surrogate measures of pulmonary vascular leakage. The mesenteric I/R dramatically augmented gut pathology, neutrophil infiltration of the lung tissues, and loss of vascular integrity in the lungs, and the G31P treatments significantly reduced these effects. The result is representative one of two independent experiments. **, $p \leq 0.01$, relative to the saline-treated I/R-operated rats.
Figure 7:
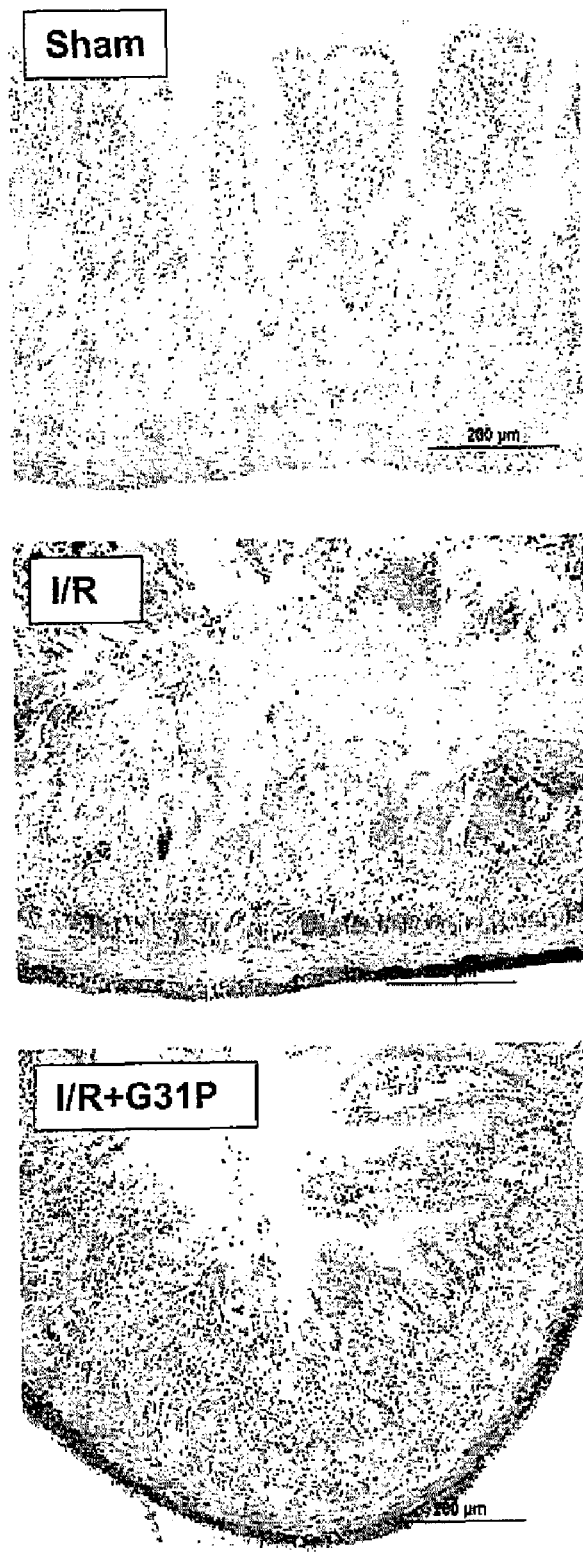
FIG. 7. Photomicrographs of the jejunal injury in sham-surgical and saline- or G31P-treated I/R injury animals. The jejunal tissues from the animals in FIG. 6 were processed to paraffin sections, stained with a standard H&E stain, and representative sections photographed. The sham surgery animals did not suffer any appreciable jejunal pathology (upper panel). On the other hand, the villi and crypts of the I/R animals suffered massive loss of integrity (middle panel), and G31P treatment had very significant sparing effects on this I/R-I-induced mucosal and crypt erosion (lower panel). Original magnification ×200.

The superior mesenteric artery ischemia/reperfusion injury model in rats. We surgically induced intestinal ischemia for one hour by ligature of the superior mesenteric artery (SMA), and then removed the clamp to allow reperfusion of the affected tissues. A vascular clamp was set in place around the artery also for one hour in the sham I/R injury animals, but not tightened to occlude blood flow. Two hours after surgical closing of the abdominal cavity we assessed the impact of these challenges on the animals (FIG. 6). On gross examination, the jejunum of the sham I/R injury animals was a healthy pink colour, firm and largely empty of contents (pathology score, 0.3). On the other hand, the jejunum of the I/R injury animals was dark red-purple in colour and edematous, fragile to the touch, and contained a substantial volume of bloody fluid (pathology score, 3.5). Histologically, the mucosal epithelium within the jejunum of the sham I/R injury animals was intact, as were the villi, while the jejunal epithelium of the saline-treated I/R injury rats were entirely destroyed (FIG. 7). The damage to the villous processes of the I/R injury animals extended deep into the crypts such that very little villous architecture remained. There were no inflammatory cells within the lamina propria of the sham-surgical animals. The residual lamina propria of the I/R injury animals contained modest numbers of necrotic inflammatory cells and these appeared also within the amorphous contents of the gut lumen.

On gross examination of the remaining organ systems of our animals, we found that in the I/R-injury animals the pleural surface of the lungs appeared slightly hyperemic, but otherwise healthy, while all other organ systems appeared healthy. We did bronchoalveolar lavages (BAL) on each animal and found few neutrophils in the BAL fluids of the SMA I/R-injury animals (~1% of WBC). However, significant numbers of neutrophils were found in lung tissues of the I/R-injury, but not sham surgery animals ($p \leq 0.01$; FIG. 6B). As a further assessment of the extent of pulmonary involvement in SMA I/R injury pathology, we also assessed transcapillary vascular leakage in the lungs, using BAL fluid protein levels and red blood cell (RBC) numbers as surrogate markers. We found significantly more protein in the BAL of the experimental animals than the sham surgical controls ($p \leq 0.01$; FIG. 6C) and also increased numbers of RBC (FIG. 6D).

ELR-CXC chemokine antagonism ameliorates local and distant organ pathology in SMA I/R injury. A large number of inflammatory mediators have been implicated in I/R injury pathology, including the ELR-CXC chemokines (Caty et al., 1990; Sekido et al., 1993; Miura et al, 2001). For that reason we tested the impact of broadly antagonizing the ELR-CXC chemokines expressed in our I/R injury animals by systemic delivery of $CXCL8_{(3-72)}K11R/G31P$ (G31P). 031P treatment at the time of ischemia induction had a sparing effect on loss of jejunal integrity induced by I/R injury. The extent of the gross jejunal pathology, as determined by the tissue edema, discolouration, and the lumen contents, was modestly lower in the G31P-treated animals (pathology score, 2.6) compared to the saline-treated I/R injury cohort (FIG. 6A). Histologically, in contrast to the saline-treated I/R injury animals, much of the mucosal epithelium and villous architecture in the G31P-treated animals was intact, although the tips of some villi were damaged and the lumen contained modest amounts of amorphous material (FIG. 7).

Figure 8:
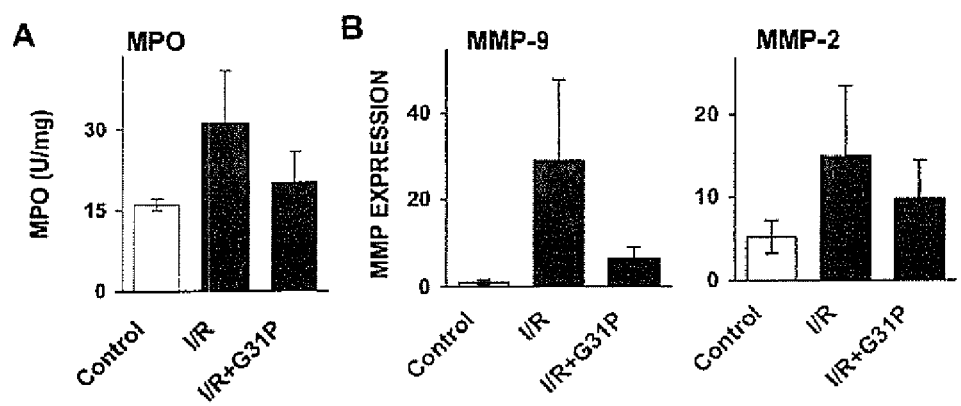
FIG. 8. G31P treatments modestly ameliorate local neutrophilic inflammation in I/R injury animals. The jejunal tissues of the animals in FIG. 7 were homogenized and the levels of neutrophil myeloperoxidase (MPO) and matrix metalloproteinase-9 (MMP-9), as well as MMP-2 were assessed by colorimetric assay (MPO) and gel zymography (MMP-9 and MMP-2). MPO and MMP-9 were employed as surrogate measures of neutrophil influx into these tissues, the integrity of which was almost completely compromised. All three markers were increased in the I/R injury animals and G31P treatment reduced each of them. The MMP-9 and -2 levels are presented as relative units. The result is representative one of two independent experiments. **, $p \leq 0.01$, relative to the sham-surgical animals.

As the jejunal mucosa and crypts were largely destroyed by the I/R injury in the saline-treated group, we were unable to directly assess neutrophil involvement in this pathology. We therefore assessed the levels of myeloperoxidase (MPO) and matrix metalloproteinase-9 (MMP-9), markers of neutrophil primary and tertiary granule release, respectively, within the gut tissue. The results show that the levels of these two markers increased in the jejunal tissues of the I/R injury animals (FIGS. 8A, B) and that the G31P treatment reduced the levels of both by 70-80%. We also assessed the levels of MMP-2 (a product of activated epithelial cells), and found that I/R injury induced a three-fold increase of the levels of MMP-2 in the gut, while the G31P treatment reduced its expression by ≈50% (FIG. 8B).

Figure 9:
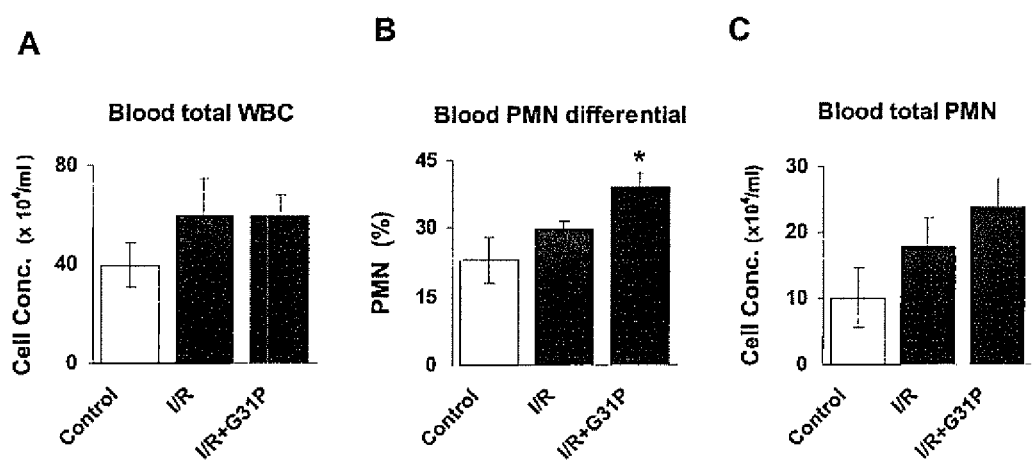
FIG. 9. Impact of G31P treatments on circulating neutrophils in I/R injury animals. Peripheral blood from the animals in FIG. 6 was obtained and (A) the numbers of white blood cells (WBC)/ml blood were determined by direct counting using a hemocytometer. Blood smears were generated from this blood and stained with Wright's solution, then (B) the proportion of neutrophils in the WBC were determined by direct counting, and (C) the total blood neutrophil counts calculated using this data. The data are expressed as the mean number of WBC, percent neutrophils, and numbers of neutrophils (±SEM), respectively. The data indicate that G31P treatment did not change total WBC, but slightly increased total neutrophils in the blood versus saline treatment led to a significant increase in the proportion of circulating neutrophils. These results are from one experiment that is representative of two. *, $p<0.05$, versus the saline-treated, I/R-injury animals.

Antagonizing the ELR-CXC chemokines also had protective effects on the distant organ pathology in our animals. The numbers of lung parenchymal neutrophils was ≈70% lower in the G31P-treated animals than in the saline-treated I/R injury animals ($p \leq 0.01$; FIG. 6B). And this reduction in inflammatory cell involvement in the G31P-treated animals was reflected by a similar reduction in transcapillary vascular leakage (BAL fluid protein levels and RBC numbers; FIGS. 6C and 6D). Compared with the levels of MMP-9 and -2 in the jejunum, there were very low levels of these two gelatinases in the lung tissues, such that the zymogram signals were not easily discernible. We also assessed whether I/R injury led to a peripheral neutrophilia in our animals, but found that the total WBC and neutrophil counts were not significantly elevated in the I/R injury animals (FIG. 9A, 9B, 9C). We did however observe a significant increase in the percentage of circulating neutrophils in the G31P-treated I/R injury animals, relative to the saline-treated I/R injury animals (FIG. 9B). Taken together, our data confirm that distant organ involvement was a significant event in our model of SMA I/R injury and that ELR-CXC chemokine antagonism significantly reduced this pathology.

Figure 10:
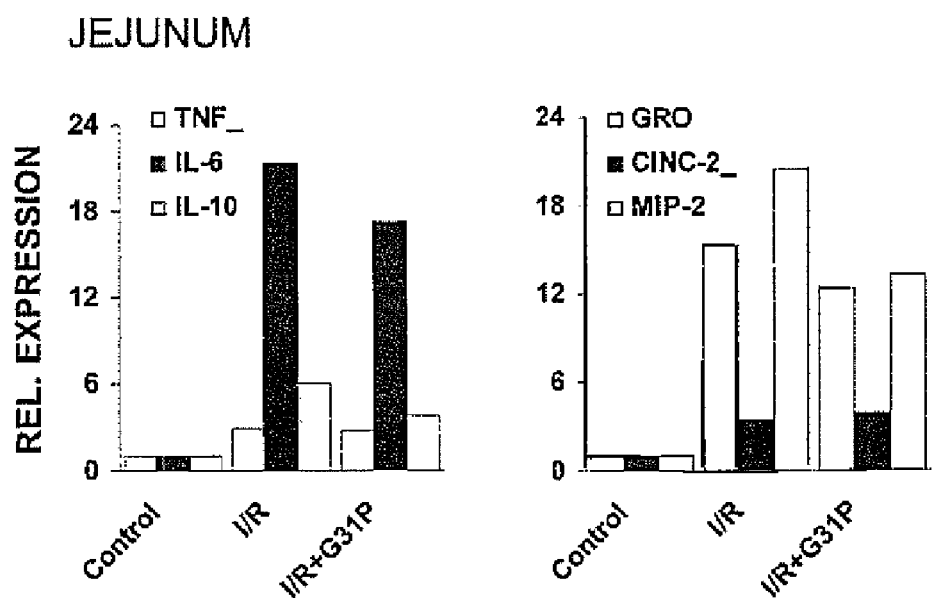
FIG. 10. Effect of G31P treatments on expression of proinflammatory cytokine and chemokine in I/R injury gut tissues. Jejunal tissues obtained as in FIG. 8 were also processed for total RNA extraction, and the levels of TNFα, IL-β, IL-6, IL-10, GRO, CINC-2α, and MIP-2 expression were assayed by qRT-PCR, as in the Materials and Methods section. The data are expressed as the relative quantities of mRNA relative to a calibrator sample (a representative sham surgical group sample). The results indicate that I/R injury differentially increased expression of TNFα, IL-6, IL-10, GRO, MIP-2, and CINC-2 relative to the sham-surgical animals. The G31P treatments can modestly reduced IL-6 and IL-10, as well as GRO expression and more effectively reduced MIP-2 expression. These results are from one experiment that is representative of two independent experiments.

ELR-CXC chemokine blockade reduces local and remote organ inflammatory mediator expression. Our G31P treatments reduced neutrophil influx into the affected tissues and also reduced the gut pathology scores, though somewhat less dramatically so. We wished to determine whether these effects were correlated with local expression of inflammatory cytokines and chemokines. Thus we measured the tissue levels of TNFα, IL-1β, IL-6, IL-10, GRO, CINC-2α, and MIP-2 expression in both the gut and lungs of our animals using qRT-PCR. In the jejunum, I/R injury markedly induced expression of IL-6, GRO, CINC-2α and MIP-2, but only modestly upregulated expression of TNFα (FIG. 10). IL-1β was not significantly upregulated as a consequence of the I/R injury. ELR-CXC chemokine blockade decreased IL-6 and IL-10 expression by 20% and 44% respectively, but had no discernible effect on TNFα expression. Interestingly, the G31P treatment also reduced MIP-2 and GRO, but not CINC-2α, expression.

Figure 11:
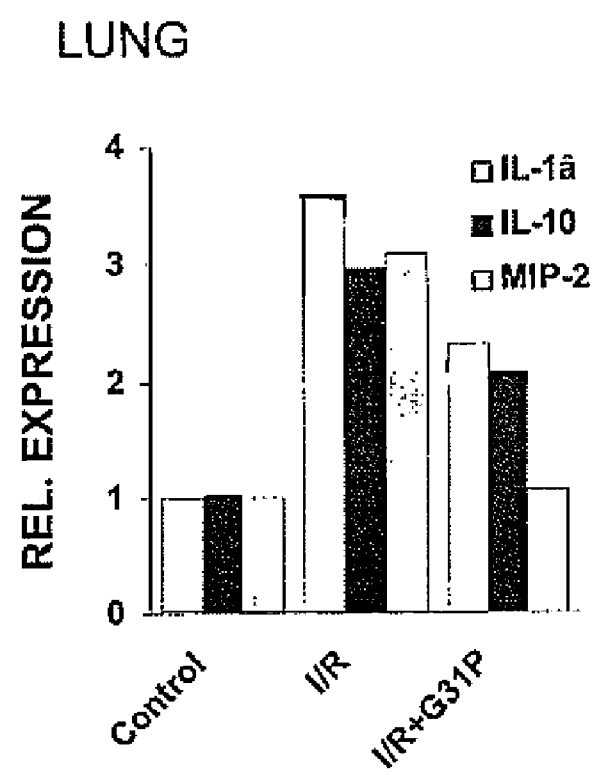
FIG. 11. Effect of G31P treatments on expression of proinflammatory cytokine and chemokine in I/R injury lung tissues. Lung tissues obtained as in FIG. 6 were also processed for total RNA extraction, and the levels of cytokine and chemokine expression were assayed by qRT-PCR, as in FIG. 10. The data are expressed as the relative quantities of mRNA relative to a calibrator sample (a representative sham surgical group sample). The results indicate that I/R injury differentially increased expression of IL-β, IL-10, and MIP-2, but not TNF, IL-6, GRO, or CINC-2, relative to the sham-surgical animals. The G31P treatment reduced MIP-2 expression to background and reduced IL-6 and IL-10 expression by 50 and 30% respectively. These results are from one experiment that is representative of two independent experiments.

In the lungs, we observed markedly reduced inflammatory mediator expression relative to the gut, with some of these not achieving expression levels two-fold greater than the sham surgical controls (our internal cut-off for significantly increases in qRT-PCR signals). Thus, we consider that there were no significant increases in TNF, IL-6, GRO, or CINC-2α expression in the I/R injury animals relative to the sham surgical controls. On the other hand, the levels of IL-1β, MIP-2, and IL-10 were increased approximately three-fold with the tissue injury. G31P treatments reduced the expression of MIP-2 to near background and reduced IL-1β and IL-10 expression by 50 and 30%, respectively, relative to the saline control animals (FIG. 11). These results indicate that G31P treatment did reduce ELR-CXC chemokine expression in the inflamed lung tissues following intestinal ischemia and reperfusion.

Human CXCL8$_{(3-72)}$K11R/G31P effectively antagonizes both CXCR1- and CXCR2-dependent activation of neutrophils. To confirm unequivocally whether human CXCL8$_{(3-72)}$K11R/G31P (G31P) acts at least in part through the CXCR1 we employed CXCR1-transfected HEK293 cells. We confirmed by FACS and qRT-PCR (FIG. 12A) that these cells express this receptor but not the CXCR2 and that 100 ng/ml CXCL8 induced chemotactic and intracellular Ca$^{++}$ flux responses. At 10 ng/ml G31P ≈80% blocked CXCL8-induced chemotactic responses, while at 100 ng/ml (but not 10 ng/ml) it dramatically reduced intracellular Ca$^{++}$ flux (FIG. 12A). Given the biological differences between CXCR1-transfected HEK cells and neutrophils, we also confirmed with freshly purified human neutrophils that G31P blocked CXCL8 (10 ng/ml)-induced chemotaxis and reactive oxygen intermediate (ROI) release (FIG. 12B). It is noteworthy that neutrophil superoxide release is reportedly attributable exclusively to CXCR1 signaling (Park et al., 2000, *Anesth. Analg.* 89:42-48). We also found that 10 ng/ml G31P markedly attenuated intracellular Ca$^{++}$ flux induced by 100 ng/ml CXCL8 (FIG. 12B). We then assessed G31P's ability to block activation of neutrophils induced by CXCR2-exclusive ligands. As with CXCL8, G31P dose-dependently blocked chemotactic responses of neutrophils to CXCL1 and CXCL5 (both 100 ng/ml), while 10 ng/ml G31P≦95% reduced intracellular Ca$^{++}$ flux induced by an optimal dose (100 ng/ml) of either ligand (FIG. 12C). It is noteworthy that, overall, CXCL8 was a substantially stronger agonist than either CXCL1 or CXCL5 in terms of inducing this intracellular Ca$^{2+}$ response.

Figure 13:
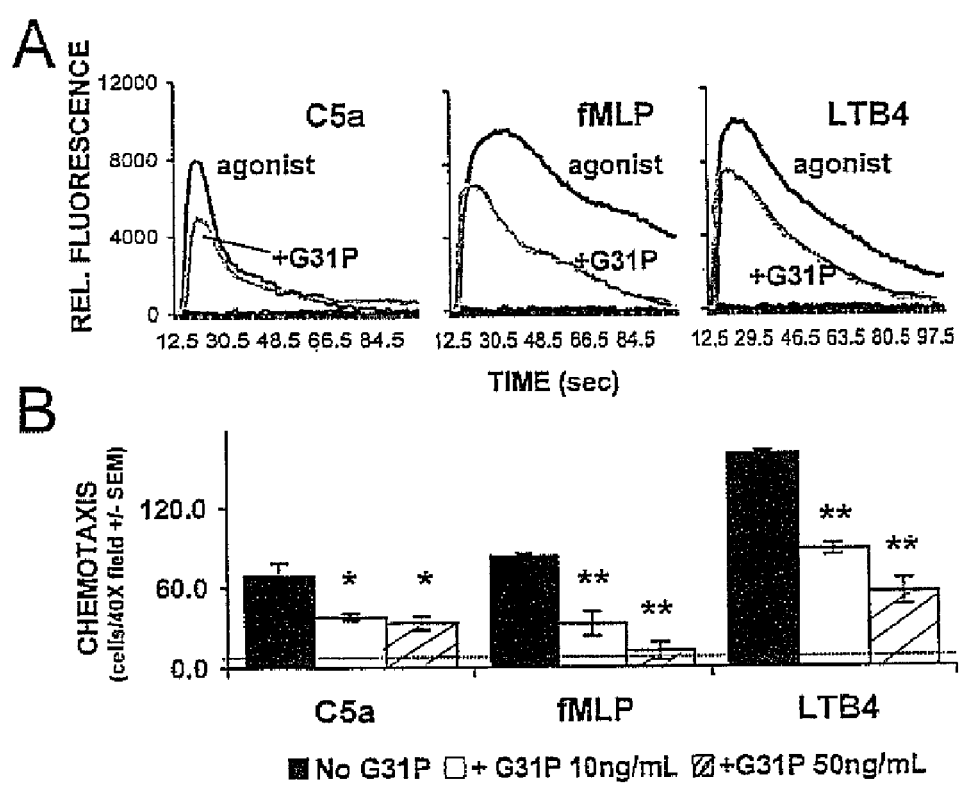
FIG. 13. G31P engagement on neutrophils induces heterologous desensitization of their G protein-coupled receptors for C5a, LTB4, and fMLP. Purified human neutrophils were stimulated with 0.1 nM C5a, 1 nM fMLP, or 1 ng/ml LTB4, in the absence or presence of 10 or 50 ng/ml of G31P, as described in the Materials and Methods. (A) The ability of G31P (10 ng/ml) to interfere with the agonist-induced intracellular $Ca^{2+}$ flux was assessed as in FIG. 12. (B) The abilities of varying doses of G31P to block the cells' chemotactic responses were also assessed as above. G31P very substantially reduced $Ca^{++}$ flux induced by fMLP and LTB4, but was less effective in blocking C5a-dependent $Ca^{++}$ flux, and this relative efficacy was observed also in the chemotaxis assays. * and **, $p<0.05$ and 0.01, respectively, relative to the agonist treatments alone. The data shown are representative of at least three experiments performed with similar results. The dashed lines across graph in panel B represents the mean background response in the assay.

G31P induces heterologous desensitization of alternate G protein-coupled receptors. Numerous neutrophil agonists, including C5a, LTB4, ELR-CXC chemokines, and fMLP, signal into these cells via distinct G protein-coupled receptors (GPCR). It has been shown previously that signaling through C5a, fMLP, or CXCL8 can reciprocally desensitize neutrophil chemotactic responses to subsequently introduced heterologous ligands (Blackwood et al., 1996, *J. Leukoc. Biol.* 60:88-93). On the other hand, CXCL8 reportedly does not effectively desensitize C5a- or fMLP-induced neutrophil activation as assessed by intracellular Ca$^{++}$ flux (Richardson et al., 1995, *J. Biol. Chem.* 270:27829-27833; Tomhave et al., 1994, *J. Immunol.* 153:3267-3275). In assessing G31P's relative capacity to affect heterologous GPCR signaling, it is important to recognize that G31P has a much higher affinity for its receptors than do the ELR-CXC chemokines. Thus, bovine G31P inhibits by 50% the chemotactic responses of neutrophils to a ≈250-fold higher concentration of native ligand (i.e., CXCL8) (Li et al., 2002). We wished to assess then the extent to which G31P would desensitize neutrophil responses to ligands such as C5a, fMLP, and LTB4, each of which are relevant neutrophil agonists in inflammatory conditions. Thus we examined G31P's impact on intracellular Ca$^{++}$ flux and chemotactic responses induced by each of these agonists (FIG. 13). We found that 0.1 nM C5a induced marked Ca$^{++}$ flux in neutrophils, as well as chemotactic responses, and that the addition of G31P reduced C5a-mediated chemotaxis by although its impact on intracellular Ca$^{++}$ flux was substantially more modest. The bacterial tripeptide fMLP induced a much more robust Ca$^{++}$ flux response than did C5a, but an essentially equivalent chemotactic response. The G31P treatment very substantially reduced both the Ca$^{++}$ and chemotactic (85% reduction) responses. LTB4 was a strong neutrophil agonist in both assays and, as with fMLP, G31P substantially reduced LTB4-induced Ca$^{++}$ flux and chemotactic (≈67% reduction) responses. Taken together, these data show that G31P did dampen neutrophil responses to each of these heterologous GCPR ligands.

Figure 14:
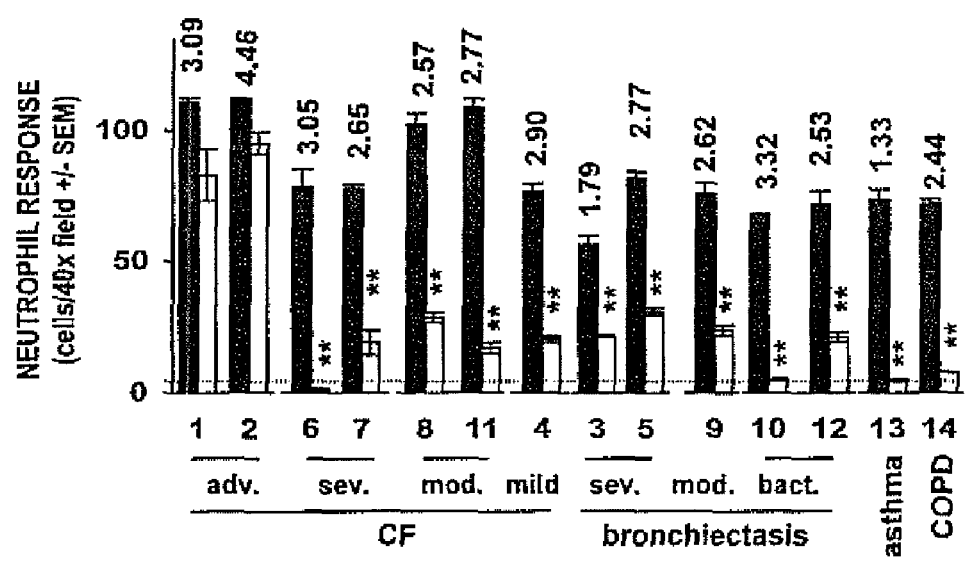
FIG. 14. G31P antagonizes the neutrophil chemotactic activities present in sputum from cystic fibrosis (CF) and bronchiectasis patients with bacterial pneumonia. Sputum samples were collected from 12 CF or bronchiectasis patients with bacterial pneumonia as well as two control subjects with COPD or asthma, and assayed for their CXCL8 content (values above the black bars). The abilities of G31P (10 ng/ml) to antagonize chemotactic responses of neutrophils from healthy donors to optimized dilutions of the sputa were assessed as in FIG. 12. The data are expressed as the mean (±SEM) number of cells/40× objective microscope field. The assays were repeated twice and gave essentially the same results each time. Sputum from healthy donors did not induce any significant neutrophil chemotactic responses (data not shown). With the exception of samples 1 and 2, G31P significantly reduced the cells chemotactic responses. **, $p \leq 0.01$ versus no G31P treatment. The dashed lines across the graph represents the mean background response in the assay.

Human G31P effectively antagonizes the inflammatory mediators present in sputum from bacterial pneumonia patients. As suggested above, inflammatory diseases are marked by the simultaneous expression of numerous neutrophil agonists. Sputum from cystic fibrosis (CF) patients, for example, can contain CXCL8 and other CXC chemokines, LTB4, formyl peptides (e.g., fMLP), and perhaps C5a (Mackerness et al., 2008, *Thorax* 63:614-620). Thus, given our data documenting that G31P can variably desensitize these receptors we wished to know just how effective it would be in blocking the agonists present in inflammatory samples. Thus, we obtained a bank of sputa from 12 CF and bronchiectasis patients being treated for bacterial pneumonia and directly tested the impact of G31P on their neutrophil chemotactic activities (FIG. 13). The disease status of the CF donors was classified as advanced, severe, moderate or mild, and that of the bronchiectasis donors as severe or moderate, or frank bacterial pneumonia, based on clinical criteria. We included sputum from one asthmatic and one chronic obstructive pulmonary disease (COPD) subject as controls. We assessed the levels of CXCL8 in each sputum sample (FIG. 14; values above the sample bars) and found that these correlated positively with the samples' ability to induce neutrophil chemotaxis (r=0.63 [14 DF], p=0.013). At 10 ng/ml G31P≈60-95% inhibited the chemotactic responses of neutrophils from healthy blood donors to the sputum from 10 of the 12 cystic fibrosis and bronchiectasis donors. Only sputum from the two donors classified as having advanced cystic fibrosis (donors 1 and 2) appeared more or less resistant to the antagonistic effects of G31P in this assay. Interestingly, the relative ability of G31P to block sputum-induced neutrophil chemotactic activities (i.e., percent inhibition) was not significantly correlated with the levels of CXCL8 in the samples (r=0.369 [14 degrees of freedom], p=0.15). For example, sample 1 contained 3.09 ng/ml of CXCL8 and was only modestly affected by G31P, while sample 10 contained 3.32 ng/ml CXCL8 and its activity was almost ablated by the G31P treatment. The sputum from the asthmatic and COPD subjects also induced marked neutrophil responses and G31P largely blocked these too; we have reported previously that sputum from asthmatic subjects contains high levels of CXCL8 (Gordon and Li. 2002, *FASEB J.* 16:A1079).

Figure 15:
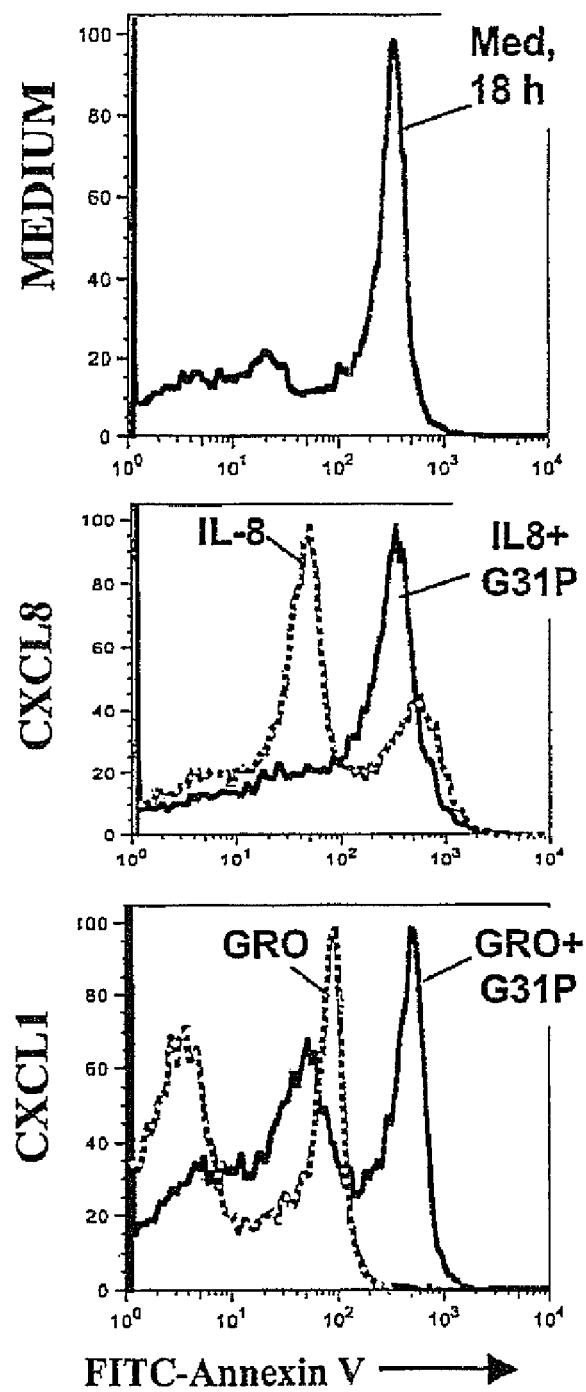
FIG. 15. G31P reverses the anti-apoptotic influence of CXCL1 and CXCL8 on neutrophils. Purified human neutrophils were cultured for 18 h in medium alone (apoptosis positive control; top panel) or in the presence of 100 ng/ml CXCL1 or CXCL8, either with (solid lines) or without (dashed lines) G31P (100 ng/ml), and stained with fluorochrome-labeled annexin V. The proportions of apoptotic (annexin V-binding) cells were determined by FACS. Negative control results obtained using freshly purified annexin V-stained neutrophils (shaded tracing) are included in each graph. Necrotic cell death was also assessed by propidium iodide uptake; we found ≦3% propidium iodide-positive cells in all samples. The data indicate that cells incubated in medium alone were largely apoptotic. Exposure to CXCL8 or CXCL1 reduced apoptosis very substantially, but addition of G31P to these cultures largely reversed the ELR-CXC chemokine-induced anti-apoptotic effects. These assays were repeated three times.

Human G31P blocks ELR-CXC chemokine-mediated anti-apoptotic effects in neutrophils. As neutrophils leave the vasculature or become effete they rapidly undergo programmed cell death or apoptosis as a means of preventing adventitious host pathology. However, during inflammatory events it is in the best interest of the host to maintain these cells in a viable state such that they can effectively engage microbial targets. An array of inflammatory mediators, including the ELR-CXC chemokines, have anti-apoptotic effects on neutrophils (Glynn et al., 2002, *Pulm. Pharmacol. Ther.* 15:103-110). We wished to know then whether G31P's anti-inflammatory effects would extend to reversing chemokine-induced anti-apoptotic processes, thereby allowing neutrophils to quickly progress into apoptosis. We used FITC-annexin V binding as our assay of apoptosis. We stained freshly purified neutrophils with this marker as a negative control (shaded signal, FIG. 15) and cells that had been cultured for 18 h in medium alone as an apoptosis positive control (FIG. 15, upper panel). The freshly purified cells appeared to have two levels of annexin binding, with most cells being more or less negative and a smaller proportion binding moderate levels of this apoptosis marker. When we added CXCL8 to the cells (FIG. 15, middle panel, dashed line) there was a marked diminution of the numbers of cells that strongly bound annexin V and the addition of G31P to these cultures fully reversed this CXCL8-induced anti-apoptotic activity. CXCL1 also had protective effects on neutrophils, but they were subtly different than those of CXCL8 (FIG. 15, bottom panel, dashed line). The CXCL8-protected cells had largely bound intermediate levels of annexin V, while those incubated with CXCL1 bound either very low or intermediate levels of annexin. The addition of G31P to the CXCL1 cultures induced a substantial proportion of the cells to upregulate their apoptotic processes, but nevertheless there remained a significant population of cells that bound intermediate levels of annexin.

Figure 16:
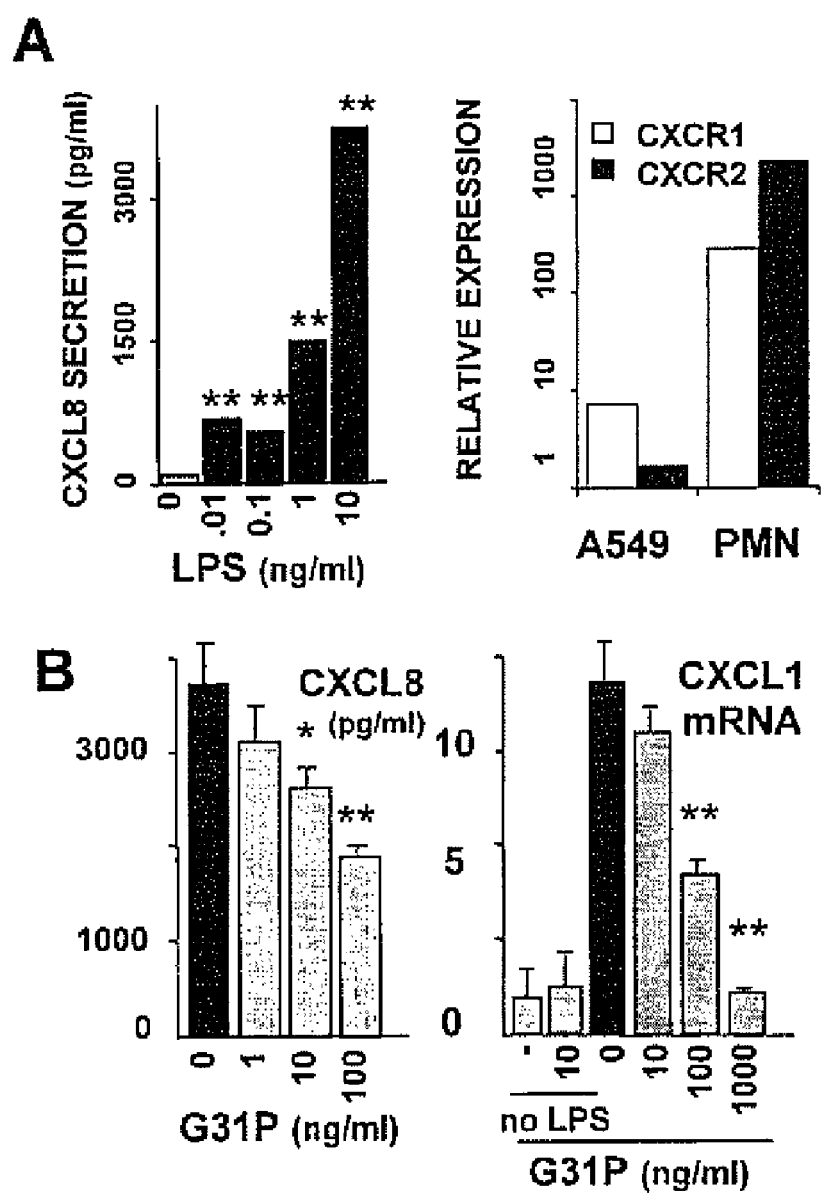
FIG. 16. G31P antagonizes the endotoxin-induced inflammatory cycle in human bronchial epithelial cells. Monolayers of A549 bronchial epithelial cells were exposed to (A) varying doses of endotoxin, and the culture supernatant collected 16 h later and assayed by ELISA for CXCL8 (left panel). Expression of the CXCR1 or CXCR2 by the A549 cells and human neutrophils was assessed by qRT-PCR using specific primers (right panel). Our data indicate that peak CXCL8 expression was found in the A549 cultures that were challenged with 10 ng/ml LPS, and that our A549 cells expressed significant levels of CXCR1, though certainly much less than that found in neutrophils. (B) A549 cell monolayers were challenged with 10 ng/ml of LPS in the presence of the indicated concentrations of G31P, and 16 h later the culture supernatants and cellular RNA was isolated and assayed for CXCL8 protein (ELISA) and CXCL1 mRNA (qRT-PCR). Addition of G31P to the A549 cells dose-dependently suppressed expression of both chemokines by the LPS-challenged cells. * and **, $p<0.05$ and $0.01$, respectively, relative to the baseline treatments alone. The data shown are representative of at least three experiments performed with similar results.

Human G31P antagonizes the inflammatory cycle in endotoxin-challenged bronchial epithelial cells. Exposure of the airway epithelium to bacterial endotoxin triggers a pulmonary inflammatory response, wherein these cells secrete CXCL8, for example, which directly fosters neutrophil recruitment into this tissue compartment. While we have shown that G31P antagonizes the impact of the ELR-CXC chemokines on neutrophil responses, little attention is paid to whether epithelial cells themselves respond to the ELR-CXC chemokines they elaborate in airway endotoxemia, or to the neutrophils they recruit. We thus decided to investigate this using human type II alveolar A549 epithelial cells that we challenged with bacterial endotoxin (FIG. 16) in the presence or absence of G31P. The quiescent A549 cells secreted very little CXCL8, but LPS dose-dependently up-regulated their expression of this chemokine. Reports of CXCR1 and CXCR2 expression by epithelial cells vary, so we wished first to determine whether our A549 cells expressed either of these receptors. We used qRT-PCR and did indeed detect significant levels of the CXCR1 (FIG. 16A, right panel) but little in the way of CXCR2. When we challenged our A549 cells with 10 ng/ml LPS in the presence of increasing doses of G31P, the cells produced progressively less CXCL8 (FIG. 16B). This effect extended also to their expression of CXCL1, wherein G31P reduced LPS-induced CXCL1 expression by 98%, as determined by qRT-PCR.

Figure 17:
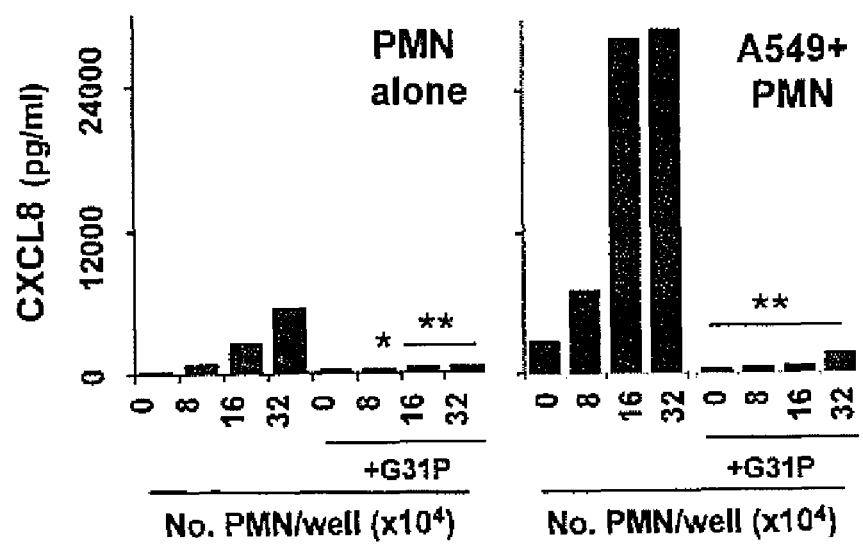
FIG. 17. Co-culture of quiescent A549 cells with unstimulated peripheral blood neutrophils leads to synergistic CXCL8 expression. The indicated numbers of quiescent, purified human peripheral blood neutrophils from healthy donors were either cultured alone (PMN alone) or added to monolayers of unstimulated A549 cells (A549+PMN). G31P (100 ng/ml) was added to half of these cultures and 16 h later the culture supernatants were harvested assayed for CXCL8 by ELISA. The addition of neutrophils to the A549 cells synergistically enhanced expression of CXCL8 in a cell concentration-dependent fashion, and G31P antagonized this cytokine response. * and **, $p<0.05$ and $0.01$, respectively, relative to the no G31P treatments alone. The data shown are from one blood donor that is representative of the responses of three such donors.

Neutrophils release a variety of mediators that are potential epithelial cell agonists (e.g., elastase (Chen et al., 2004, *J. Biomed. Sci.* 11:49-58)), while epithelial cells similarly secrete neutrophil agonists. This suggests the possibility that these cells could through a putative mutual stimulatory mechanism drive an escalating inflammatory process. We tested this by co-culturing purified otherwise quiescent neutrophils with monolayers of resting A549 cells. While the neutrophils were largely unstimulated, there was a significant background release of CXCL8 by these cells over 16 h in culture (FIG. 17). Nevertheless, simple co-culture of these neutrophils with A549 cells induced a synergistic expression of CXCL8 in the cultures, and this effect was dependent on the numbers of neutrophils added to the cultures (FIG. 17). The A549 cells did not secrete significant amounts of CXCL8 when cultured on their own. The addition of G31P to these co-cultures dramatically (up to 98%) reduced the expression of CXCL8 ($p \leq 0.01$; FIG. 17).

Figure 18:
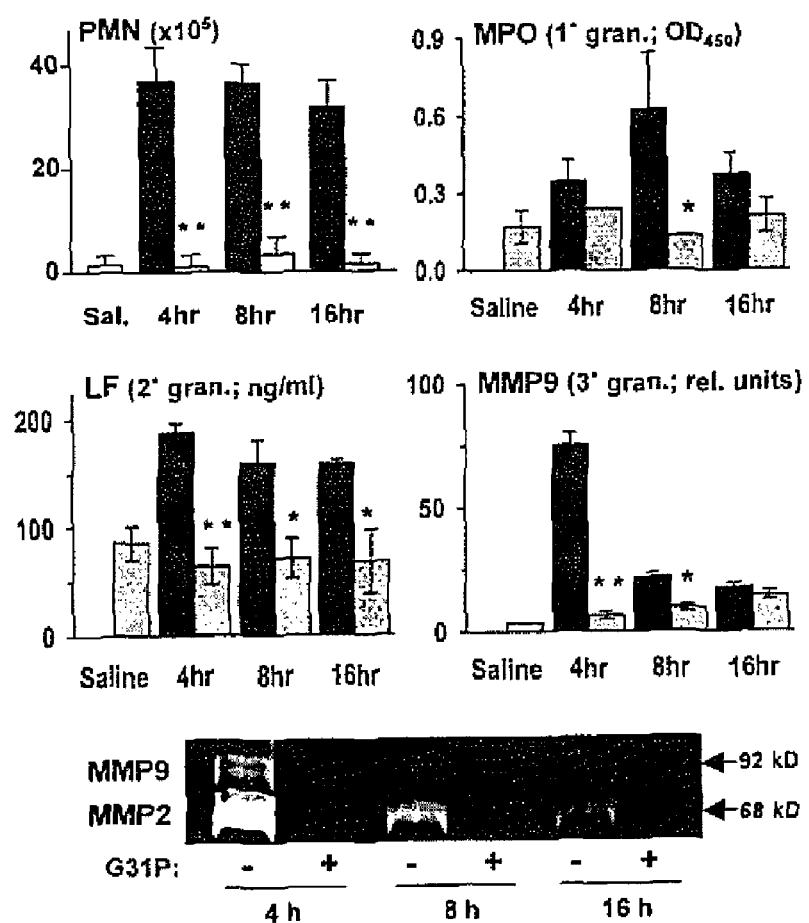
FIG. 18. G31P treatments reduce neutrophil activation in airway endotoxemia. Airway endotoxemia was induced in guinea pigs by i.n. instillation of bacterial endotoxin (5 µg/kg). The animals (n=5) were treated 30 min prior to challenge with either saline (black bars) or G31P (grey bars; 250 µg/kg) and euthanized 4, 8, or 16 h later. Differential counts were done on the cells recovered by bronchoalveolar lavage (BAL) and the BAL fluids were assessed for the levels of myeloperoxidase (MPO), lactoferrin (LF), and matrix metalloproteinase-9 (MMP-9), as specific markers of neutrophil primary, secondary, and tertiary granules, respectively, as noted in the materials and methods. The MMP-9 graphical data were obtained from the zymogram (lower panel) by gel scanning densitometry. The zymogram shows the BAL levels of MMP-9 (92 kD) and MMP-2 (68 kD), an activation marker of lung structural cells. The G31P treatments dramatically reduced neutrophil activation in the airways as well as structural cell activation. *, $p<0.05$ and **, $p<0.01$ as compared with LPS plus saline treatment only. Data are expressed as the mean±SEM, and are representative of two repeat experiments.

Human G31P blocks airway endotoxemia-induced acute lung inflammation. The observations that a fully human form of G31P blocked inflammatory responses at multiple levels (e.g., heterologous desensitization of GCPR, pro-apoptotic effects, blockade of the autocrine epithelial inflammatory cycle) suggested that it could be effective also in blocking inflammatory responses in vivo. We have shown that bovine and bovine-human chimeric orthologues of human G31P can block an array of inflammatory pathologies, including airway endotoxemia (Gordon et al., 2005; Zhao et al., 2007), aspiration pneumonia, ischemia-reperfusion injury, and environmental pollutant-induced lung injury (Podechard et al., 2008, *Toxicol. Lett.* 177:130-137). While we know in airway endotoxemia that bovine G31P treatments reduce neutrophil infiltration of the airways, it remains possible that neutrophils marginate in the pulmonary vasculature under the influence of the inflammatory mediators expressed in this compartment and are activated in situ. For this reason we wished to determine whether we could detect markers of the individual neutrophil granules or of activated structural cells in the lungs of endotoxemic animals. We induced airway endotoxemia in guinea pigs as reported previously (Gordon at al., 2005; Zhao et al., 2007) and assessed the levels of myeloperoxidase (MPO; 1° granules), lactoferrin (LF; 2° granules), and matrix metalloproteinase-9 (MMP-9; 3° granules) at 4, 8, and 16 h after endotoxin challenge. We confirmed that G31P did indeed reduce airway neutrophilia (90-99% reduced at 4, 8 and 16 h; $p \leq 0.01$ versus saline-treated animals). In concert with this there were significant reductions in the BAL levels of myeloperoxidase (MPO; $p \leq 0.05$, 8 h time-point only), lactoferrin (LF; $p \leq 0.05$, all times), and matrix metalloproteinase-9 (MMP-9; $p \leq 0.05$, 4 and 8 h time-points), which suggested that the few neutrophils that did achieve the lungs were not sufficiently activated to degranulate. We coincidentally observed a very strong signal from a 68 kD gelatinase (FIG. 18) that co-migrated with MMP-2 expressed in positive control HT1080 fibrosarcoma cells, suggesting that we had indeed strongly activated the lung epithelium and other structural cells that express this metalloproteinase (D'Ortho et al., 1994, *Am J Physiol Lung Cell Mol Physiol* 266:L209-216; Fligiel et al., *Hum. Pathol.* 37:422-430). G31P treatment also essentially abrogated this response at each time suggesting that, as we had observed with our A549 cells, structural cells were also influenced by ELR-CXC chemokine antagonism in vivo.

Figure 19:
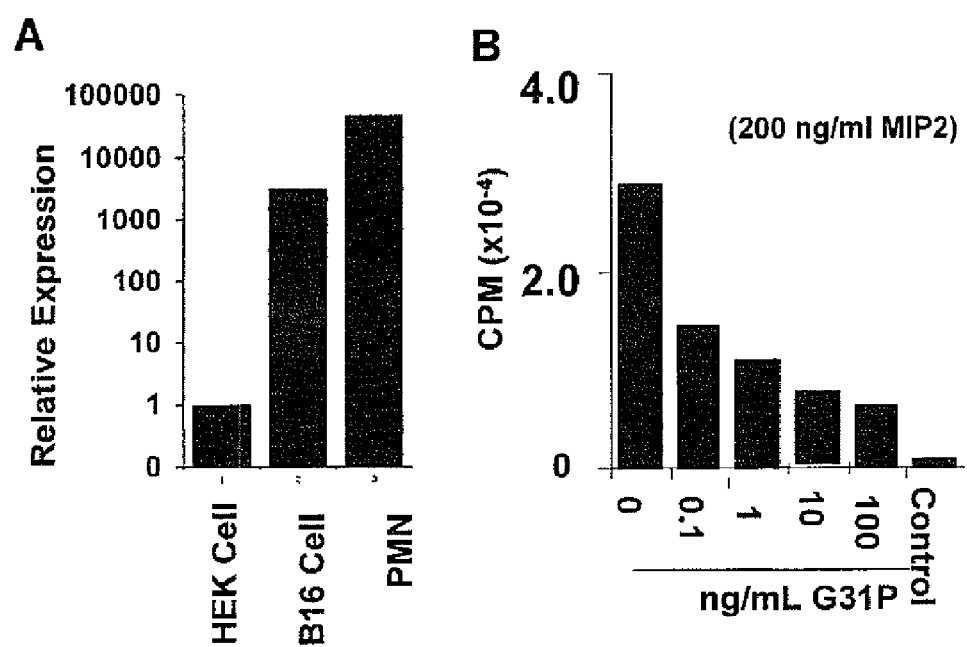
FIG. 19. (A) RNA was isolated from HEK cells, B16-10 melanoma cells or mouse neutrophils (positive control) and CXCR2 expression was evaluated by qRT-PCR. (B) B16-10 melanoma tumour cells were treated with 200 ng/mL rmMIP2 and varying concentrations of G31P. Proliferation was evaluated after 72 hr using traditional $^3$H-thymidine uptake assays.

As shown in FIG. 19, the tumour cells expressed CXCR2, and G31P dose-dependently reduced MIP2-induced tumour cell proliferation.

We previously reported that G31P dampens CXCL1 and CXCL8 expression by LPS-challenged bronchial epithelial cells by interrupting an autocrine stimulation network. As shown in FIG. 20, we assessed whether tumour cells similarly use ELR-CXC chemokines as autocrine growth factors. B16-10 cells were treated with varying concentrations of G31P for 16 hr at 37° C., then their RNA was extracted and KC expression was evaluated by qRT-PCR. As can be seen from FIG. 20, G31P had modest effects on the B16 cells, reducing KC mRNA levels by ≈35%

As shown in FIG. 21, It is apparent that the G31P treatments reduced the development of grossly or histologically-discernible tumours in the lungs of the tumour-challenged mice.

As shown in FIG. 22, G31P reduced the development of grossly or PCR-detectable tumours in the lungs but, unexpectedly, did so in a reciprocal fashion with respect to G31P treatment time.

As shown in FIG. 23, while G31P had modestly reduced the in vitro expression by tumour cells of KC in vitro, it had no discernible impact on the expression of inflammatory markers (IL-6, KC, MIP2) in the lungs of tumour-challenged animals.

Preparation of Gastric Content. The Stomach Contents were Collected from Healthy guinea pig donors and dispersed in normal sterile saline, filtered through sterile gauze and centrifuged at 220×g for 10 min at room temperature. A stock solution of gastric contents was prepared in normal saline at 100 mg/ml, aliquoted and stored in −80° C. This stock was further diluted to 40 mg/ml and adjusted to pH 2.0 immediately before use.

Guinea pig aspiration pneumonia model. Guinea pigs were anesthetized by i.p. injection of 40 mg/kg ketamine and 5 μg/kg xylazine and given 250 μl of gastric contents (35 mg/kg body weight) intranasally. They were then treated with either saline or G31P (250 μg/kg body weight) s.c. Groups of control animals were given only normal sterile saline or acidified sterile saline (pH 2.0) intranasally. All animals were euthanized with halothane after 20 h. Bronchoalveolar lavage (BAL) fluid collection, BAL WBC (and RBC) enumeration and differentials were performed as noted (Gordon et al., 2005) and the results expressed as the mean number of cells per ml BAL sample. Peripheral blood total WBC counts and differentials were performed as well. BAL fluids and serum were aliquoted and stored at −80° C., while samples of lung tissue was harvested and stored at −20° C. in RNAlater solution until processed for RNA purification. The samples from each animal were assessed independently.

Myeloperoxidase assay. BAL fluids were diluted 10-fold with 0.5% hexadecyltrimethylammonium bromide (HTAB), and 10 μl of the diluted samples were incubated at room temperature for 10 min with 100 μl tetramethylbenzidine (TMB), before stopping the reactions with 100 μl of 1M phosphoric acid. The reactions were quantified by spectroscopy (OD, 450 nm) and the data expressed as $OD_{450}$±SEM.

Lactoferrin ELISA. We employed a standard capture ELISA format, with optimized concentrations of capture (2.45 μg/ml) and detection (0.85 μg/ml) antibodies, as noted (Xixing Zhao et al., 2007). The standards comprised purified lactoferrin (6.25-400 ng/ml). The BAL samples were diluted 1:10 for the assay (sensitivity, 6.25 ng/ml). The results are expressed as the mean concentration (ng/ml) of each group±SEM.

Assessment of lung tissue neutrophilia. After bronchoalveolar lavage, the caudal left lung lobe of each animal was fixed for 3 h in acid-alcohol formaldehyde (Gordon et al., 2005) and routinely processed to 7 μm paraffin sections, which were stained with hematoxylin and eosin and examined in a blinded manner using a 40× objective. The results were expressed as the mean of neutrophils/40× field for each group (n=5)±SEM.

Peripheral blood neutrophil chemotaxis. Neutrophils were purified from the peripheral blood from each animal and used for modified Boyden chamber microchemotaxis assays, as reported previously (Li et al., 2002; Li et al., 2002; Xixing Zhao et al., 2007; 7:1723-31. Purified neutrophils were suspended in PBS+ (phosphate-buffered saline [PBS; pH 7.4], 1.2 mM $MgCl_2$, 5 mM KCl, 0.5 mM $CaCl_2$, 5 mM glucose, and 0.1% bovine serum albumin). Human CXCL8 (10 ng/ml) or PBS were used as chemoattractants for each sample in the assays, which were quantified by direct counting of at least five 40× objective fields per well. The results are presented as the experimental minus control well values (i.e., CXCL8 minus PBS responses) for each animal, and expressed as the mean number of cells per 40× field±SEM.

Isolation of lung tissue total RNA and quantitative real time PCR (qRT-PCR). Guinea pig lung tissues were harvested and stored in 600 μl RNAlater at −20° C., and the sample RNA isolated and purified using Qiagen RNeasy Mini Kits, according to the supplier's protocol. The total RNA was quantified using a spectrophotometer and stored at −80° C. for later use. The levels of β-actin, CXCL1 and CXCL8 mRNA in each sample were determined by qRT-PCR. The guinea pig gene-specific primers were: β-actin forward: 5'-CGT AAG GAC CTC TAT GCC AAC AC-3' (SEQ ID No. 2) and β-actin reverse: 5'-GAC TCA TCG TAC TCC TGC TTG CT-3' (SEQ ID No. 3); CXCL1 forward: 5'-CCC AAG AAC ATC CAG AGC GTA G-3' (SEQ ID No. 4) and CXCL1 reverse: 5'-TGG CTT TGC TTC CTT TCA GC-3' (SEQ ID No. 5); CXCL8 forward: 5'-TGC GAT GCC AGT GTA TTA AGA TT-3' (SEQ ID No. 6) and CXCL8 reverse: 5'-CTC TTC AAG AAC ATG CTC ACC AC-3' (SEQ ID No. 7). We used a Stratagene Brilliant® SYBR® Green QRT-PCR Master Mix Kit (one-step) for the qRT-PCR, with a thermal profile of: first segment: 50° C. for 30 min, and 95° C. for 10 min, 1 cycle; second segment: 40 cycles of 95° C. for 30 sec, 62° C. for 30 sec, and 72° C. for 30 sec, followed by a dissociation curve.

BAL bacteriology. BALF was diluted 1:250 after collection and 100 μl aliquots used for blood agar plate cultures. After overnight incubation at 37° C., the bacterial colonies were counted on each plate and differentiated by Gram staining and microscopic observation by our bacteriology service. The results were expressed as the mean number of Gram-negative or -positive enterobacilli, or Gram-positive *corynebacterium*-like organisms for the BAL samples from each group (±SEM).

Animal model of intestinal I/R-induced injury. Rats were fasted for 20 hours before the experiments but allowed free access to water. On the day of the experiment, the animals were anaesthetized using ketamine/xylazine (40 μg/kg/5 μg/kg, i.p.) and maintained under anaesthesia with 1% isoflurane and 1% oxygen. The animals were given 0.05 mg/kg buprenorphine i.m. for pain management. A laparotomy was performed and the superior mesenteric artery (SMA) was isolated and totally occlusion for 1 hour using a plastic loop and tubing. After removal of the ligature, the abdominal incision was closed using 4-0 monofilament suture thread. The animals were allowed to recover for 2 hours as the reperfusion injury developed, and then they were euthanized with halothane. Sham-operated animals underwent identical surgical procedures with the exception that the plastic loop and tubing placed around the SMA was not closed to occlude blood flow. We ran multiple preliminary experiments in order to optimize ischemia and reperfusion times, including 0.5, 1, 1.5, and 2 h ischemia and 0.5, 1, 2, 4, 8, 16 h reperfusion time. Based on a minimization of mortality with maintenance of discernible pathology, 1 and 2 h were chosen as our ischemia and reperfusion times, respectively, for all subsequent experiments. For these the animals were assigned to three groups: sham, 1/R animals given saline control treatments, and 1/R animals given 500 µg/kg G31P s.c. (n=5). The dose of G31P was chosen based on preliminary experiments. All experiments were repeated three times.

Determination of circulating leukocytes and neutrophils. Blood smears were stained with Wright's solution and differential counts performed on 200 cells per sample. Total white blood cells (WBC) were enumerated by hemocytometer counting after lysis of the red blood cell (RBC) with 2% acetic acid in water. The total neutrophil numbers were calculated from these values.

Examination of bronchoalveolar lavage fluid protein levels, neutrophil and RBC numbers. Bronchoalveolar lavage fluid (BALF) was collected as noted previously using 2 ml volumes of sterile saline (21). BALF total WBC and RBC were enumerated by direct counting, and the results expressed as the mean number of cells per BALF sample (±SEM). BALF WBC cell differentials were determined using Wright's-stained BALF cell cytospin preparations and the total numbers of neutrophils were calculated using these data. All the data are expressed as means±SEM. The total protein level was determined using duplicate replicates in a Bradford microassay according to the suppliers protocols (Bio-Rad Laboratories), with bovine serum albumin protein standards. The data was expressed as µg protein/ml BALF fluid (±SEM).

Measurement of MMP-2 and MMP-9 by zymography. Lung and gut tissue homogenates were prepared and MMP-2 and -9 levels were assessed. Briefly, equal weights (100 mg wet wt) of right lung and jejunum from each animal were suspended in 1 ml of 0.5% hexadecyltrimethylammonium bromide (HTAB) in 50 mM phosphate buffer (pH 6.0) and homogenized for 20 seconds, then sonicated three times for 30 seconds each, all on ice. The homogenates were centrifuged at 12,000 rpm at 4° C. and the supernatants harvested and stored at −80° C. Next, 40 µg equivalents of homogenate were applied to 8% polyacrylamide gels containing 2 mg/mL gelatin. After electrophoresis, the gels were first rinsed 3 times for 20 minutes each in 2.5% Triton X-100, then twice for 20 min each in incubation buffer (50 mmol/L Tris-HCl, 5 mmol/L $CaCl_2$, 150 mmol/L NaCl, and 0.05% $NaN_3$), and finally soaked overnight at 37° C. in incubation buffer. The soaked gels were stained for 2 h (2% Coomassie Brilliant blue G in 25% methanol/10% acetic acid [w/v]) before destaining with 2% methanol/4% acetic acid. The gelatinase activities of the samples were discerned as transparent bands against the Coomassie blue-stained gel background. To quantify the activities of enzymes, these zymograms were imaged using a GS-800 Calibrated Densitometer (Bio-Rad). The intensities of the individual bands were analyzed using Quantity1 software (Bio-Rad) and reported as such. Conditioned medium from untreated HT1080 cells was used as MMP-2 and MMP-9 reference standards.

Measurements of tissue cytokine and chemokine mRNA levels using quantitative real-time PCR (qRT-PCR). Lung and jejunum tissues were harvested and stored in 600 µl RNAlater at −20° C. The sample RNA was later purified using commercial RNA preparation kits, according to the supplier's protocol. The total RNA was quantified spectrophotometrically and stored at −80° C. The levels of β-actin, TNFα, IL-1β, IL-6, IL-10, GRO, CINC-2α, and MIP-2 mRNA in each group were determined by qRT-PCR, using the rat gene-specific primers. We used a one-step qRT-PCR master mix kit with a thermal profile of: first segment, 50° C. for 30 min and 95° C. for 10 min (1 cycle); and second segment, 95° C. for 30 sec, 62° C. for 30 sec, and 72° C. for 30 sec (40 cycles), followed by a dissociation curve.

Evaluation of pulmonary pathology and neutrophil sequestration. After bronchoalveolar lavage, the caudal left lung lobe of each animal was fixed for 3 h in acid-alcohol formaldehyde, and routinely processed to 6 µm paraffin sections, which were stained with hematoxylin and eosin (H&E). Neutrophils were enumerated by microscopy in a blinded manner under a 40× objective. The results were expressed as the mean of neutrophils/40× field for each group (n=5)±SEM.

Assessment of jejunal pathology. After euthanasia, the jejunum of each animal was examined and grossly graded for signs of edema and discolouration. In addition, the contents of the gut were gently extruded and examined. We established a five-point scoring system to assess gross gut pathology, as follows: 0, no discernible edema, discolouration of gut wall or jejunal contents; 1, no discernible edema or discolouration, but jejunum contains yellow fluid; 2, 10% of jejunum edematous, discoloured, and contained bloody-looking fluid; 3, 25% of jejunum edematous, discoloured, and contained bloody-looking fluid; 4, 50% of jejunum edematous, discoloured, and contained bloody-looking fluid; and 5, 100% of jejunum edematous, discoloured, and contained bloody-looking fluid. To assess histopathology, the jejunum wall of each animal was fixed and processed as described above, stained with H&E and examined in a blinded manner at 400× magnification.

Generation of G31P. A full-length human CXCL8 cDNA was synthesized commercially (Takara Biotech, Dalian, China). From this we generated a glutathione-S-transferase (GST) fusion protein construct encoding amino acids 3-72 of human CXCL8, then introduced a Lys11-to-Arg substitution (we reported previously that bovine $CXCL8_{(3-72)}K11R$ is a very high affinity CXCR1/CXCR2 agonist; (Li and Gordon, 2001, *Biochem. Biophys. Res. Commun.* 286:595-600)). We next introduced a $Gly^{31}$ to Pro substitution, to generate human $CXCL8_{(3-72)}K11R/G31P$ (G31P). Each plasmid was transformed into competent HB101 cells and their sequences were verified commercially (Plant Biotechnology Institute, Saskatoon, SK). The recombinant bacteria were sonicated in the presence of the protease inhibitors aprotinin (2 mg/ml) and PMSF (50 mM), then the recombinant GST fusion proteins present in the sonicates were purified by affinity chromatography using glutathione-sepharose columns. The recombinant CXCL8 analogues were cleaved from their GST fusion partners by thrombin digestion and then further purified using benzamidine-sepharose columns. The relative molecular mass and purity of each protein was verified by SDS-PAGE and Western blotting with biotinylated anti-human CXCL8 antibody.

Generation of CXCR1-transfected HEK293 cells. HEK293 cells (CRL-1573; American Type Culture Collection [ATCC], Manassas, Va.) were transfected with the gene for the CXCR1 in the vector pcDNA3.1+ (Missouri S&T cDNA resource center) using lipofectamine. The CXCR1-expressing cells were selected using gentamicin (800 μg/ml) and their expression of the CXCR1 gene was confirmed by FACS and qRT-PCR.

Chemotaxis assays. Chemotaxis was assessed using modified Boyden chamber microchemotaxis assays with either purified neutrophils or CXCR1-transfected HEK cells. For the former, human peripheral blood leukocytes were fractioned on standard density gradients, and the neutrophils harvested from the bottom of the gradients and cleared of contaminating red blood cells by hypotonic lysis. The purified neutrophils (or HEK cells) were suspended at $2 \times 10^6$/ml in PBS$^+$ (phosphate-buffered saline [PBS; pH 7.4], 1.2 mM $MgCl_2$, 5 mM KCl, 0.5 mM $CaCl_2$, 5 mM glucose, and 0.1% bovine serum albumin). The chemoattractants (e.g. CXCL8), either alone or together with G31P, were placed in the bottom compartment of the Boyden chamber wells and cells in the upper compartment, with the two compartments separated by polyvinylpyrrolidone-free, 5 (neutrophils) or 10 (CXCR1-HEK cells) μm pore-size polycarbonate filters. After incubation for 20 minutes (neutrophils) or 5 h (CXCR1-HEK cells) at 37° C. in a 5% $CO_2$ atmosphere, the cells that had migrated into the filters were fixed and stained using a Diff-Quick kit. The numbers of cells responding in each well were enumerated by direct counting of at least five 40× objective fields, and the results expressed as the mean number of cells per 40× field±SEM.

In a series of preliminary experiments we confirmed that CXCL1, CXCL5, and CXCL8 induced maximal neutrophil chemotactic responses at concentrations of 100, 100, and 10 ng/ml, respectively, while CXCL8 induced maximal CXCR1-HEK cell responses at 100 ng/ml. We also optimized the dilution of each sputum sample (i.e., 1:1 to 1:100) required to maximize its neutrophil chemotactic activity. We tested the effects on sputum-induced chemotactic responses of using G31P at 0.1-100 ng/ml, and found that the antagonistic effects observed at 10 ng/ml were not altered by increasing the dose of G31P.

Reactive oxygen intermediate release assay. We used total white blood cell (WBC) preparations for the reactive oxygen intermediate (ROI) release assays. To generate WBC, heparin-anticoagulated human blood was mixed with an equal volume of 6% (w/v) dextran (75 kD) in PBS, and then the tubes were allowed to stand upright and undisturbed for ≈1 h at room temperature. When the red blood cells had sedimented, the upper phase, comprising plasma, platelets and WBC, was centrifuged and the cell pellet resuspended at $2.5 \times 10^6$ cells/ml HBSS. For the assays, we mixed 50 μl of WBC, 25 μl of human CXCL8 (final concentration, 100 ng/ml) or HBSS, 25 μl of HBSS or the indicated concentrations of G31P, and 50 μl of luminol (0.3 mM). We had confirmed in preliminary experiments that 100 ng/ml CXCL8 was optimal for induction of WBC ROI release, as determined by chemiluminescence using a microplate spectrofluorimeter (NovoStar, BMG LABTECH Inc. Durham, N.C.). The data are expressed as the maximum sample luminescence minus that of cells exposed to HBSS alone.

Assay of intracellular $Ca^{2+}$ flux. Neutrophils were purified as described above, and then washed twice with $Ca^{2+}$-free PBS$^+$ medium and suspended at $5 \times 10^6$ cells/ml in the same medium. The cells were stained for 30 min at 37° C. with 2 μM fluo-4 AM, then washed twice with $Ca^{2+}$-free PBS$^+$, resuspended at $4 \times 10^6$ cells/ml in PBS$^+$ containing 3.3 nM $Ca^{2+}$, and kept at room temperature until used for testing. Prior to challenge, the cells were incubated for 15 min with medium or G31P (100 ng/ml), then challenged with medium or human CXCL1, CXCL5, or CXCL8 (each, 100 ng/ml). In preliminary experiments we had confirmed that 100 ng/ml induced optimal intracellular $Ca^{2+}$ flux in these cells, as determined using a microplate spectrofluorimeter (emission wavelength, 520 nm; excitation wavelength, 488 nm).

Heterologous desensitization of GPCR. Neutrophils were purified as above and resuspended in PBS$^+$ medium at $2 \times 10^6$ cells/ml, then stimulated with 0.1 nM C5a, 1 nM fMLP, or 1 ng/ml LTB4 in the presence of 0, 10 or 50 ng/ml G31P. The impact of the G31P on the agonist-induced intracellular $Ca^{++}$ flux and chemotactic responses were measured as noted above. These experiments were repeated three times.

Sputum samples. Sputum samples were collected for diagnostic purposes from 12 cystic fibrosis or bronchiectasis patients with bacterial pneumonia. Sputa from two subjects with COPD or asthma were also obtained as controls. For processing, the sputum mucus plugs were dispersed by treatment with 1% DTT/HBSS, then the cells were sedimented and the supernatants dialysed extensively against multiple changes of PBS. The level of CXCL8 in each sample was determined by ELISA. The supernatants were aliquoted and stored at −80° C. Sputum from healthy donors did not induce any significant neutrophil chemotactic responses.

Effects of G31P on responses of A549 bronchial epithelial cells. Human A549 bronchial epithelial cells (ATCC No. CCL185) were grown to a maximum of 90% confluence in 24-well plates in MEM (with L-glutamine) supplemented with 10% FBS, 0.01 M HEPES, and non-essential amino acids. Prior to stimulation, the cell monolayers were washed and provided with fresh medium, then exposed for 15 min at room temperature to 1-100 ng/ml of G31P. The indicated doses of LPS or $0-1.28 \times 10^6$ unstimulated purified neutrophils from healthy donors were added to the cells, which were incubated for 16 h at 37° C. before the supernatants were collected. Total RNA was collected from the cells using commercial extraction kits and standard approaches. ELISA assays were used to quantify cytokine levels in the supernatant fluids, while qRT-PCR was used to quantify the relative mRNA levels.

ELISA assay of cytokines and chemokines. Culture supernatants were not diluted before the assays, while BAL fluids for lactoferrin assays were diluted 1:10. The data are presented as pg/ml or ng/ml, based on recombinant protein standard curves. The cytokine ELISAs were sensitive to 5-10 pg/ml, while the lactoferrin assay was sensitive to 5 ng/ml. Our CXCL8 ELISA does not detect G31P, as the capture antibody does not recognize this molecule.

Quantitative real time PCR (qRT-PCR). Total cellular RNA was quantified spectrophotometrically and stored at −80° C. For the qRT-PCR, we used a commercial one-step master mix kit, with the thermal profile programmed as: first segment, 50° C. for 30 min, and 95° C. for 10 min (1 cycle); second segment, 95° C. for 30 sec, 62° C. for 30 sec, and 72° C. for 30 sec (40 cycles); and third segment, the reading was taken at 72° C. during the 30-sec plateau. The sequences of the qRT-PCR primers were: GAPDH forward, 5'-TGC CTC CTG CAC CAC CAA C-3' (SEQ ID No. 8) and reverse, 5'-GGC CAT CCA CAG TCT TCT GG-3' (SEQ ID No. 9); CXCL1 forward, 5'-CCC AAG AAC ATC CAA AGT GIG A-3' (SEQ ID No. 10) and CXCL1 reverse, 5'-GTC ACT GTT CAG CAT CTT TTC G-3' (SEQ ID No. 11).

Neutrophil apoptosis. Human neutrophils were isolated as described above and resuspended at $5 \times 10^6$ cells/ml in PBS$^+$, then aliquoted into 96-well plates at 100 μl per well. Medium (PBS+) alone or containing G31P (100 ng/ml) was added to the cells and incubated for 15 min at room temperature, before addition of CXCL1 or CXCL8 (100 ng/ml) or carrier medium alone. After 24 h at 37° C. the cells were stained as per the manufacturer's instructions using FITC-labeled annexin V and propidium iodide for FACS detection of apoptotic and necrotic cells, respectively, then analyzed within one hour using a FACScan flow cytometer.

In vivo confirmation of the anti-inflammatory activities of G31P. The assessment of G31P's effect on 15 h airway endotoxemia pathology in guinea pigs has been described previously for the bovine and human-bovine chimeric forms of G31P (Gordon et al., 2005; Zhao et al., 2007). Briefly, for challenge the animals (n=5) were given a 200 µl bolus of LPS (5 µg/kg) in sterile saline by intranasal intubation. At 30 min before challenge, 250 µg/kg G31P or an equivalent volume (1 ml) of saline was given s.c. and at 4, 8, or 16 h post-challenge the animals were euthanized with halothane. Bronchoalveolar lavage fluid (BAL) was collected using 2.0 ml volumes of sterile saline. BAL total WBC and red blood cells were enumerated by direct counting, and the results expressed as the mean number of cells per BAL sample (±SEM). BAL cell differentials were determined using Wright's solution-stained BAL cell cytospin preparations and the total numbers of neutrophils were calculated using these data. All the data are expressed as means±SEM. All BAL fluids were assessed independently (either immediately or after storage at −80° C.) for myloperoxidase (MPO), matrix metalloproteinase-9 (MMP-9), MMP-2, and lactoferrin (LF). This experiment was repeated twice.

Myeloperoxidase assay. BAL fluids (10 µl) were diluted 10-fold with 0.5% HTAB and incubated at room temperature for 10 min with 10 volumes of TMB, before stopping the reactions with 10 volumes of 1M phosphoric acid. The reactions were quantified by spectroscopy (OD, 450 nm) and the data expressed as the mean $OD_{450}$+/−SEM. Each sample was assayed in triplicate.

Assessment of BAL MMP-9 and MMP-2 levels. BAL levels of MMP-2 and -9 were measured by gel zymography, as previously described (10). Briefly, 20 µl samples of BAL sample were run on 7.5% SDS-PAGE gels containing 1 mg/ml gelatin. The gels were incubated overnight at room temperature in 2.5% Triton X-100, 50 mM Tris-HCl, 10 mM calcium chloride, 1 mM zinc chloride, rinsed in deionized water for 30 min, and then incubated overnight at 37° C. in 50 mM Tris-HCl, 10 mM calcium chloride, 1 mM zinc chloride, before staining with Coomassie brilliant blue. The identities of the gelatinolytic MMP-2 and -9 bands were determined based on their molecular weights and comparison with standards prepared from homogenates of untreated HT1080 fibrosarcoma cells (ATCC CCL21). The results are expressed as relative densitometry units for each gelatinase band.

Cell proliferation assay. B16-10 melanoma tumour cells were seeded in a 96-well plate and stimulated with MIP2+/− hG31P. After 48 hr, 3H-thy was added to all wells, and proliferation (3H-thy incorporation) was evaluated 72 hr later by liquid scintillation counting.

Melanoma metastasis model. Female C57/BL6 mice were given $1 \times 10^5$ B16-10 melanoma tumour cells i.v., and treated every other day with 500 µg/kg hG31P commencing on Day 5, 10 or 15. The mice were sacrificed on Day 21 for blood and tissue collection.

qRT-PCR. Tissues or tumour cells were homogenized using a RotoSTAR homogenizer and RNA extracted using a commercial kit (Qiagen). The levels of tumour antigens (Dct, Mfi2) or KC were assessed using a One-Step SYBRgreen master mix (Stratagene). Relative expression was determined using the ΔΔCt method with β-actin as the normalizing control.

Tissue cytokine analysis. Tissues were homogenized in PBS with protease inhibitors using a RotoSTAR homogenizer, and ELISAs were then used to detect cytokines in the supernatant.

Cell culture Human prostate cancer PC-3 cells (American Type Culture Collection), were maintained in complete medium (RPMI 1640 medium [Hyclone] containing 10% fetal bovine serum [FBS], with 1% ampicillin and streptomycin [Hyclone]). The cells were cultured at 37 C in a humidified 5% $CO_2$ atmosphere.

Cell proliferation assay Cell proliferation was analyzed using a commercial kit (WST-8 Cell Counting Kit-8; Sigma Chemical Co). PC-3 cells were trypsinized with 0.05% trypsin (Hyclone, USA) when they achieved 80% confluency to produce single cell suspensions, which were seeded into 96-well plates ($5 \times 10^3$ cells/well) in complete medium and incubated with G31P at 0-100 ng/ml for 72 h at 37° C. After this, 10 µl of the cell counting kit reagent were added to each well and the plates were incubated for an additional 4 h before the absorbance were determined at 450 nm using a 96-well plate reader. Each experiment was done in triplicate.

Cell Adhesion assay The wells of 96-well plates were dry-coated with the cell adhesion reagents (ECM, 10 µg/ml) (Sigma Chemical Co) and then rehydrated with PBS. The wells were filled with 1% heat-denatured BSA for 1 h at 37 C in a humidified atmosphere of 5% $CO_2$, then washed three times with PBS. Cells that had been treated with 0-100 ng/ml of G31P in serum free media for 24 h at 37 C (5% $CO_2$) were then seeded at $3 \times 10^5$ cells/well in the plates, incubated for 1 h at 37 C, then gently washed three times with PBS. The cells remaining adherent to the plates were enumerated using the cell counting reagent as above, and the absorbance determined at 450 nm.

Cell wound healing assay The wound healing assay was performed as known in the art. Cells were cultured in 12-well plates under standard culture conditions and allowed to reach 100% confluence. A 'wound' was made in the confluent monolayers with the tip of a 200-µl pipette tip and then the wells were rinsed three times with PBS. The cells were then incubated in complete medium at 37 C (5% $CO_2$) for 0-72 h in the presence of 0-100 ng/ml of G31P. The migration of the PC-3 cells into the 'wounded' area was evaluated at the indicated time points using an inverted microscope. The cell's wound-healing rates were quantified as the distance across the injury line during the culture, as determined at three different sites in each well.

GFP Gene Transduction of Prostate Cancer Cell Lines

In order to track tumour growth in vivo, we transfected the PC-3 cells with a gene for the green fluorescent protein. For this transduction, PC-3 human prostate cancer cells at 40% confluency were cultured for 72 h with a 1:1 mixture of precipitated retroviral PT67 cell supernatants (containing the GFP-expressing pLEIN retroviral vector; Clontech Laboratories, Palo Alto, Calif.) and RPMI 1640 medium containing 10% fetal bovine serum, after which the culture medium was replaced with complete medium. The tumour cells were harvested with 0.25% Trypsin and sub-cultured at 1:15 into selective medium containing 200 µg/mL G418. The level of G418 was increased to 1000 µg/mL in a stepwise manner in order to select brightly fluorescent cells, after which the fluorescent PC-3 cells were amplified and maintained by conventional culture methods in the absence of selective agent.

In Vivo Experiments

Athymic male nude mice (4-6 week-old BALB/c) were obtained from Yuanduan Labo Service Corporation (Nanjing, China) and maintained in a laminar airflow cabinet under specific pathogen-free conditions. The animals had free access to tapwater and standard pellet food, and their health was monitored daily. Monolayers of GFP-labeled PC-3 (PC-3-GFP) cells were harvested an $5 \times 10^6$ cells were inoculated subcutaneously on the right flank of three nude mice. The tumors were allowed to grow for 2 to 4 weeks and were harvested for passive transfer when palpable. To do this, the tumors of the three mice were resected and sliced into 1 mm$^3$ fragments, which were then implanted at the prostate of recipient nude mice under local anesthesia and sterile surgical conditions. A total of 48 animals received tumor fragment implants. Five days later (day 0), the animals (n=18/group) were assigned to one of three groups, which were injected s.c. every second day with 100 µl of normal saline (N.S.), G31P (0.5 mg/kg) or the anti-tumour drug paclitaxel (15 mg/kg). GFP fluorescence images of the growing tumors were captured on days 12, 18 and 24 using a digital camera in the optical configuration of a dissection microscope with a 515 nm emission filter. The tumor volumes were calculated using the formula (length×width$^2$)/2. All mice were sacrificed on day 24 for humanitarian reasons and the vascular microvessel densities were calculated using Image-Pro 6.0 Microsoft (MediaCybernetics). Tumor samples from each mouse were fixed in 4% paraformaldehyde and embedded in paraffin using standard procedures for subsequent immunohistochemistry analyses.

Immunohistochemical Analysis

Paraffin-embedded prostate tumor tissue sections collected from nude mice receiving normal saline, G31P or paclitaxel, as above, were dewaxed and rehydrated into PBS using standard procedures. The slides were rinsed three times with PBS and heat-treated for 15 min in 10 mM sodium citrate (pH 6.0), then endogenous peroxidase activities were blocked by treatment with 3% hydrogen peroxide for 10 min. The samples were rinsed three times with PBS, incubated for 15 min at room temperature with a protein-blocking solution of 5% normal horse serum in PBS (pH 7.5), washed three times with PBS, then incubated with a 1:50 dilution of a mouse monoclonal anti-VEGF antibody or a rabbit polyclonal anti-NF-κB p65 antibody (Santa Cruz Biotechnology Inc) for 20 h at 4° C. The samples were then rinsed three times with PBS and incubated for 40 min at 37° C. with the appropriate dilution of the secondary antibody, anti-mouse IgG or anti-rabbit IgG (Zhongshan Biotechnology). After washing three times with PBS, the sections were incubated with biotinylated goat anti-mouse or anti-rabbit immunoglobulin (Zhongshan Biotechnology) for 30 min. Finally, the specimens were incubated in diaminobenzidine (Zhongshan Biotechnology) for 10 min, then counterstained with haematoxylin. The primary antibody was omitted for negative controls.

While the preferred embodiments of the invention have been described above, it will be recognized and understood that various modifications may be made therein, and the appended claims are intended to cover all such modifications which may fall within the spirit and scope of the invention.

TABLE 1

Tumour Volumes as a function of time after orthotopic implantation

| Days After OI | Mean Tumor Volume (mm$^3$) ± SD | | | |
|---|---|---|---|---|
| | 0 | 19 | 25 | 29 |
| 1 Vehicle | 0 | 176.3 ± 185.3 | 902.4 ± 632.3 | 2767.8 ± 1133.9 |
| 2 Treated | 0 | 65.6 ± 58.7 | 288.5 ± 250.7 | 740.2 ± 959.2 |
| p-value | 0 | 0.298 | 0.084303 | 0.022573 |

TABLE 2

Tumour metastases at the end of the study (dy 29)

| Group | Animal ID | Lumber L.N.* | Mesentery L.N. | Pancreas | Mediastinum L.N. | Liver |
|---|---|---|---|---|---|---|
| 1 Vehicle | 1-1# | N/A** | | | | |
| | 1-2# | + | + | + | | |
| | 1-3# | + | | + | + | + |
| | 1-4# | + | | | | |
| | 1-5# | + | + | + | | |
| | 1-6# | N/A | | | | |
| 2 Treated | 2-1# | N/A | | | | |
| | 2-2# | + | | | | |
| | 2-3# | | | | | |
| | 2-4# | + | + | | | |
| | 2-5# | + | | | | |
| | 2-6# | + | | | | |

*L.N.: Lymph Node
**N/A: The animal not used for evaluation due to non-take.

TABLE 3

Impact of G31P treatment on blood vessel development in an orthotopic model of prostate cancer

| Group | Animal ID | Total vessel length* mm/mm2 | Group | Animal ID | Total vessel length mm/mm2 |
|---|---|---|---|---|---|
| 1 Vehicle | 1-1# | N/A | 2 Treated | 2-1# | N/A |
| | 1-2# | 0.7 | | 2-2# | 1.32 |
| | 1-3# | 2.1 | | 2-3# | 1.63 |
| | 1-4# | 2.94 | | 2-4# | 2.38 |
| | 1-5# | 3.31 | | 2-5# | 1.58 |
| | 1-6# | N/A | | 2-6# | 1.26 |
| Mean | | 2.3 | Mean | | 1.6 |
| SD | | 1.2 | SD | | 0.4 |

The invention claimed is:

1. A method of treating a cancer selected from the group consisting of melanoma, prostate cancer, pancreatic cancer and hepatic cancer in an individual in need of such treatment comprising administering to said individual an effective amount of G31P (SEQ ID NO:1).

2. The method according to claim 1 wherein the cancer is selected from the group consisting of melanoma, prostate cancer and hepatic cancer.

3. The method according to claim 1 wherein the cancer is selected from the group consisting of melanoma, prostate cancer and pancreatic cancer.

4. The method according to claim 1 wherein the cancer is selected from the group consisting of pancreatic cancer, prostate cancer and hepatic cancer.

5. The method according to claim 1 wherein the cancer is selected from the group consisting of melanoma, pancreatic cancer and hepatic cancer.

6. The method according to claim 1 wherein the cancer is melanoma.

7. The method according to claim 1 wherein the cancer is prostate cancer.

8. The method according to claim 1 wherein the cancer is pancreatic cancer.

9. The method according to claim 1 wherein the cancer is hepatic cancer.

* * * * *